(12) United States Patent
de Boer et al.

(10) Patent No.: US 7,643,153 B2
(45) Date of Patent: *Jan. 5, 2010

(54) APPARATUS AND METHOD FOR RANGING AND NOISE REDUCTION OF LOW COHERENCE INTERFEROMETRY LCI AND OPTICAL COHERENCE TOMOGRAPHY OCT SIGNALS BY PARALLEL DETECTION OF SPECTRAL BANDS

(75) Inventors: Johannes F. de Boer, Somerville, MA (US); Guillermo J. Tearney, Cambridge, MA (US); Brett Eugene Bouma, Quincy, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/956,079

(22) Filed: Dec. 13, 2007

(65) Prior Publication Data
US 2008/0094637 A1   Apr. 24, 2008

Related U.S. Application Data

(62) Division of application No. 10/501,276, filed as application No. PCT/US03/02349 on Jan. 24, 2003, now Pat. No. 7,355,716.

(51) Int. Cl.
  G01B 9/02   (2006.01)
  G01B 11/02  (2006.01)
(52) U.S. Cl. ...................... 356/497; 356/479
(58) Field of Classification Search ............. 356/479, 356/497, 456
See application file for complete search history.

(56) References Cited

U.S. PATENT DOCUMENTS 2,339,754 A   1/1944   Brace
(Continued)

FOREIGN PATENT DOCUMENTS
DE   4309056   9/1994
(Continued)

OTHER PUBLICATIONS

Fujimoto et al., "High Resolution in Vivo Intra-Arterial Imaging with Optical Coherence Tomography," *Official Journal of the British Cardiac Society*, vol. 82, pp. 128-133 Heart, 1999.

(Continued)

*Primary Examiner*—Patrick J Connolly
(74) *Attorney, Agent, or Firm*—Dorsey & Whitney LLP

(57) ABSTRACT

Apparatus, method, logic arrangement and storage medium are provided for increasing the sensitivity in the detection of optical coherence tomography and low coherence interferometry ("LCI") signals by detecting a parallel set of spectral bands, each band being a unique combination of optical frequencies. The LCI broad bandwidth source can be split into N spectral bands. The N spectral bands can be individually detected and processed to provide an increase in the signal-to-noise ratio by a factor of N. Each spectral band may be detected by a separate photo detector and amplified. For each spectral band, the signal can be band pass filtered around the signal band by analog electronics and digitized, or, alternatively, the signal may be digitized and band pass filtered in software. As a consequence, the shot noise contribution to the signal is likely reduced by a factor equal to the number of spectral bands, while the signal amplitude can remain the same. The reduction of the shot noise increases the dynamic range and sensitivity of the system.

15 Claims, 19 Drawing Sheets

U.S. PATENT DOCUMENTS

| | | |
|---|---|---|
| 3,601,480 A | 8/1971 | Randall |
| 3,856,000 A | 12/1974 | Chikama |
| 3,941,121 A | 3/1976 | Olinger |
| 3,973,219 A | 8/1976 | Tang et al. |
| 3,983,507 A | 9/1976 | Tang et al. |
| 4,030,827 A | 6/1977 | Delhaye et al. |
| 4,141,362 A | 2/1979 | Wurster |
| 4,295,738 A | 10/1981 | Meltz et al. |
| 4,300,816 A | 11/1981 | Snitzer et al. |
| 4,479,499 A | 10/1984 | Alfano |
| 4,533,247 A | 8/1985 | Epworth |
| 4,585,349 A | 4/1986 | Gross et al. |
| 4,601,036 A | 7/1986 | Faxvog et al. |
| 4,607,622 A | 8/1986 | Fritch et al. |
| 4,631,498 A | 12/1986 | Cutler |
| 4,770,492 A | 9/1988 | Levin et al. |
| 4,868,834 A | 9/1989 | Fox et al. |
| 4,925,302 A | 5/1990 | Cutler |
| 4,928,005 A | 5/1990 | Lefèvre et al. |
| 4,965,441 A | 10/1990 | Picard |
| 4,993,834 A | 2/1991 | Carlhoff et al. |
| 5,039,193 A | 8/1991 | Snow et al. |
| 5,040,889 A | 8/1991 | Keane |
| 5,045,936 A | 9/1991 | Lobb et al. |
| 5,046,501 A | 9/1991 | Crilly |
| 5,065,331 A | 11/1991 | Vachon et al. |
| 5,120,953 A | 6/1992 | Harris |
| 5,127,730 A | 7/1992 | Brelje et al. |
| 5,197,470 A | 3/1993 | Helfer et al. |
| 5,202,745 A | 4/1993 | Sorin et al. |
| 5,248,876 A | 9/1993 | Kerstens et al. |
| 5,250,186 A | 10/1993 | Dollinger et al. |
| 5,262,644 A | 11/1993 | Maguire |
| 5,291,885 A | 3/1994 | Taniji et al. |
| 5,293,872 A | 3/1994 | Alfano et al. |
| 5,293,873 A | 3/1994 | Fang |
| 5,304,810 A | 4/1994 | Amos |
| 5,305,759 A | 4/1994 | Kaneko et al. |
| 5,317,389 A | 5/1994 | Hochberg et al. |
| 5,321,501 A | 6/1994 | Swanson et al. |
| 5,348,003 A | 9/1994 | Caro |
| 5,353,790 A | 10/1994 | Jacques et al. |
| 5,383,467 A | 1/1995 | Auer et al. |
| 5,394,235 A | 2/1995 | Takeuchi et al. |
| 5,411,016 A | 5/1995 | Kume et al. |
| 5,419,323 A | 5/1995 | Kittrell et al. |
| 5,439,000 A | 8/1995 | Gunderson et al. |
| 5,441,053 A | 8/1995 | Lodder et al. |
| 5,450,203 A | 9/1995 | Penkethman |
| 5,454,807 A | 10/1995 | Lennox et al. |
| 5,459,325 A | 10/1995 | Hueton et al. |
| 5,459,570 A | 10/1995 | Swanson et al. |
| 5,465,147 A | 11/1995 | Swanson |
| 5,486,701 A | 1/1996 | Norton et al. |
| 5,491,524 A | 2/1996 | Hellmuth et al. |
| 5,491,552 A | 2/1996 | Knuttel |
| 5,526,338 A | 6/1996 | Hasman et al. |
| 5,562,100 A | 10/1996 | Kittrell et al. |
| 5,565,986 A * | 10/1996 | Knuttel ...................... 356/456 |
| 5,583,342 A | 12/1996 | Ichie |
| 5,590,660 A | 1/1997 | MacAulay et al. |
| 5,600,486 A | 2/1997 | Gal et al. |
| 5,601,087 A | 2/1997 | Richards-Kortum et al. |
| 5,621,830 A | 4/1997 | Lucey et al. |
| 5,623,336 A | 4/1997 | Raab et al. |
| 5,697,373 A | 12/1997 | Gunderson et al. |
| 5,698,397 A | 12/1997 | Zarling et al. |
| 5,710,630 A | 1/1998 | Essenpreis et al. |
| 5,719,399 A | 2/1998 | Alfano et al. |
| 5,735,276 A | 4/1998 | Lemelson |
| 5,740,808 A | 4/1998 | Panescu et al. |
| 5,748,598 A | 5/1998 | Swanson et al. |
| 5,784,352 A | 7/1998 | Swanson et al. |
| 5,785,651 A | 7/1998 | Kuhn et al. |
| 5,795,295 A | 8/1998 | Hellmuth et al. |
| 5,801,826 A | 9/1998 | Williams |
| 5,803,082 A | 9/1998 | Stapleton et al. |
| 5,807,261 A | 9/1998 | Benaron et al. |
| 5,817,144 A | 10/1998 | Gregory |
| 5,840,023 A | 11/1998 | Oraevsky et al. |
| 5,842,995 A | 12/1998 | Mahadevan-Jansen et al. |
| 5,843,000 A | 12/1998 | Nishioka et al. |
| 5,843,052 A | 12/1998 | Benja-Athon |
| 5,847,827 A | 12/1998 | Fercher |
| 5,862,273 A | 1/1999 | Pelletier |
| 5,865,754 A | 2/1999 | Sevick-Muraca et al. |
| 5,867,268 A | 2/1999 | Gelikonov et al. |
| 5,871,449 A | 2/1999 | Brown |
| 5,872,879 A | 2/1999 | Hamm |
| 5,877,856 A | 3/1999 | Fercher |
| 5,887,009 A | 3/1999 | Mandella et al. |
| 5,892,583 A | 4/1999 | Li |
| 5,920,373 A | 7/1999 | Bille |
| 5,920,390 A | 7/1999 | Farahi et al. |
| 5,921,926 A | 7/1999 | Rolland et al. |
| 5,949,929 A | 9/1999 | Hamm |
| 5,951,482 A | 9/1999 | Winston et al. |
| 5,956,355 A * | 9/1999 | Swanson et al. .............. 372/20 |
| 5,968,064 A | 10/1999 | Selmon et al. |
| 5,983,125 A | 11/1999 | Alfano et al. |
| 5,987,346 A | 11/1999 | Benaron et al. |
| 5,991,697 A | 11/1999 | Nelson et al. |
| 5,994,690 A | 11/1999 | Kulkarni et al. |
| 5,995,223 A * | 11/1999 | Power ....................... 356/495 |
| 6,002,480 A * | 12/1999 | Izatt et al. ................... 356/479 |
| 6,004,314 A | 12/1999 | Wei et al. |
| 6,006,128 A | 12/1999 | Izatt et al. |
| 6,010,449 A | 1/2000 | Selmon et al. |
| 6,014,214 A | 1/2000 | Li |
| 6,016,197 A | 1/2000 | Krivoshlykov |
| 6,033,721 A | 3/2000 | Nassuphis |
| 6,044,288 A | 3/2000 | Wake et al. |
| 6,048,742 A | 4/2000 | Weyburne et al. |
| 6,053,613 A | 4/2000 | Wei et al. |
| 6,069,698 A | 5/2000 | Ozawa et al. |
| 6,091,496 A | 7/2000 | Hill |
| 6,091,984 A | 7/2000 | Perelman et al. |
| 6,111,645 A | 8/2000 | Tearney et al. |
| 6,117,128 A | 9/2000 | Gregory |
| 6,120,516 A | 9/2000 | Selmon et al. |
| 6,134,003 A | 10/2000 | Tearney et al. |
| 6,134,010 A | 10/2000 | Zavislan |
| 6,134,033 A | 10/2000 | Bergano et al. |
| 6,141,577 A | 10/2000 | Rolland et al. |
| 6,151,522 A | 11/2000 | Alfano et al. |
| 6,159,445 A | 12/2000 | Klaveness et al. |
| 6,160,826 A | 12/2000 | Swanson et al. |
| 6,161,031 A | 12/2000 | Hochman et al. |
| 6,166,373 A | 12/2000 | Mao |
| 6,174,291 B1 | 1/2001 | McMahon et al. |
| 6,175,669 B1 | 1/2001 | Colston et al. |
| 6,185,271 B1 | 2/2001 | Kinsinger |
| 6,191,862 B1 | 2/2001 | Swanson et al. |
| 6,193,676 B1 | 2/2001 | Winston et al. |
| 6,198,956 B1 | 3/2001 | Dunne |
| 6,201,989 B1 | 3/2001 | Whitehead et al. |
| 6,208,415 B1 | 3/2001 | De Boer et al. |
| 6,208,887 B1 | 3/2001 | Clarke |
| 6,249,349 B1 | 6/2001 | Lauer |
| 6,249,381 B1 | 6/2001 | Suganuma |
| 6,263,234 B1 | 7/2001 | Engelhardt et al. |
| 6,264,610 B1 | 7/2001 | Zhu |
| 6,272,376 B1 | 8/2001 | Marcu et al. |
| 6,274,871 B1 | 8/2001 | Dukor et al. |

| | | |
|---|---|---|
| 6,282,011 B1 | 8/2001 | Tearney et al. |
| 6,308,092 B1 | 10/2001 | Hoyns |
| 6,324,419 B1 | 11/2001 | Guzelsu et al. |
| 6,341,036 B1 | 1/2002 | Tearney et al. |
| 6,353,693 B1 | 3/2002 | Kano et al. |
| 6,374,128 B1 | 4/2002 | Toida et al. |
| 6,377,349 B1 | 4/2002 | Fercher |
| 6,384,915 B1 | 5/2002 | Everett et al. |
| 6,393,312 B1 | 5/2002 | Hoyns |
| 6,394,964 B1 | 5/2002 | Sievert, Jr. et al. |
| 6,421,164 B2 | 7/2002 | Tearney et al. |
| 6,445,944 B1 | 9/2002 | Ostrovsky |
| 6,463,313 B1 | 10/2002 | Winston et al. |
| 6,469,846 B2 | 10/2002 | Ebizuka et al. |
| 6,485,413 B1 | 11/2002 | Boppart et al. |
| 6,485,482 B1 | 11/2002 | Belef |
| 6,501,551 B1 | 12/2002 | Tearney et al. |
| 6,501,878 B2 | 12/2002 | Hughes et al. |
| 6,549,801 B1 | 4/2003 | Chen et al. |
| 6,552,796 B2 | 4/2003 | Magnin et al. |
| 6,556,305 B1 | 4/2003 | Aziz et al. |
| 6,556,853 B1 | 4/2003 | Cabib et al. |
| 6,558,324 B1 | 5/2003 | Von Behren et al. |
| 6,564,087 B1 | 5/2003 | Pitris et al. |
| 6,564,089 B2 | 5/2003 | Izatt et al. |
| 6,615,071 B1 | 9/2003 | Casscells, III et al. |
| 6,622,732 B2 | 9/2003 | Constantz |
| 6,680,780 B1 | 1/2004 | Fee |
| 6,685,885 B2 | 2/2004 | Nolte et al. |
| 6,687,007 B1 | 2/2004 | Meigs |
| 6,687,010 B1 | 2/2004 | Horii et al. |
| 6,741,355 B2 | 5/2004 | Drabarek |
| 6,790,175 B1 | 9/2004 | Furusawa et al. |
| 6,806,963 B1 | 10/2004 | Wälti et al. |
| 6,816,743 B2 | 11/2004 | Moreno et al. |
| 6,909,105 B1 | 6/2005 | Heintzmann et al. |
| 6,980,299 B1 | 12/2005 | de Boer |
| 7,006,231 B2 | 2/2006 | Ostrovsky et al. |
| 7,019,838 B2 | 3/2006 | Izatt et al. |
| 7,231,243 B2 | 6/2007 | Tearney et al. |
| 7,236,637 B2 | 6/2007 | Sirohey et al. |
| 7,336,366 B2 | 2/2008 | Choma et al. |
| 7,355,716 B2 * | 4/2008 | de Boer et al. ............... 356/479 |
| 7,391,520 B2 * | 6/2008 | Zhou et al. .................. 356/479 |
| 2001/0047137 A1 | 11/2001 | Moreno et al. |
| 2002/0016533 A1 | 2/2002 | Marchitto et al. |
| 2002/0048026 A1 | 4/2002 | Isshiki et al. |
| 2002/0064341 A1 | 5/2002 | Fauver et al. |
| 2002/0076152 A1 | 6/2002 | Hughes et al. |
| 2002/0085209 A1 | 7/2002 | Mittleman et al. |
| 2002/0122246 A1 | 9/2002 | Tearney et al. |
| 2002/0161357 A1 | 10/2002 | Rox et al. |
| 2002/0163622 A1 | 11/2002 | Magnin et al. |
| 2002/0172485 A1 | 11/2002 | Keaton et al. |
| 2002/0188204 A1 | 12/2002 | McNamara et al. |
| 2002/0196446 A1 | 12/2002 | Roth et al. |
| 2002/0198457 A1 | 12/2002 | Tearney et al. |
| 2003/0023153 A1 | 1/2003 | Izatt et al. |
| 2003/0026735 A1 | 2/2003 | Nolte et al. |
| 2003/0135101 A1 | 7/2003 | Webler |
| 2003/0164952 A1 | 9/2003 | Deichmann et al. |
| 2003/0171691 A1 | 9/2003 | Casscells, III et al. |
| 2003/0236443 A1 | 12/2003 | Cespedes et al. |
| 2004/0086245 A1 | 5/2004 | Farroni et al. |
| 2004/0100631 A1 | 5/2004 | Bashkansky et al. |
| 2004/0100681 A1 | 5/2004 | Bjarklev et al. |
| 2004/0150829 A1 | 8/2004 | Koch et al. |
| 2004/0166593 A1 | 8/2004 | Nolte et al. |
| 2005/0018201 A1 * | 1/2005 | de Boer et al. ............... 356/479 |
| 2005/0057680 A1 | 3/2005 | Agan |
| 2005/0075547 A1 | 4/2005 | Wang |
| 2005/0083534 A1 | 4/2005 | Riza et al. |
| 2007/0019208 A1 * | 1/2007 | Toida et al. .................. 356/511 |
| 2007/0291277 A1 * | 12/2007 | Everett et al. ............... 356/497 |

FOREIGN PATENT DOCUMENTS

| | | |
|---|---|---|
| DE | 1 9542955 | 5/1997 |
| DE | 1 0351319 | 6/2005 |
| EP | 0110201 | 6/1984 |
| EP | 0251062 | 1/1988 |
| EP | 0590268 | 4/1994 |
| EP | 1426799 | 6/2004 |
| GB | 1257778 | 12/1971 |
| GB | 2030313 | 4/1980 |
| GB | 2209221 | 5/1989 |
| JP | 4135550 | 5/1992 |
| JP | 4135551 | 5/1992 |
| WO | 9219930 | 11/1992 |
| WO | 9303672 | 3/1993 |
| WO | 9533971 | 12/1995 |
| WO | 9732182 | 9/1997 |
| WO | 9801074 | 1/1998 |
| WO | 9814132 | 4/1998 |
| WO | 9835203 | 8/1998 |
| WO | 9838907 | 9/1998 |
| WO | 9846123 | 10/1998 |
| WO | 9848838 | 11/1998 |
| WO | 9944089 | 9/1999 |
| WO | 9957507 | 11/1999 |
| WO | 0058766 | 10/2000 |
| WO | 0138820 | 5/2001 |
| WO | 0142735 | 6/2001 |
| WO | 0236015 | 5/2002 |
| WO | 0238040 | 5/2002 |
| WO | 0254027 | 7/2002 |
| WO | 03 020119 | 3/2003 |
| WO | 03 062802 | 7/2003 |
| WO | WO 03/062802 | 7/2003 |
| WO | 2004 066824 | 8/2004 |
| WO | 2004 088361 | 10/2004 |
| WO | 2004 105598 | 12/2004 |
| WO | 2005 000115 | 1/2005 |
| WO | WO 2005/047813 | 5/2005 |
| WO | 2005 054780 | 6/2005 |
| WO | 2006 014392 | 2/2006 |
| WO | 2006 130797 | 12/2006 |

OTHER PUBLICATIONS

D. Huang et al., "Optical Coherence Tomography," *Science*, vol. 254, pp. 1178-1181, Nov. 1991.

Tearney et al., "High-Speed Phase—and Group Delay Scanning with a Grating Based Phase Control Delay Line," *Optics Letters*, vol. 22, pp. 1811-1813, Dec. 1997.

Rollins, et al., "In Vivo Video Rate Optical Coherence Tomography," *Optics Express*, vol. 3, pp. 219-229, Sep. 1998.

Saxer, et al., High Speed Fiber-Based Polarization-Sensitive Optical Coherence Tomography of in Vivo Human Skin, *Optical Society of America*, vol. 25, pp. 1355-1357, Sep. 2000.

Oscar Eduardo Martinez, "3000 Times Grating Compress or with Positive Group Velocity Dispersion," *IEEE*, vol. QE-23, pp. 59-64, Jan. 1987.

Kulkarni, et al., "Image Enhancement in Optical Coherence Tomography Using Deconvolution," *Electronics Letters*, vol. 33, pp. 1365-1367, Jul. 1997.

Bashkansky, et al., "Signal Processing for Improving Field Cross-Correlation Function in Optical Coherence Tomography," *Optics & Photonics News*, vol. 9, pp. 8137-8138, May 1998.

Yung et al., "Phase-Domain Processing of Optical Coherence Tomography Images," *Journal of Biomedical Optics*, vol. 4, pp. 125-136, Jan. 1999.

Tearney, et al., "In Vivo Endoscopic Optical Biopsy with Optical Coherence Tomography," *Science*, vol. 276, Jun. 1997.

W. Drexler et al., "In Vivo Ultrahigh-Resolution Optical Coherence Tomography," *Optics Letters* vol. 24, pp. 1221-1223, Sep. 1999.

Nicusor V. Iftimia et al., "A Portable, Low Coherence Interferometry Based Instrument for Fine Needle Aspiration Biopsy Guidance," Accepted to Review of Scientific Instruments, 2005.

Abbas, G.L., V.W.S. Chan et al., "Local-Oscillator Excess-Noise Suppression for Homodyne and Heterodyne-Detection," *Optics Letters*, vol. 8, pp. 419-421, Aug. 1983 issue.

Agrawal, G.P., "Population Pulsations and Nondegenerate 4-Wave Mixing in Semiconductor-Lasers and Amplifiers," *Journal Of The Optical Society Of America B-Optical Physics*, vol. 5, pp. 147-159, Jan. 1998.

Andretzky, P. et al., "Optical Coherence Tomography by Spectral Radar: Improvement of Signal-to-Noise Ratio," *The International Society for Optical Engineering*, USA, vol. 3915, 2000.

Ballif, J. et al., "Rapid and Scalable Scans at 21 m/s in optical Low-Coherence Reflectometry," *Optics Letters*, vol. 22, pp. 757-759, Jun. 1997.

Barfuss H. et al., "Modified Optical Frequency-Domain Reflectometry with High Spatial-Resolution for Components of Integrated Optic Systems," *Journal Of Lightwave Technology*, vol. 7, pp. 3-10, Jan. 1989.

Beaud, P. et al., "Optical Reflectometry with Micrometer Resolution for the Investigation of Integrated Optical-Devices," *Ieee Journal of Quantum Electronics*, vol. 25, pp. 755-759, Apr. 1989.

Bouma, Brett et al., "Power-Efficient Nonreciprocal Interferometer and Linear-Scanning Fiber-Optic Catheter for Optical Coherence Tomography," *Optics Letters*, vol. 24, pp. 531-533, Apr. 1999.

Brinkmeyer, E. et al., "Efficient Algorithm for Non-Equidistant Interpolation of Sampled Data," *Electronics Letters*, vol. 28, p. 693, Mar. 1992.

Brinkmeyer, E. et al., "High-Resolution OCDR in Dispersive Wave-Guides," *Electronics Letters*, vol. 26, pp. 413-414, Mar. 1990.

Chinn, S.R. et al., "Optical Coherence Tomography Using a Frequency-Tunable Optical Source," *Optics Letters*, vol. 22, pp. 340-342, Mar. 1997.

Danielson, B.L. et al., "Absolute Optical Ranging Using Low Coherence Interferometry," *Applied Optics*, vol. 30, p. 2975, Jul. 1991.

Dorrer, C. et al., "Spectral Resolution and Sampling Issues in Fourier-Transform Spectral Interferometry," *Journal of the Optical Society of America B-Optical Physics*, vol. 17, pp. 1795-1802, Oct. 2000.

Dudley, J.M. et al., "Cross-Correlation Frequency Resolved Optical Gating Analysis of Broadband Continuum Generation in Photonic Crystal Fiber: Simulations and Experiments," *Optics Express*, vol. 10, p. 1215, Oct. 2002.

Eickhoff, W. et al., "Optical Frequency-Domain Reflectometry in Single-Mode Fiber," *Applied Physics Letters*, vol. 39, pp. 693-695, 1981.

Fercher, Adolf "Optical Coherence Tomography," *Journal of Biomedical Optics*, vol. 1, pp. 157-173, Apr. 1996.

Ferreira, L.A. et al., "Polarization-Insensitive Fiberoptic White-Light Interferometry," *Optics Communications*, vol. 114, pp. 386-392, Feb. 1995.

Fujii, Yohji, "High-Isolation Polarization-Independent Optical Circulator", *Journal of Lightwave Technology*, vol. 9, pp. 1239-1243, Oct. 1991.

Glance, B., "Polarization Independent Coherent Optical Receiver," *Journal of Lightwave Technology*, vol. LT-5, p. 274, Feb. 1987.

Glombitza, U., "Coherent Frequency-Domain Reflectometry for Characterization of Single-Mode Integrated-Optical Wave-Guides," *Journal of Lightwave Technology*, vol. 11, pp. 1377-1384, Aug. 1993.

Golubovic, B. et al., "Optical Frequency-Domain Reflectometry Using Rapid Wavelength Tuning of a Cr4+:Forsterite Laser," *Optics Letters*, vol. 11, pp. 1704-1706, Nov. 1997.

Haberland, U. H. P. et al., "Chirp Optical Coherence Tomography of Layered Scattering Media," *Journal of Biomedical Optics*, vol. 3, pp. 259-266, Jul. 1998.

Hammer, Daniel X. et al., "Spectrally Resolved White-Light Interferometry for Measurement of Ocular Dispersion," *Journal of the Optical Society of America A-Optics Image Science and Vision*, vol. 16, pp. 2092-2102, Sep. 1999.

Harvey, K. C. et al., "External-Cavity Diode-Laser Using a Grazing-Incidence Diffraction Grating," *Optics Letters*, vol. 16, pp. 910-912, Jun. 1991.

Hausler, Gerd et al., "'Coherence Radar' and 'Spectral Radar' New Tools for Dermatological Diagnosis," *Journal of Biomedical Optics*, vol. 3, pp. 21-31, Jan. 1998.

Hee, Michael R. et al., "Polarization-Sensitive Low-Coherence Reflectometer for Birefringence Characterization and Ranging," *Journal of the Optical Society of America B (Optical Physics)*, vol. 9, p. 903-908, Jun. 1992.

Hotate Kazuo et al., "Optical Coherence Domain Reflectometry by Synthesis of Coherence Function," *Journal of Lightwave Technology*, vol. 11, pp. 1701-1710, Oct. 1993.

Inoue, Kyo et al., "Nearly Degenerate 4-Wave-Mixing in a Traveling-Wave Semiconductor-Laser Amplifier," *Applied Physics Letters*, vol. 51, pp. 1051-1053, 1987.

Ivanov, A. P. et al., "New Method for High-Range Resolution Measurements of Light Scattering in Optically Dense Inhomogeneous Media," *Optics Letters*, vol. 1, pp. 226-228, Dec. 1977.

Ivanov, A. P. et al., "Interferometric Study of the Spatial Structure of a Light-Scattering Medium," *Journal of Applied Spectroscopy*, vol. 28, pp. 518-525, 1978.

Kazovsky, L. G. et al., "Heterodyne Detection Through Rain, Snow, and Turbid Media: Effective Receiver Size at Optical Through Millimeter Wavelenghths," *Applied Optics*, vol. 22, pp. 706-710, Mar. 1983.

Kersey, A. D. et al., "Adaptive Polarization Diversity Receiver Configuration for Coherent Optical Fiber Communications," *Electronics Letters*, vol. 25, pp. 275-277, Feb. 1989.

Kohlhaas, Andreas et al., "High-Resolution OCDR for Testing Integrated-Optical Waveguides: Dispersion-Corrupted Experimental Data Corrected by a Numerical Algorithm," *Journal of Lightwave Technology*, vol. 9, pp. 1493-1502, Nov. 1991.

Larkin, Kieran G., "Efficient Nonlinear Algorithm for Envelope Detection in White Light Interferometry," *Journal of the Optical Society of America A-Optics Image Science and Vision*, vol. 13, pp. 832-843, Apr. 1996.

Leitgeb, R. et al., "Spectral measurement of Absorption by Spectroscopic Frequency-Domain Optical Coherence Tomography," *Optics Letters*, vol. 25, pp. 820-822, Jun. 2000.

Lexer, F. et al., "Wavelength-Tuning Interferometry of Intraocular Distances," *Applied Optics*, vol. 36, pp. 6548-6553, Sep. 1997.

Mitsui, Takahisa, "Dynamic Range of Optical Reflectometry with Spectral Interferometry," *Japanese Journal of Applied Physics Part 1-Regular Papers Short Notes & Review Papers*, vol. 38, pp. 6133-6137, 1999.

Naganuma, Kazunori et al., "Group-Delay Measurement Using the Fourier-Transform of an Interferometric Cross-Correlation Generated by White Light," *Optics Letters*, vol. 15, pp. 393-395, Apr. 1990.

Okoshi, Takanori, "Polarization-State Control Schemes for Heterodyne or Homodyne Optical Fiber Communications," *Journal of Lightwave Technology*, vol. LT-3, pp. 1232-1237, Dec. 1995.

Passy, R. et al., "Experimental and Theoretical Investigations of Coherent OFDR with Semiconductor-Laser Sources," *Journal of Lightwave Technology*, vol. 12, pp. 1622-1630, Sep. 1994.

Podoleanu, Adrian G., "Unbalanced Versus Balanced Operation in an Optical Coherence Tomography System," *Applied Optics*, vol. 39, pp. 173-182, Jan. 2000.

Price, J. H. V. et al., "Tunable, Femtosecond Pulse Source Operating in the Range 1.06-1.33 mu m Based on an Yb3+-doped Holey Fiber Amplifier," *Journal of the Optical Society of America B-Optical Physics*, vol. 19, pp. 1286-1294, Jun. 2002.

Schmitt, J. M. et al, "Measurement of Optical-Properties of Biological Tissues by Low-Coherence Reflectometry," *Applied Optics*, vol. 32, pp. 6032-6042, Oct. 1993.

Silberberg, Y. et al., "Passive-Mode Locking of a Semiconductor Diode-Laser," *Optics Letters*, vol. 9, pp. 507-509, Nov. 1984.

Smith, L. Montgomery et al., "Absolute Displacement Measurements Using Modulation of the Spectrum of White-Light in a Michelson Interferometer," *Applied Optics*, vol. 28, pp. 3339-3342, Aug. 1989.

Sonnenschein, C. M. et al., "Signal-To-Noise Relationships for Coaxial Systems that Heterodyne Backscatter from Atmosphere," *Applied Optics*, vol. 10, pp. 1600-1604, Jul. 1971.

Sorin, W. V. et al., "Measurement of Rayleigh Backscattering at 1.55 mu m with 32 mu m Spatial Resolution," *IEEE Photonics Technology Letters*, vol. 4, pp. 374-376, Apr. 1992.

Sorin, W. V. et al., "A Simple Intensity Noise-Reduction Technique for Optical Low-Coherence Reflectometry," *IEEE Photonics Technology Letters*, vol. 4, pp. 1404-1406, Dec. 1992.

Swanson, E. A. et al., "High-Speed Optical Coherence Domain Reflectometry," *Optics Letters*, vol. 17, pp. 151-153, Jan. 1992.

Takada, K. et al., "High-Resolution OFDR with Incorporated Fiberoptic Frequency Encoder," *IEEE Photonics Technology Letters*, vol. 4, pp. 1069-1072, Sep. 1992.

Takada, Kazumasa et al., "Narrow-Band light Source with Acoustooptic Tunable Filter for Optical Low-Coherence Reflectometry," *IEEE Photonics Technology Letters*, vol. 8, pp. 658-660, May 1996.

Takada, Kazumasa et al., "New Measurement System for Fault Location in Optical Wave-Guide Devices Based on an Interometric-Technique," *Applied Optics*, vol. 26, pp. 1603-1606, May 1987.

Tateda, Mitsuhiro et al., "Interferometric Method for Chromatic Dispersion Measurement in a Single-Mode Optical Fiber," *IEEE Journal Of Quantum Electronics*, vol. 17, pp. 404-407, Mar. 1981.

Toide, M. et al., "Two-Dimensional Coherent Detection Imaging in Multiple Scattering Media Based the Directional Resolution Capability of the Optical Heterodyne Method," *Applied Physics B (Photophysics and Laser Chemistry)*, vol. B52, pp. 391-394, 1991.

Trutna, W. R. et al., "Continuously Tuned External-Cavity Semiconductor-Laser," *Journal of Lightwave Technology*, vol. 11, pp. 1279-1286, Aug. 1993.

Uttam, Deepak et al., "Precision Time Domain Reflectometry in Optical Fiber Systems Using a Frequency Modulated Continuous Wave Ranging Technique," *Journal of Lightwave Technology*, vol. 3, pp. 971-977, Oct. 1985.

Von Der Weid, J. P. et al., "On the Characterization of Optical Fiber Network Components with Optical Frequency Domain Reflectometry," *Journal of Lightwave Technology*, vol. 15, pp. 1131-1141, Jul. 1997.

Wysocki, P.F. et al., "Broad-Spectrum, Wavelength-Swept, Erbium-Doped Fiber Laser at 1.55-Mu-M," *Optics Letters*, vol. 15, pp. 879-881, Aug. 1990.

Youngquist, Robert C. et al., "Optical Coherence-Domain Reflectometry—A New Optical Evaluation Technique," *Optics Letters*, vol. 12, pp. 158-160, Mar. 1987.

Yun, S. H. et al., "Wavelength-Swept Fiber Laser with Frequency Shifted Feedback and Resonantly Swept Intra-Cavity Acoustooptic Tunable Filter," *IEEE Journal of Selected Topics in Quantum Electronics*, vol. 3, pp. 1087-1096, Aug. 1997.

Yun, S. H. et al., "Interrogation of Fiber Grating Sensor Arrays with a Wavelength-Swept Fiber Laser," *Optics Letters*, vol. 23, pp. 843-845, Jun. 1998.

Yung, K. M., "Phase-Domain Processing of Optical Coherence Tomography Images," *Journal of Biomedical Optics*, vol. 4, pp. 125-136, Jan. 1999.

Zhou, Xiao-Qun et al., "Extended-Range FMCW Reflectometry Using an optical Loop with a Frequency Shifter," *IEEE Photonics Technology Letters*, vol. 8, pp. 248-250, Feb. 1996.

Zorabedian, Paul et al., "Tuning Fidelity of Acoustooptically Controlled External Cavity Semiconductor-Lasers," *Journal of Lightwave Technology*, vol. 13, pp. 62-66, Jan. 1995.

Victor S. Y. Lin et al., "A Porous Silicon-Based Optical Interferometric Biosensor," *Science Magazine*, vol. 278, pp. 840-843, Oct. 31, 1997.

De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.

Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.

Park, B. Hyle et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479.

Roth, Jonathan E. et al., "Simplified Method for Polarization-Sensitive Optical Coherence Tomography," *Optics Letters*, vol. 26, No. 14, Jul. 15, 2001, pp. 1069-1071.

Hitzenberger, Christopher K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.

Wong, Brian J.F. et al., "Optical Coherence Tomography of the Rat Cochlea," Journal of *Biomedical Optics*, vol. 5, No. 4, Oct. 2000, pp. 367-370.

Yao, Gang et al., "Propagation of Polarized Light in Turbid Media: Simulated Animation Sequences," *Optics Express*, vol. 7, No. 5, Aug. 28, 2000, pp. 198-203.

Wang, Xiao-Jun et al., "Characterization of Dentin and Enamel by Use of Optical Coherence Tomography," *Applied Optics*, vol. 38, No. 10, Apr. 1, 1999, pp. 2092-2096.

De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-302.

Ducros, Mathieu G. et al., "Polarization Sensitive Optical Coherence Tomography of the Rabbit Eye," *IEEE Journal of Selected Topics in Quantum Electronics*, vol. 5, No. 4, Jul./Aug. 1999, pp. 1159-1167.

Groner, Warren et al., "Orthogonal Polarization Spectral Imaging: a New Method for Study of the Microcirculation," *Nature Medicine Inc.*, vol. 5 No. 10, Oct. 1999, pp. 1209-1213.

De Boer, Johannes F. et al., "Polarization Effects in Optical Coherence Tomography of Various Viological Tissues," *IEEE Journal of Selected Topics in Quantum Electronics*, vol. 5, No. 4, Jul./Aug. 1999, pp. 1200-1204.

Yao, Gang et al., "Two-Dimensional Depth-Resolved Mueller Matrix Characterization of Biological Tissue by Optical Coherence Tomography," *Optics Letters*, Apr. 15, 1999, Vol. 24, No. 8, pp. 537-539.

Lu, Shih-Yau et al., "Homogeneous and Inhomogeneous Jones Matrices," *J. Opt. Soc. Am. A.*, vol. 11, No. 2, Feb. 1994, pp. 766-773.

Bickel, S. William et al., "Stokes Vectors, Mueller Matrices, and Polarized Scattered Light," *Am. J. Phys.*, vol. 53, No. 5, May 1985 pp. 468-478.

Bréhonnet, F. Le Roy et al., "Optical Media and Target Characterization by Mueller Matrix Decomposition," *J. Phys. D: Appl. Phys.* 29, 1996, pp. 34-38.

Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.

De Boer, Johannes F. et al., "Two-Dimensional Birefringence Imaging in Biological Tissue by Polarization-Sensitive Optical Coherence Tomography," *Optics Letters*, vol. 22, No. 12, Jun. 15, 1997, pp. 934-936.

De Boer, Johannes F. et al., "Imaging Thermally Damaged Tissue by Polarization Sensitive Optical Coherence Tomography," *Optics Express*, vol. 3, No. 6, Sep. 14, 1998, pp. 212-218.

Everett, M.J. et al., "Birefringence Characterization of Biological Tissue by Use of Optical Coherence Tomography," *Optics Letters*, vol. 23, No. 3, Feb. 1, 1998, pp. 228-230.

Hee, Michael R. et al., "Polarization-Sensitive Low-Coherence Reflectometer for Birefringence Characterization and Ranging," *J. Opt. Soc. Am. B.*, vol. 9, No. 6, Jun. 1992, pp. 903-908.

Barakat, Richard, "Statistics of the Stokes Parameters," *J. Opt. Soc. Am. B.*, vol. 4, No. 7, Jul. 1987, pp. 1256-1263.

Schmitt, J.M. et al., "Cross-Polarized Backscatter in Optical Coherence Tomography of Biological Tissue," *Optics Letters*, vol. 23, No. 13, Jul. 1, 1998, pp. 1060-1062.

Schoenenberger, Klaus et al., "Mapping of Birefringence and Thermal Damage in Tissue by use of Polarization-Sensitive Optical Coherence Tomography," *Applied Optics*, vol. 37, No. 25, Sep. 1, 1998, pp. 6026-6036.

Pierce, Mark C. et al., "Simultaneous Intensity, Birefringence, and Flow Measurements with High-Speed Fiber-Based Optical Coherence Tomography," *Optics Letters*, vol. 27, No. 17, Sep. 1, 2002, pp. 1534-1536.

De Boer, Johannes F. et al., "Review of Polarization Sensitive Optical Coherence Tomography and Stokes Vector Determination," *Journal of Biomedical Optics*, Jul. 2002, Vol. 7, No. 3, pp. 359-371.

Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.

Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.

Jiao, Shuliang et al., "Jones-Matrix Imaging of Biological Tissues with Quadruple-Channel Optical Coherence Tomography," *Journal of Biomedical Optics*, vol. 7, No. 3, Jul. 2002, pp. 350-358.

Kuranov, R.V. et al., "Complementary Use of Cross-Polarization and Standard OCT for Differential Diagnosis of Pathological Tissues," *Optics Express*, vol. 10, No. 15, Jul. 29, 2002, pp. 707-713.

Cense, Barry et al., "In Vivo Depth-Resolved Birefringence Measurements of the Human Retinal Nerve Fiber Layer by Polarization-Sensitive Optical Coherence Tomography," *Optics Letters*, vol. 27, No. 18, Sep. 15, 2002, pp. 1610-1612.

Ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," *Optics Letters*, vol. 27, No. 19, Oct. 1, 2002, pp. 1702-1704.

Tripathi, Renu et al., "Spectral Shaping for Non-Gaussian Source Spectra in Optical Coherence Tomography," *Optics Letters*, vol. 27, No. 6, Mar. 15, 2002, pp. 406-408.

Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002 pp. 1803-1805.

White, Brian R. et al., "In Vivo Dynamic Human Retinal Blood Flow Imaging Using Ultra-High-Speed Spectral Domain Optical Doppler Tomography," *Optics Express*, vol. 11, No. 25, Dec. 15, 2003, pp. 3490-3497.

De Boer, Johannes F. et al., "Improved Signal-to-Noise Ratio in Spectral-Domain Compared with Time-Domain Optical Coherence Tomography," *Optics Letters*, vol. 28, No. 21, Nov. 1, 2003, pp. 2067-2069.

Jiao, Shuliang et al., "Optical-Fiber-Based Mueller Optical Coherence Tomography," *Optics Letters*, vol. 28, No. 14, Jul. 15, 2003, pp. 1206-1208.

Jiao, Shuliang et al., "Contrast Mechanisms in Polarization-Sensitive Mueller-Matrix Optical Coherence Tomography and Application in Burn Imaging," *Applied Optics*, vol. 42, No. 25, Sep. 1, 2003, pp. 5191-5197.

Moreau, Julien et al., "Full-Field Birefringence Imaging by Thermal-Light Polarization-Sensitive Optical Coherence Tomography. I. Theory," *Applied Optics*, vol. 42, No. 19, Jul. 1, 2003, pp. 3800-3810.

Moreau, Julien et al., "Full-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.

Morgan, Stephen P. et al., "Surface-Reflection Elimination in Polarization Imaging of Superficial Tissue," *Optics Letters*, vol. 28, No. 2, Jan. 15, 2003, pp. 114-116.

Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.

Park, B. Hyle et al., "Real-Time Multi-Functional Optical Coherence Tomography," *Optics Express*, vol. 11, No. 7, Apr. 7, 2003, pp. 782-793.

Shribak, Michael et al., "Techniques for Fast and Sensitive Measurements of Two-Dimensional Birefringence Distributions," *Applied Optics*, vol. 42, No. 16, Jun. 1, 2003, pp. 3009-3017.

Somervell, A.R.D. et al., "Direct Measurement of Fringe Amplitude and Phase Using a Heterodyne Interferometer Operating in Broadband Light," *Elsevier, Optics Communications*, Oct. 2003.

Stifter, D. et al., "Polarisation-Sensitive Optical Coherence Tomography for Material Characterisation and Strain-Field Mapping," Applied Physics A 76, Materials Science & Processing, Jan. 2003, pp. 947-951.

Davé, Digant P. et al., "Polarization-Maintaining Fiber-Based Optical Low-Coherence Reflectometer for Characterization and Ranging of Birefringence," *Optics Letters*, vol. 28, No. 19, Oct. 1, 2003, pp. 1775-1777.

Yang, Ying et al., "Observations of Birefringence in Tissues from Optic-Fibre-Based Optical Coherence Tomography," *Measurement Science and Technology*, Nov. 2002, pp. 41-42.

Yun, S.H. et al., "High-Speed Optical Frequency-Domain Imaging," *Optics Express*, vol. 11, No. 22, Nov. 3, 2003, pp. 2953-2963.

Yun, S.H. et al., "High-Speed Spectral-Domain Optical Coherence Tomography at 1.3 μm Wavelength," *Optics Express*, vol. 11, No. 26, Dec. 29, 2003, pp. 3598-3604.

Zhang, Jun et al., "Determination of Birefringence and Absolute Optic Axis Orientation Using Polarization-Sensitive Optical Coherence Tomography with PM Fibers," *Optics Express*, vol. 11, No. 24, Dec. 1, 2003, pp. 3262-3270.

Pircher, Michael et al., "Three Dimensional Polarization Sensitive OCT of Human Skin In Vivo," 2004, *Optical Society of America*.

Götzinger, Erich et al., "Measurement and Imaging of Birefringent Properties of the Human Cornea with Phase-Resolved, Polarization-Sensitive Optical Coherence Tomography," *Journal of Biomedical Optics*, vol. 9, No. 1, Jan./Feb. 2004, pp. 94-102.

Guo, Shuguang et al., "Depth-Resolved Birefringence and Differential Optical Axis Orientation Measurements with Finer-based Polarization-Sensitive Optical Coherence Tomography," *Optics Letters*, vol. 29, No. 17, Sep. 1, 2004, pp. 2025-2027.

Huang, Xiang-Run et al.,"Variation of Peripapillary Retinal Nerve Fiber Layer Birefringence in Normal Human Subjects," *Investigative Ophthalmology & Visual Science*, vol. 45, No. 9, Sep. 2004, pp. 3073-3080.

Matcher, Stephen J. et al., "The Collagen Structure of Bovine Intervertebral Disc Studied Using Polarization-Sensitive Optical Coherence Tomography," *Physics in Medicine and Biology*, 2004, pp. 1295-1306.

Nassif, Nader et al., "In Vivo Human Retinal Imaging by Ultrahigh-Speed Spectral Domain Optical Coherence Tomography," *Optics Letters*, vol. 29, No. 5, Mar. 1, 2004, pp. 480-482.

Nassif, N. A. et al., "In Vivo High-Resolution Video-Rate Spectral-Domain Optical Coherence Tomography of the Human Retina and Optic Nerve," *Optics Express*, vol. 12, No. 3, Feb. 9, 2004, pp. 367-376.

Park, B. Hyle et al., Comment on "Optical-Fiber-Based Mueller Optical Coherence Tomography," *Optics Letters*, vol. 29, No. 24, Dec. 15, 2004, pp. 2873-2874.

Park, B. Hyle et al., "Jones Matrix Analysis for a Polarization-Sensitive Optical Coherence Tomography System Using Fiber-Optic Components," *Optics Letters*, vol. 29, No. 21, Nov. 1, 2004, pp. 2512-2514.

Pierce, Mark C. et al., "Collagen Denaturation can be Quantified in Burned Human Skin Using Polarization-Sensitive Optical Coherence Tomography," *Elsevier, Burns*, 2004, pp. 511-517.

Pierce, Mark C. et al., "Advances in Optical Coherence Tomography Imaging for Dermatology," *The Society for Investigative Dermatology, Inc.* 2004, pp. 458-463.

Pierce, Mark C. et al., "Birefringence Measurements in Human Skin Using Polarization-Sensitive Optical Coherence Tomography," *Journal of Biomedical Optics*, vol. 9, No. 2, Mar./Apr. 2004, pp. 287-291.

Cense, Barry et al., "In Vivo Birefringence and Thickness Measurements of the Human Retinal Nerve Fiber Layer Using Polarization-Sensitive Optical Coherence Tomography," *Journal of Biomedical Optics*, vol. 9, No. 1, Jan./Feb. 2004, pp. 121-125.

Pircher, Michael et al., "Imaging Of Polarization Properties of Human Retina in Vivo with Phase Resolved Transversal PS-OCT," *Optics Express*, vol. 12, No. 24, Nov. 29, 2004 pp. 5940-5951.

Pircher, Michael et al., "Transversal Phase Resolved Polarization Sensitive Optical Coherence Tomography," *Physics in Medicine & Biology*, 2004, pp. 1257-1263.

Srinivas, Shyam M. et al., "Determination of Burn Depth by Polarization-Sensitive Optical Coherence Tomography," *Journal of Biomedical Optics*, vol. 9, No. 1, Jan./Feb. 2004, pp. 207-212.

Strasswimmer, John et al., "Polarization-Sensitive Optical Coherence Tomography of Invasive Basal Cell Carcinoma," *Journal of Biomedical Optics*, vol. 9, No. 2, Mar./Apr. 2004, pp. 292-298.

Todorovič, Milošet al., "Determination of Local Polarization Properties of Biological Samples in the Presence of Diattenuation by use of Mueller Optical Coherence Tomography," *Optics Letters*, vol. 29, No. 20, Oct. 15, 2004, pp. 2402-2404.

Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.

Acioli, L. H., M. Ulman, et al. (1991). "Femtosecond Temporal Encoding in Barium-Titanate." *Optics Letters* 16(24): 1984-1986.

Aigouy, L., A. Lahrech, et al. (1999). "Polarization effects in apertureless scanning near-field optical microscopy: an experimental study." *Optics Letters* 24(4): 187-189.

Akiba, M., K. P. Chan, et al. (2003). "Full-field optical coherence tomography by two-dimensional heterodyne detection with a pair of CCD cameras." *Optics Letters* 28(10): 816-818.

Akkin, T., D. P. Dave, et al. (2004). "Detection of neural activity using phase-sensitive optical low-coherence reflectometry." *Optics Express* 12(11): 2377-2386.

Akkin, T., D. P. Dave, et al. (2003). "Surface analysis using phase sensitive optical low coherence reflectometry." *Lasers in Surgery and Medicine*: 4-4.

Akkin, T., D. P. Dave, et al. (2003). "Imaging tissue response to electrical and photothermal stimulation with nanometer sensitivity." *Lasers in Surgery and Medicine* 33(4): 219-225.

Akkin, T., T. E. Milner, et al. (2002). "Phase-sensitive measurement of birefringence change as an indication of neural functionality and diseases." *Lasers in Surgery and Medicine*: 6-6.

Andretzky, P., Lindner, M.W., Herrmann, J.M., Schultz, A., Konzog, M., Kiesewetter, F., Haeusler, G. (1999). "Optical coherence tomography by 'spectral radar': Dynamic range estimation and in vivo measurements of skin." *Proceedings of SPIE—The International Society for Optical Engineering* 3567: pp. 78-87.

Antcliff, R. J., T. J. ffytche, et al. (2000). "Optical coherence tomography of melanocytoma." *American Journal of Ophthalmology* 130(6): 845-7.

Antcliff, R. J., M. R. Stanford, et al. (2000). "Comparison between optical coherence tomography and fundus fluorescein angiography for the detection of cystoid macular edema in patients with uveitis." *Ophthalmology* 107(3): 593-9.

Anvari, B., T. E. Milner, et al. (1995). "Selective Cooling of Biological Tissues—Application for Thermally Mediated Therapeutic Procedures." *Physics in Medicine and Biology* 40(2): 241-252.

Anvari, B., B. S. Tanenbaum, et al. (1995). "A Theoretical-Study of the Thermal Response of Skin to Cryogen Spray Cooling and Pulsed-Laser Irradiation—Implications for Treatment of Port-Wine Stain Birthmarks." *Physics in Medicine and Biology* 40(9): 1451-1465.

Arend, O., M. Ruffer, et al. (2000). "Macular circulation in patients with diabetes mellitus with and without arterial hypertension." *British Journal of Ophthalmology* 84(12): 1392-1396.

Arimoto, H. and Y. Ohtsuka (1997). "Measurements of the complex degree of spectral coherence by use of a wave-front-folded interferometer." *Optics Letters* 22(13): 958-960.

Azzolini, C., F. Patelli, et al. (2001). "Correlation between optical coherence tomography data and biomicroscopic interpretation of idiopathic macular hole." *American Journal of Ophthalmology.* 132(3): 348-55.

Baba, T., K. Ohno-Matsui, et al. (2002). "Optical coherence tomography of choroidal neovascularization in high myopia." *Acta Ophthalmoloqica Scandinavica* 80(1): 82-7.

Bail, M. A. H., Gerd; Herrmann, Juergen M.; Lindner, Michael W.; Ringler, R. (1996). "Optical coherence tomography with the "spectral radar": fast optical analysis in volume scatterers by short-coherence interferometry." *Proc. SPIE* , 2925: p. 298-303.

Baney, D. M. And W. V. Sorin (1993). "Extended-Range Optical Low-Coherence Reflectometry Using a Recirculating Delay Technique." *Ieee Photonics Technology Letters* 5(9): 1109-1112.

Baney, D. M., B. Szafraniec, et al. (2002). "Coherent optical spectrum analyzer." *Ieee Photonics Technology Letters* 14(3): 355-357.

Barakat, R. (1981). "Bilinear Constraints between Elements of the 4by4 Mueller-Jones Transfer-Matrix of Polarization Theory." *Optics Communications* 38(3): 159-161.

Barakat, R. (1993). "Analytic Proofs of the Arago-Fresnel Laws for the Interference of Polarized-Light." *Journal of the Optical Society of America a-Optics Image Science and Vision* 10(1): 180-185.

Barbastathis, G. and D. J. Brady (1999). "Multidimensional tomographic imaging using volume holography." *Proceedings of the Ieee* 87(12): 2098-2120.

Bardal, S., A. Kamal, et al. (1992). "Photoinduced Birefringence in Optical Fibers—a Comparative-Study of Low-Birefringence and High-Birefringence Fibers." *Optics Letters* 17(6): 411-413.

Barsky, S. H., S. Rosen, et al. (1980). "Nature and Evolution of Port Wine Stains—Computer-Assisted Study." *Journal of Investigative Dermatology* 74(3): 154-157.

Barton, J. K., J. A. Izatt, et al. (1999). "Three-dimensional reconstruction of blood vessels from in vivo color Doppler optical coherence tomography images." *Dermatology* 198(4): 355-361.

Barton, J. K., A. Rollins, et al. (2001). "Photothermal coagulation of blood vessels: a comparison of high-speed optical coherence tomography and numerical modelling." *Physics in Medicine and Biology* 46.

Barton, J. K., A. J. Welch, et al. (1998). "Investigating pulsed dye laser-blood vessel interaction with color Doppler optical coherence tomography." *Optics Express* 3.

Bashkansky, M., M. D. Duncan, et al. (1997). "Subsurface defect detection in ceramics by high-speed high-resolution optical coherent tomography." *Optics Letters* 22 (1): 61-63.

Bashkansky, M. and J. Reintjes (2000). "Statistics and reduction of speckle in optical coherence tomography." *Optics Letters* 25(8): 545-547.

Baumgartner, A., S. Dichtl, et al. (2000). "Polarization-sensitive optical coherence tomography of dental structures." *Caries Research* 34(1): 59-69.

Baumgartner, A., C. K. Hitzenberger, et al. (2000). "Resolution-improved dual-beam and standard optical coherence tomography: a comparison." *Graefes Archive for Clinical and Experimental Ophthalmology* 238(5): 385-392.

Baumgartner, A., C. K. Hitzenberger, et al. (1998). "Signal and resolution enhancements in dual beam optical coherence tomography of the human eye." *Journal of Biomedical Optics* 3(1): 45-54.

Beaurepaire, E., P. Gleyzes, et at. (1998). *Optical coherence microscopy for the in-depth study of biological structures: System based on a parallel detection scheme*, Proceedings of SPIE—The International Society for Optical Engineering.

Beaurepaire, E., L. Moreaux, et al. (1999). "Combined scanning optical coherence and two-photon-excited fluorescence microscopy." *Optics Letters* 24(14): 969-971.

Bechara, F. G., T. Gambichler, et al. (2004). "Histomorphologic correlation with routine histology and optical coherence tomography." *Skin Research and Technology* 10 (3): 169-173.

Bechmann, M., M. J. Thiel, et al. (2000). "Central corneal thickness determined with optical coherence tomography in various types of glaucoma. [see comments]." *British Journal of Ophthalmology* 84(11): 1233-7.

Bek, T. and M. Kandi (2000). "Quantitative anomaloscopy and optical coherence tomography scanning in central serous chorioretinopathy." *Acta Ophthalmologica Scandinavica* 78(6): 632-7.

Benoit, A. M., K. Naoun, et al. (2001). "Linear dichroism of the retinal nerve fiber layer expressed with Mueller matrices." *Applied Optics* 40(4): 565-569.

Bicout, D., C. Brosseau, et al. (1994). "Depolarization of Multiply Scattered Waves by Spherical Diffusers—Influence of the Size Parameter." *Physical Review* E 49(2): 1767-1770.

Blanchot, L., M. Lebec, et al. (1997). *Low-coherence in depth microscopy for biological tissues imaging: Design of a real time control system*. Proceedings of SPIE—The International Society for Optical Engineering.

Blumenthal, E. Z. and R. N. Weinreb (2001). "Assessment of the retinal nerve fiber layer in clinical trials of glaucoma neuroprotection. [Review] [36 refs]." *Survey of Ophthalmology* 45(Suppl 3): S305-12; discussion S332-4.

Blumenthal, E. Z., J. M. Williams, et al. (2000). "Reproducibility of nerve fiber layer thickness measurements by use of optical coherence tomography." *Ophthalmology* 107(12): 2278-82.

Boppart, S. A., B. E. Bouma, et al. (1996). "Imaging developing neural morphology using optical coherence tomography." *Journal of Neuroscience Methods* 70.

Boppart, S. A., B. E. Bouma, et al. (1997). "Forward-imaging instruments for optical coherence tomography." *Optics Letters* 22.

Boppart, S. A., B. E. Bouma, et al. (1998). "Intraoperative assessment of microsurgery with three-dimensional optical coherence tomography." *Radiology* 208: 81-86.

Boppart, S. A., J. Herrmann, et al. (1999). "High-resolution optical coherence tomography-guided laser ablation of surgical tissue." *Journal of Surgical Research* 82(2): 275-84.

Bouma, B. E. and J. G. Fujimoto (1996). "Compact Kerr-lens mode-locked resonators." *Optics Letters* 21. 134-136.

Bouma, B. E., L. E. Nelson, et al. (1998). "Optical coherence tomographic imaging of human tissue at 1.55 mu m and 1.81 mu m using Er and Tm-doped fiber sources." *Journal of Biomedical Optics* 3. 76-79.

Bouma, B. E., M. Ramaswamy-Paye, et al. (1997). "Compact resonator designs for mode-locked solid-state lasers." *Applied Physics B (Lasers and Optics)* B65. 213-220.

Bouma, B. E. and G. J. Tearney (2002). "Clinical imaging with optical coherence tomography." *Academic Radiology* 9(8): 942-953.

Bouma, B. E., G. J. Tearney, et al. (1996). "Self-phase-modulated Kerr-lens mode-locked Cr:forsterite laser source for optical coherence tomography." *Optics Letters* 21(22): 1839.

Bouma, B. E., G. J. Tearney, et al. (2000). "High-resolution imaging of the human esophagus and stomach in vivo using optical coherence tomography." *Gastrointestinal Endoscopy* 51(4): 467-474.

Bouma, B. E., G. J. Tearney, et al. (2003). "Evaluation of intracoronary stenting by intravascular optical coherence tomography." *Heart* 89(3): 317-320.

Bourquin, S., V. Monterosso, et al. (2000). "Video-rate optical low-coherence reflectometry based on a linear smart detector array." *Optics Letters* 25(2): 102-104.

Bourquin, S., P. Seitz, et al. (2001). "Optical coherence topography based on a two-dimensional smart detector array." *Optics Letters* 26(8): 512-514.

Bouzid, A., M. A. G. Abushagur, et al. (1995). "Fiber-optic four-detector polarimeter." *Optics Communications* 118(3-4): 329-334.

Bowd, C., R. N. Weinreb, et al. (2000). "The retinal nerve fiber layer thickness in ocular hypertensive, normal, and glaucomatous eyes with optical coherence tomography." *Archives of Ophthalmology* 118(1): 22-6.

Bowd, C., L. M. Zangwill, et al. (2001). "Detecting early glaucoma by assessment of retinal nerve fiber layer thickness and visual function." *Investigative Ophthalmology & Visual Science* 42(9): 1993-2003.

Bowd, C., L. M. Zangwill, et al. (2002). "Imaging of the optic disc and retinal nerve fiber layer: the effects of age, optic disc area, refractive error, and gender." *Journal of the Optical Society of America, A, Optics, Image Science, & Vision* 19(1): 197-207.

Brand, S., J. M. Poneros, et al. (2000). "Optical coherence tomography in the gastrointestinal tract." *Endoscopy* 32(10): 796-803.

Brezinski, M. E. and J. G. Fujimoto (1999). "Optical coherence tomography: high-resolution imaging in nontransparent tissue." *IEEE Journal of Selected Topics in Quantum Electronics* 5(4): 1185-1192.

Brezinski, M. E., G. J. Tearney, et al. (1996). "Imaging of coronary artery microstructure (in vitro) with optical coherence tomography." *American Journal of Cardiology* 77 (1): 92-93.

Brezinski, M. E., G. J. Tearney, et al. (1996). "Optical coherence tomography for optical biopsy—Properties and demonstration of vascular pathology." *Circulation* 93(6): 1206-1213.

Brezinski, M. E., G. J. Tearney, et al. (1997). "Assessing atherosclerotic plaque morphology: Comparison of optical coherence tomography and high frequency intravascular ultrasound." *Heart* 77(5): 397-403.

Brink, H. B. K. and G. J. Vanblokland (1988). "Birefringence of the Human Foveal Area Assessed Invivo with Mueller-Matrix Ellipsometry." *Journal of the Optical Society of America a-Optics Image Science and Vison* 5(1): 49-57.

Brosseau, C. and D. Bicout (1994). "Entropy Production in Multiple-Scattering of Light by a Spatially Random Medium." *Physical Review E* 50(6): 4997-5005.

Burgoyne, C. F., D. E. Mercante, et al. (2002). "Change detection in regional and volumetric disc parameters using longitudinal confocal scanning laser tomography." *Ophthalmology* 109(3): 455-66.

Candido, R. and T. J. Allen (2002). "Haemodynamics in microvascular complications in type 1 diabetes." *Diabetes-Metabolism Research and Reviews* 18(4): 286-304.

Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.

Cense, B., N. Nassif, et al. (2004). "Ultrahigh-Resolution High-Speed Retinal Imaging Using Spectral-Domain Optical Coherence Tomography." *Optics Express* 12(11): 2435-2447.

Chance, B., J. S. Leigh, et al. (1988). "Comparison of Time-Resolved and Time-Unresolved Measurements of Deoxyhemoglobin in Brain." *Proceedings of the National Academy of Sciences of the United States of America* 85(14): 4971-4975.

Chang, E. P., D. A. Keedy, et al. (1974). "Ultrastructures of Rabbit Corneal Stroma—Mapping of Optical and Morphological Anisotropies." *Biochimica Et Biophysica Acta* 343(3): 615-626.

Chartier, T., A. Hideur, et al. (2001). "Measurement of the elliptical birefringence of single-mode optical fibers." *Applied Optics* 40(30): 5343-5353.

Chauhan, B. C., J. W. Blanchard, et al. (2000). "Technique for Detecting Serial Topographic Changes in the Optic Disc and Peripapillary Retina Using Scanning Laser Tomograph." *Invest Ophthalmol Vis Sci* 41: 775-782.

Chen, Z. P., T. E. Milner, et al. (1997). "Optical Doppler tomographic imaging of fluid flow velocity in highly scattering media." *Optics Letters* 22(1): 64-66.

Chen, Z. P., T. E. Milner, et al. (1997). "Noninvasive imaging of in vivo blood flow velocity using optical Doppler tomography." *Optics Letters* 22(14): 1119-1121.

Chen, Z. P., Y. H. Zhao, et al. (1999). "Optical Doppler tomography." *Ieee Journal of Selected Topics in Quantum Electronics* 5(4): 1134-1142.

Cheong, W. F., S. A. Prahl, et al. (1990). "A Review of the Optical-Properties of Biological Tissues." *Ieee Journal of Quantum Electronics* 26(12): 2166-2185.

Chernikov, S. V., Y. Zhu, et al. (1997). "Supercontinuum self-Q-switched ytterbium fiber laser." *Optics Letters* 22(5): 298-300.

Cho, S. H., B. E. Bouma, et al. (1999). "Low-repetition-rate high-peak-power Kerr-lens mode-locked Ti:Al/sub 2/0/sub 3/ laser with a multiple-pass cavity." *Optics Letters* 24(6): 417-419.

Choma, M. A., M. V. Sarunic, et al. (2003). "Sensitivity advantage of swept source and Fourier domain optical coherence tomography." *Optics Express* 11(18): 2183-2189.

Choma, M. A., C. H. Yang, et al. (2003). "Instantaneous quadrature low-coherence interferometry with 3×3 fiber-optic couplers." *Optics Letters* 28(22): 2162-2164.

Choplin, N. T. and D. C. Lundy (2001). "The sensitivity and specificity of scanning laser polarimetry in the detection of glaucoma in a clinical setting." *Ophthalmology* 108 (5): 899-904.

Christens Barry, W. A., W. J. Green, et al. (1996). "Spatial mapping of polarized light transmission in the central rabbit cornea." *Experimental Eye Research* 62(6): 651-662.

Chvapil, M., D. P. Speer, et al. (1984). "Identification of the depth of burn injury by collagen stainability." *Plastic & Reconstructive Surgery* 73(3): 438-41.

Cioffi, G. A. (2001). "Three common assumptions about ocular blood flow and glaucoma." *Survey of Ophthalmology* 45: S325-S331.

Coleman, A. L. (1999). "Glaucoma." *Lancet* 354(9192): 1803-10.

Collaborative Normal-Tension Glaucoma Study Group (1998). "Comparison of Glaucomatous Progression Between Untreated Patients With Normal Tension Glaucoma and Patients with Therapeutically Reduced Intraocular Pressures." *Am J Ophthalmol* 126: 487-97.

Collaborative Normal-Tension Glaucoma Study Group (1998). "The effectiveness of intraocular pressure reduction in the treatment of normal-tension glaucoma." *Am J Ophthalmol* 126: 498-505.

Collaborative Normal-Tension Glaucoma Study Group (2001). "Natural History of Normal-Tension Glaucoma." *Ophthalmology* 108: 247-253.

Colston, B. W., M. J. Everett, et al. (1998). "Imaging of hard- and soft-tissue structure in the oral cavity by optical coherence tomography." *Applied Optics* 37(16): 3582-3585.

Colston, B. W., U. S. Sathyam, et al. (1998). "Dental OCT." *Optics Express* 3(6): 230-238.

Congdon, N. G., D. S. Friedman, et al. (2003). "Important causes of visual impairment in the world today." *Jama-Journal of the American Medical Association* 290(15): 2057-2060.

Cregan, R. F., B. J. Mangan, et al. (1999). "Single-mode photonic band gap guidance of light in air." *Science* 285(5433): 1537-1539.

DalMolin, M., A. Galtarossa, et al. (1997). "Experimental investigation of linear polarization in high-birefringence single-mode fibers." *Applied Optics* 36(12): 2526-2528.

Danielson, B. L. and C. D. Whittenberg (1987). "Guided-Wave Reflectometry with Micrometer Resolution." *Applied Optics* 26(14): 2836-2842.

Dave, D. P. and T. E. Milner (2000). "Doppler-angle measurement in highly scattering media." *Optics Letters* 25(20): 1523-1525.

de Boer, J. F., T. E. Milner, et al. (1998). *Two dimensional birefringence imaging in biological tissue using phase and polarization sensitive optical coherence tomography.* Trends in Optics and Photonics (TOPS): Advances in Optical Imaging and Photon Migration, Orlando, USA, Optical Society of America, Washington, DC 1998.

de Boer, J. F., C. E. Saxer, et al. (2001). "Stable carrier generation and phase-resolved digital data processing in optical coherence tomography." *Applied Optics* 40(31): 5787-5790.

Degroot, P. and L. Deck (1993). "3-Dimensional Imaging by Sub-Nyquist Sampling of White-Light Interferograms." *Optics Letters* 18(17): 1462-1464.

Denk, W., J. H. Strickler, et al. (1990). "2-Photon Laser Scanning Fluorescence Microscopy." *Science* 248(4951): 73-76.

Descour, M. R., A. H. O. Karkkainen, et al. (2002). "Toward the development of miniaturized Imaging systems for detection of precancer." *Ieee Journal of Quantum Electronics* 38(2): 122-130.

Dettwiller, L. (1997). "Polarization state interference: A general investigation." *Pure and Applied Optics* 6(1): 41-53.

DiCarlo, C. D., W. P. Roach, et al. (1999). "Comparison of optical coherence tomography imaging of cataracts with histopathology." *Journal of Biomedical Optics* 4.

Ding, Z., Y. Zhao, et al. (2002). "Real-time phase-resolved optical coherence tomography and optical Doppler tomography." *Optics Express* 10(5): 236-245.

Dobrin, P. B. (1996). "Effect of histologic preparation on the cross-sectional area of arterial rings." *Journal of Surgical Research* 61(2): 413-5.

Donohue, D. J., B. J. Stoyanov, et al. (1995). "Numerical Modeling of the Corneas Lamellar Structure and Birefringence Properties." *Journal of the Optical Society of America a-Optics Image Science and Vision* 12(7): 1425-1438.

Doornbos, R. M. P., R. Lang, et al. (1999). "The determination of in vivo human tissue optical properties and absolute chromophore concentrations using spatially resolved steady-state diffuse reflectance spectroscopy." *Physics in Medicine and Biology* 44(4): 967-981.

Drexler, W., A. Baumgartner, et al. (1997). "Biometric investigation of changes in the anterior eye segment during accommodation." *Vision Research* 37(19): 2789-2800.

Drexler, W., A. Baumgartner, et al. (1997). "Submicrometer precision biometry of the anterior segment of the human eye." *Investigative Ophthalmology & Visual Science* 38(7): 1304-1313.

Drexler, W., A. Baumgartner, et al. (1998). "Dual beam optical coherence tomography: signal identification for ophthalmologic diagnosis." *Journal of Biomedical Optics* 3 (1): 55-65.

Drexler, W., O. Findl, et al. (1998). "Partial coherence interferometry: A novel approach to biometry in cataract surgery." *American Journal of Ophthalmology* 126(4): 524-534.

Drexler, W., O. Findl, et al. (1997). "Clinical feasibility of dual beam optical coherence topography and tomography for ophthalmologic diagnosis." *Investigative Ophthalmology & Visual Science* 38(4): 1038-1038.

Drexler, W., C. K. Hitzenberger, et al. (1998). "Investigation of dispersion effects in ocular media by multiple wavelength partial coherence interferometry." *Experimental Eye Research* 66(1): 25-33.

Drexler, W., C. K. Hitzenberger, et al. (1996). "(Sub)micrometer precision biometry of the human eye by optical coherence tomography and topography." *Investigative Ophthalmology & Visual Science* 37(3): 4374-4374.

Drexler, W., C. K. Hitzenberger, et al. (1995). "Measurement of the Thickness of Fundus Layers by Partial Coherence Tomography." *Optical Engineering* 34(3): 701-710.

Drexler, W., U. Morgner, et al. (2001). "Ultrahigh-resolution ophthalmic optical coherence tomography." *Nature Medicine* 7(4): 502-507.

Drexler, W., U. Morgner, et al. (2001). "Ultrahigh-resolution ophthalmic optical coherence tomography. [erratum appears in Nat Med May 2001;7(5):636.]." *Nature Medicine* 7(4): 502-7.

Drexler, W., H. Sattmann, et al. (2003). "Enhanced visualization of macular pathology with the use of ultrahigh-resolution optical coherence tomography." *Archives of Ophthalmology* 121(5): 695-706.

Drexler, W., D. Stamper, et al. (2001). "Correlation of collagen organization with polarization sensitive imaging of in vitro cartilage: implications for osteoarthritis." *Journal of Rheumatology* 28(6): 1311-8.

Droog, E. J., W. Steenbergen, et al. (2001). "Measurement of depth of burns by laser Doppler perfusion imaging." *Burns* 27(6): 561-8.

Dubois, A., K. Grieve, et al. (2004). "Ultrahigh-resolution full-field optical coherence tomography." *Applied Optics* 43(14): 2874-2883.

Dubois, A., L. Vabre, et al. (2002). "High-resolution full-field optical coherence tomography with a Linnik microscope." *Applied Optics* 41(4): 805-812.

Ducros, M., M. Laubscher, et al. (2002). "Parallel optical coherence tomography in scattering samples using a two-dimensional smart-pixel detector array." *Optics Communications* 202(1-3): 29-35.

Ducros, M. G., J. D. Marsack, et al. (2001). "Primate retina imaging with polarization-sensitive optical coherence tomography." *Journal of the Optical Society of America a-Optics Image Science and Vision* 18(12): 2945-2956.

Duncan, A., J. H. Meek, et al. (1995). "Optical Pathlength Measurements on Adult Head, Calf and Forearm and the Head of the Newborn-Infant Using Phase-Resolved Optical Spectroscopy." *Physics in Medicine and Biology* 40(2): 295-304.

Eigensee, A., G. Haeusler, et al. (1996). "New method of short-coherence interferometry in human skin (in vivo) and in solid volume scatterers." *Proceedings of SPIE—The International Society for Optical Engineerinq* 2925: 169-178.

Eisenbeiss, W., J. Marotz, et al. (1999). "Reflection-optical multispectral imaging method for objective determination of burn depth." *Burns* 25(8): 697-704.

Elbaum, M., M. King, et al. (1972). "Wavelength-Diversity Technique for Reduction of Speckle Size." *Journal of the Optical Society of America* 62(5): 732-&.

Ervin, J. C., H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.

Essenpreis, M., C. E. Elwell, et al. (1993). "Spectral Dependence of Temporal Point Spread Functions in Human Tissues." *Applied Optics* 32(4): 418-425.

Eun, H. C. (1995). "Evaluation of skin blood flow by laser Doppler flowmetry. [Review] [151 refs]." *Clinics in Dermatology* 13(4): 337-47.

Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.

Feldchtein, F. I., G. V. Gelikonov, et al. (1998). "In vivo OCT imaging of hard and soft tissue of the oral cavity." *Optics Express* 3(6): 239-250.

Feldchtein, F. I., G. V. Gelikonov, et al. (1998). "Endoscopic applications of optical coherence tomography." *Optics Express* 3(6): 257-270.

Fercher, A. F., W. Drexler, et al. (1997). "Optical ocular tomography." *Neuro-Ophthalmology* 18(2): 39-49.

Fercher, A. F., W. Drexler, et al. (1994). *Measurement of optical distances by optical spectrum modulation.* Proceedings of SPIE—The International Society for Optical Engineering.

Fercher, A. F., W. Drexler, et al. (2003). "Optical coherence tomography—principles and applications." *Reports on Progress in Physics* 66(2): 239-303.

Fercher, A. F., C. Hitzenberger, et al. (1991). "Measurement of Intraocular Optical Distances Using Partially Coherent Laser-Light." *Journal of Modern Optics* 38(7): 1327-1333.

Fercher, A. F., C. K. Hitzenberger, et al. (1996). *Ocular partial coherence interferometry.* Proceedings of SPIE—The International Society for Optical Engineering.

Fercher, A. F., C. K. Hitzenberger, et al. (1993). "In-Vivo Optical Coherence Tomography." *American Journal of Ophthalmology* 116(1): 113-115.

Fercher, A. F., C. K. Hitzenberger, et al. (1994). *In-vivo dual-beam optical coherence tomography.* Proceedings of SPIE—The International Society for Optical Engineering.

Fercher, A. F., C. K. Hitzenberger, et al. (1995). "Measurement of Intraocular Distances by Backscattering Spectral Interferometry." *Optics Communications* 117(1-2): 43-48.

Fercher, A. F., C. K. Hitzenberger, et al. (2000). "A thermal light source technique for optical coherence tomography." *Optics Communications* 185(1-3): 57-64.

Fercher, A. F., C. K. Hitzenberger, et al. (2001). "Numerical dispersion compensation for Partial Coherence Interferometry and Optical Coherence Tomography." *Optics Express* 9(12): 610-615.

Fercher, A. F., C. K. Hitzenberger, et al. (2002). "Dispersion compensation for optical coherence tomography depth- scan signals by a numerical technique." *Optics Communications* 204(1-6): 67-74.

Fercher, A. F., H. C. Li, et al. (1993). "Slit Lamp Laser-Doppler Interferometer." *Lasers in Surgery and Medicine* 13(4): 447-452.

Fercher, A. F., K. Mengedoht, et at. (1988). "Eye-Length Measurement by Interferometry with Partially Coherent-Light." *Optics Letters* 13(3): 186-188.

Ferro, P., M. Haelterman, et al. (1991). "All-Optical Polarization Switch with Long Low-Birefringence Fiber." *Electronics Letters* 27(16): 1407-1408.

Fetterman, M. R., D. Goswami, et al. (1998). "Ultrafast pulse shaping: amplification and characterization." *Optics Express* 3(10): 366-375.

Findl, O., W. Drexler, et al. (2001). "Improved prediction of intraocular lens power using partial coherence interferometry." *Journal of Cataract and Refractive Surgery* 27 (6): 861-867.

Fork, R. L., C. H. B. Cruz, et al. (1987). "Compression of Optical Pulses to 6 Femtoseconds by Using Cubic Phase Compensation." *Optics Letters* 12(7): 483-485.

Foschini, G. J. and C. D. Poole (1991). "Statistical-Theory of Polarization Dispersion in Single-Mode Fibers." *Journal of Lightwave Technology* 9(11): 1439-1456.

Francia, C., F. Bruyere, et al. (1998). "PMD second-order effects on pulse propagation in single-mode optical fibers." *Ieee Photonics Technology Letters* 10(12): 1739-1741.

Fried, D., R. E. Glena, et al. (1995). "Nature of Light-Scattering in Dental Enamel and Dentin at Visible and near-Infrared Wavelengths." *Applied Optics* 34(7): 1278-1285.

Fujimoto, J. G., M. E. Brezinski, et al. (1995). "Optical Biopsy and Imaging Using Optical Coherence Tomography." *Nature Medicine* 1(9): 970-972.

Fukasawa, A. and H. Iijima (2002). "Optical coherence tomography of choroidal osteoma." *American Journal of Ophthalmology* 133(3): 419-21.

Fymat, A. L. (1981). "High-Resolution Interferometric Spectrophotopolarimetry." *Optical Engineering* 20(1): 25-30.

Galtarossa, A., L. Palmieri, et al. (2000). "Statistical characterization of fiber random birefringence." *Optics Letters* 25(18): 1322-1324.

Galtarossa, A., L. Palmieri, et al. (2000). "Measurements of beat length and perturbation length in long single-mode fibers." *Optics Letters* 25(6): 384-386.

Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.

Garcia, N. and M. Nieto-Vesperinas (2002). "Left-handed materials do not make a perfect lens." *Physical Review Letters* 88(20).

Gelikonov, V. M., G. V. Gelikonov, et al. (1995). "Coherent Optical Tomography of Microscopic Inhomogeneities in Biological Tissues." *Jetp Letters* 61(2): 158-162.

George, N. and A. Jain (1973). "Speckle Reduction Using Multiple Tones of Illumination." *Applied Optics* 12(6): 1202-1212.

Gibson, G. N., R. Klank, et al. (1996). "Electro-optically cavity-dumped ultrashort-pulse Ti:sapphire oscillator." *Optics Letters* 21(14): 1055.

Gil, J. J. (2000). "Characteristic properties of Mueller matrices." *Journal of the Optical Society of America a-Optics Image Science and Vision* 17(2): 328-334.

Gil, J. J. and E. Bernabeu (1987). "Obtainment of the Polarizing and Retardation Parameters of a Nondepolarizing Optical-System from the Polar Decomposition of Its Mueller Matrix." *Optik* 76(2): 67-71.

Gladkova, N. D., G. A. Petrova, et al. (2000). "In vivo optical coherence tomography imaging of human skin: norm and pathology." *Skin Research and Technology* 6 (1): 6-16.

Glaessl, A., A. G. Schreyer, et al. (2001). "Laser surgical planning with magnetic resonance imaging-based 3-dimensional reconstructions for intralesional Nd : YAG laser therapy of a venous malformation of the neck." *Archives of Dermatology* 137(10): 1331-1335.

Gloesmann, M., B. Hermann, et al. (2003). "Histologic correlation of pig retina radial stratification with ultrahigh-resolution optical coherence tomography." *Investigative Ophthalmology & Visual Science* 44(4): 1696-1703.

Goldberg, L. and D. Mehuys (1994). "High-Power Superluminescent Diode Source." *Electronics Letters* 30(20): 1682-1684.

Goldsmith, J. A., Y. Li, et al. (2005). "Anterior chamber width measurement by high speed optical coherence tomography." *Ophthalmology* 112(2): 238-244.

Goldstein, L. E., J. A. Muffat, et al. (2003). "Cytosolic beta-amyloid deposition and supranuclear cataracts in lenses from people with Alzheimer's disease." *Lancet* 361(9365): 1258-1265.

Golubovic, B., B. E. Bouma, et al. (1996). "Thin crystal, room-temperature Cr/sup 4 +/:forstefite laser using near-infrared pumping." *Optics Letters* 21(24): 1993-1995.

Gonzalez, S. and Z. Tannous (2002). "Real-time, in vivo confocal reflectance microscopy of basal cell carcinoma." *Journal of the American Academy of Dermatology* 47(6): 869-874.

Gordon, M. O. and M. A. Kass (1999). "The Ocular Hypertension Treatment Study: design and baseline description of the participants." *Archives of Ophthalmology* 117(5): 573-83.

Grayson, T. P., J. R. Torgerson, et al. (1994). "Observation of a Nonlocal Pancharatnam Phase-Shift in the Process of Induced Coherence without Induced Emission." *Physical Review* A 49(1): 626-628.

Greaney, M. J., D. C. Hoffman, et al. (2002). "Comparison of optic nerve imaging methods to distinguish normal eyes from those with glaucoma." *Investigative Ophthalmology & Visual Science* 43(1): 140-5.

Greenfield, D. S., H. Bagga, et al. (2003). "Macular thickness changes in glaucomatous optic neuropathy detected using optical coherence tomography." *Archives of Ophthalmology* 121(1): 41-46.

Greenfield, D. S., R. W. Knighton, et al. (2000). "Effect of corneal polarization axis on assessment of retinal nerve fiber layer thickness by scanning laser polarimetry." *American Journal of Ophthalmology* 129(6): 715-722.

Griffin, R. A., D. D. Sampson, et al. (1995). "Coherence Coding for Photonic Code-Division Multiple-Access Networks." *Journal of Lightwave Technology* 13(9): 1826-1837.

Guedes, V., J. S. Schuman, et al. (2003). "Optical coherence tomography measurement of macular and nerve fiber layer thickness in normal and glaucomatous human eyes." *Ophthalmology* 110(1): 177-189.

Gueugniaud, P. Y., H. Carsin, et al. (2000). "Current advances in the initial management of major thermal burns. [Review] [76 refs]." *Intensive Care Medicine* 26(7): 848-56.

Guido, S. and R. T. Tranquillo (1993). "A Methodology for the Systematic and Quantitative Study of Cell Contact Guidance in Oriented Collagen Gels—Correlation of Fibroblast Orientation and Gel Birefringence." *Journal of Cell Science* 105: 317-331.

Gurses-Ozden, R., H. Ishikawa, et al. (1999). "Increasing sampling density improves reproducibility of optical coherence tomography measurements." *Journal of Glaucoma* 8(4): 238-41.

Guzzi, R. (1998). "Scattering Theory from Homogeneous and Coated Spheres." 1-11.

Haberland, U. B., Vladimir; Schmitt, Hans J. (1996). "Optical coherent tomography of scattering media using electrically tunable near-infrared semiconductor laser." *Applied Optics* Draft Copy.

Haberland, U. R., Walter; Blazek, Vladimir; Schmitt, Hans J. (1995). "Investigation of highly scattering media using near-infrared continuous wave tunable semiconductor laser." *Proc. SPIE*, 2389: 503-512.

Hale, G. M. and M. R. Querry (1973). "Optical-Constants of Water in 200-Nm to 200-Mum Wavelength Region." *Applied Optics* 12(3): 555-563.

Hammer, D. X., R. D. Ferguson, et al. (2002). "Image stabilization for scanning laser ophthalmoscopy." *Optics Express* 10(26): 1542.

Hara, T., Y. Ooi, et al. (1989). "Transfer Characteristics of the Microchannel Spatial Light-Modulator." *Applied Optics* 28(22): 4781-4786.

Harland, C. C., S. G. Kale, et al. (2000). "Differentiation of common benign pigmented skin lesions from melanoma by high-resolution ultrasound." *British Journal of Dermatology* 143(2): 281-289.

Hartl, I., X. D. Li, et al. (2001). "Ultrahigh-resolution optical coherence tomography using continuum generation in an air-silica microstructure optical fiber." *Optics Letters* 26(9): 608-610.

Hassenstein, A., A. A. Bialasiewicz, et al. (2000). "Optical coherence tomography in uveitis patients." *American Journal of Ophthalmology* 130(5): 669-70.

Hattenhauer, M. G., D. H. Johnson, et al. (1998). "The probability of blindness from open-angle glaucoma. [see comments]." *Ophthalmology* 105(11): 2099-104.

Hausler, G., J. M. Herrmann, et al. (1996). "Observation of light propagation in volume scatterers with 10(11)-fold slow motion." *Optics Letters* 21(14): 1087-1089.

Hazebroek, H. F. and A. A. Holscher (1973). "Interferometric Ellipsometry." *Journal of Physics E-Scientific Instruments* 6(9): 822-826.

Hazebroek, H. F. and W. M. Visser (1983). "Automated Laser Interferometric Ellipsometry and Precision Reflectometry." *Journal of Physics E-Scientific Instruments* 16(7): 654-661.

He, Z. Y., N. Mukohzaka, et al. (1997). "Selective image extraction by synthesis of the coherence function using two-dimensional optical lock-in amplifier with microchannel spatial light modulator." *Ieee Photonics Technology Letters* 9(4): 514-516.

Hee, M. R., J. A. Izatt, et al. (1993). "Femtosecond Transillumination Optical Coherence Tomography." *Optics Letters* 18(12): 950-952.

Hee, M. R., J. A. Izatt, et al. (1995). "Optical coherence tomography of the human retina." *Archives of Ophthalmology* 113(3): 325-32.

Hee, M. R., C. A. Puliafito, et al. (1998). "Topography of diabetic macular edema with optical coherence tomography." *Ophthalmology* 105(2): 360-70.

Hee, M. R., C. A. Puliafito, et al. (1995). "Quantitative assessment of macular edema with optical coherence tomography." *Archives of Ophthalmology* 113(8): 1019-29.

Hellmuth, T. and M. Welle (1998). "Simultaneous measurement of dispersion, spectrum, and distance with a fourier transform spectrometer." *Journal of Biomedical Optics* 3(1): 7-11.

Hemenger, R. P. (1989). "Birefringence of a medium of tenuous parallel cylinders." *Applied Optics* 28(18): 4030-4034.

Henry, M. (1981). "Fresnel-Arago Laws for Interference in Polarized-Light—Demonstration Experiment." *American Journal of Physics* 49(7): 690-691.

Herz, P. R., Y. Chen, et al. (2004). "Micromotor endoscope catheter for in vivo, ultrahigh-resolution optical coherence tomography." *Optics Letters* 29(19): 2261-2263.

Hirakawa, H., H. Iijima, et al. (1999). "Optical coherence tomography of cystoid macular edema associated with retinitis pigmentosa." *American Journal of Ophthalmology* 128(2): 185-91.

Hitzenberger, C. K., A. Baumgartner, et al. (1994). "Interferometric Measurement of Corneal Thickness with Micrometer Precision." *American Journal of Ophthalmology* 118(4): 468-476.

Hitzenberger, C. K., A. Baumgartner, et al. (1999). "Dispersion effects in partial coherence interferometry: Implications for intraocular ranging." *Journal of Biomedical Optics* 4(1): 144-151.

Hitzenberger, C. K., A. Baumgartner, et al. (1998). "Dispersion induced multiple signal peak splitting in partial coherence interferometry." *Optics Communications* 154 (4): 179-185.

Hitzenberger, C. K., M. Danner, et al. (1999). "Measurement of the spatial coherence of superluminescent diodes." *Journal of Modern Optics* 46(12): 1763-1774.

Hitzenberger, C. K. and A. F. Fercher (1999). "Differential phase contrast in optical coherence tomography." *Optics Letters* 24(9): 622-624.

Hitzenberger, C. K., M. Sticker, et al. (2001). "Differential phase measurements in low-coherence interferometry without 2 pi ambiguity." *Optics Letters* 26(23): 1864-1866.

Hoeling, B. M., A. D. Fernandez, et al. (2000). "An optical coherence microscope for 3-dimensional imaging in developmental biology." *Optics Express* 6(7): 136-146.

Hoerauf, H., C. Scholz, et al. (2002). "Transscleral optical coherence tomography: a new imaging method for the anterior segment of the eye." *Archives of Ophthalmology* 120(6): 816-9.

Hoffmann, K., M. Happe, et al. (1998). "Optical coherence tomography (OCT) in dermatology." *Journal of Investigative Dermatology* 110(4): 583-583.

Hoh, S. T., D. S. Greenfield, et al. (2000). "Optical coherence tomography and scanning laser polarimetry in normal, ocular hypertensive, and glaucomatous eyes." *American Journal of Ophthalmology* 129(2): 129-35.

Hohenleutner, U., M. Hilbert, et al. (1995). "Epidermal Damage and Limited Coagulation Depth with the Flashlamp-Pumped Pulsed Dye-Laser—a Histochemical-Study." *Journal of Investigative Dermatology* 104(5): 798-802.

Holland, A. J. A., H. C. O. Martin, et al. (2002). "Laser Doppler imaging prediction of burn wound outcome in children." *Burns* 28(1): 11-17.

Hotate, K. and T. Okugawa (1994). "Optical Information-Processing by Synthesis of the Coherence Function." *Journal of Lightwave Technology* 12(7): 1247-1255.

Hourdakis, C. J. and A. Perris (1995). "A Monte-Carlo Estimation of Tissue Optical-Properties for Use in Laser Dosimetry." *Physics in Medicine and Biology* 40(3): 351-364.

Hu, Z., F. Li, et al. (2000). "Wavelength-tunable narrow-linewidth semiconductor fiber-ring laser." *IEEE Photonics Technology Letters* 12(8): 977-979.

Huang, F., W. Yang, et al. (2001). "Quadrature spectral interferometric detection and pulse shaping." *Optics Letters* 26(6): 382-384.

Huang, X. R. and R. W. Knighton (2002). "Linear birefringence of the retinal nerve fiber layer measured in vitro with a multispectral imaging micropolarimeter." *Journal of Biomedical Optics* 7(2): 199-204.

Huber, R., M. Wojtkowski, et al. (2005). "Amplified, frequency swept lasers for frequency domain reflectometry and OCT imaging: design and scaling principles." *Optics Express* 13(9): 3513-3528.

Hunter, D. G., J. C. Sandruck, et al. (1999). "Mathematical modeling of retinal birefringence scanning." *Journal of the Optical Society of America a-Optics Image Science and Vision* 16(9): 2103-2111.

Hurwitz, H. H. and R. C. Jones (1941). "A new calculus for the treatment of optical systems II. Proof of three general equivalence theorems." *Journal of the Optical Society of America* 31(7): 493-499.

Huttner, B., C. De Barros, et al. (1999). "Polarization-induced pulse spreading in birefringent optical fibers with zero differential group delay." *Optics Letters* 24(6): 370-372.

Huttner, B., B. Gisin, et al. (1999). "Distributed PMD measurement with a polarization-OTDR in optical fibers." *Journal of Lightwave Technology* 17(10): 1843-1848.

Huttner, B., J. Reecht, et al. (1998). "Local birefringence measurements in single-mode fibers with coherent optical frequency-domain reflectometry." *Ieee Photonics Technology Letters* 10(10): 1458-1460.

Hyde, S. C. W., N. P. Barry, et al. (1995). "Sub-100-Mu-M Depth-Resolved Holographic Imaging through Scattering Media in the near-Infrared." *Optics Letters* 20(22): 2330-2332.

Hyde, S. C. W., N. P. Barry, et al. (1995). "Depth-Resolved Holographic Imaging through Scattering Media by Photorefraction." *Optics Letters* 20(11): 1331-1333.

Iftimia, N. V., B. E. Bouma, et al. (2004). "Adaptive ranging for optical coherence tomography." *Optics Express* 12(17): 4025-4034.

Iida, T., N. Hagimura, et al. (2000). "Evaluation of central serous chorioretinopathy with optical coherence tomography." *American Journal of Ophthalmology* 129(1): 16-20.

Imai, M., H. Iijima, et al. (2001). "Optical coherence tomography of tractional macular elevations in eyes with proliferative diabetic retinopathy. [republished in Am J Ophthalmol. Sep. 2001;132(3):458-61 ; 11530091.]." *American Journal of Ophthalmology* 132(1): 81-4.

Indebetouw, G. and P. Klysubun (2000). "Imaging through scattering media with depth resolution by use of low-coherence gating in spatiotemporal digital holography." *Optics Letters* 25(4): 212-214.

Ip, M. S., B. J. Baker, et al. (2002). "Anatomical outcomes of surgery for idiopathic macular hole as determined by optical coherence tomography." *Archives of Ophthalmology* 120(1): 29-35.

Ismail, R., V. Tanner, et al. (2002). "Optical coherence tomography imaging of severe commotio retinae and associated macular hole." *British Journal of Ophthalmology* 86(4): 473-4.

Izatt, J. A., M. R. Hee, et al. (1994). "Optical Coherence Microscopy in Scattering Media." *Optics Letters* 19(8): 590-592.

Izatt, J. A., M. R. Hee, et al. (1994). "Micrometer-scale resolution imaging of the anterior eye in vivo with optical coherence tomography." *Archives of Ophthalmology* 112 (12): 1584-9.

Izatt, J. A., M. D. Kulkami, et al. (1997). "In vivo bidirectional color Doppler flow imaging of picoliter blood volumes using optical coherence tomography." *Optics Letters* 22(18): 1439-1441.

Izatt, J. A., M. D. Kulkarni, et al. (1996). "Optical coherence tomography and microscopy in gastrointestinal tissues." *IEEE Journal of Selected Topics in Quantum Electronics* 2(4): 1017.

Jacques, S. L., J. S. Nelson, et al. (1993). "Pulsed Photothermal Radiometry of Port-Wine-Stain Lesions." *Applied Optics* 32(13): 2439-2446.

Jacques, S. L., J. R. Roman, et al. (2000). "Imaging superficial tissues with polarized light." *Lasers in Surgery and Medicine* 26(2): 119-129.

Jang, I. K., B. E. Bouma, et al. (2002). "Visualization of coronary atherosclerotic plaques in patients using optical coherence tomography: Comparison with intravascular ultrasound." *Journal of the American College of Cardiology* 39(4): 604-609.

Jang, I. K., B. D. MacNeill, et al. (2002). "In-vivo characterization of coronary plaques in patients with ST elevation acute myocardial infarction using optical coherence tomography (OCT)." *Circulation* 106(19): 698-698 3440 Suppl. S,.

Jang, I. K., G. J. Tearney, et al. (2000). "Comparison of optical coherence tomography and intravascular ultrasound for detection of coronary plaques with large lipid-core in living patients." *Circulation* 102(18): 509-509.

Jeng, J. C., A. Bridgeman, et al. (2003). "Laser Doppler imaging determines need for excision and grafting in advance of clinical judgment: a prospective blinded trial." *Burns* 29(7): 665-670.

Jesser, C. A., S. A. Boppart, et al. (1999). "High resolution imaging of transitional cell carcinoma with optical coherence tomography: feasibility for the evaluation of bladder pathology." *British Journal of Radiology* 72: 1170-1176.

Johnson, C. A., J. L. Keltner, et al. (2002). "Baseline visual field characteristics in the ocular hypertension treatment study." *Ophthalmology* 109(3): 432-7.

Jones, R. C. (1941). "A new calculus for the treatment of optical systems III. The Sohncke theory of optical activity." *Journal of the Optical Society of America* 31(7): 500-503.

Jones, R. C. (1941). "A new calculus for the treatment of optical systems I. Description and discussion of the calculus." *Journal of the Optical Society of America* 31(7): 488-493.

Jones, R. C. (1942). "A new calculus for the treatment of optical systems. IV." Journal of the *Optical Society of America* 32(8): 486-493.

Jones, R. C. (1947). "A New Calculus for the Treatment of Optical Systems .6. Experimental Determination of the Matrix." *Journal of the Optical Society of America* 37(2): 110-112.

Jones, R. C. (1947). "A New Calculus for the Treatment of Optical Systems .5. A More General Formulation, and Description of Another Calculus." *Journal of the Optical Society of America* 37(2): 107-110.

Jones, R. C. (1948). "A New Calculus for the Treatment of Optical Systems .7. Properties of the N-Matrices." *Journal of the Optical Society of America* 38(8): 671-685.

Jones, R. C. (1956). "New Calculus for the Treatment of Optical Systems .8. Electromagnetic Theory." *Journal of the Optical Society of America* 46(2): 126-131.

Jopson, R. M., L. E. Nelson, et al. (1999). "Measurement of second-order polarization-mode dispersion vectors in optical fibers." *Ieee Photonics Technology Letters* 11(9): 1153-1155.

Jost, B. M., A. V. Sergienko, et al. (1998). "Spatial correlations of spontaneously down-converted photon pairs detected with a single-photon-sensitive CCD camera." *Optics Express* 3(2): 81-88.

Kaplan, B., E. Compain, et al. (2000). "Phase-modulated Mueller ellipsometry characterization of scattering by latex sphere suspensions." *Applied Optics* 39 (4): 629-636.

Kass, M. A., D. K. Heuer, et al. (2002). "The Ocular Hypertension Treatment Study: a randomized trial determines that topical ocular hypotensive medication delays or prevents the onset of primary open-angle glaucoma." *Archives of Ophthalmology* 120(6): 701-13; discussion 829-30.

Kasuga, Y., J. Arai, et al. (2000). "Optical coherence tomograghy to confirm early closure of macular holes." *American Journal of Ophthalmology* 130(5): 675-6.

Kaufman, T., S. N. Lusthaus, et al. (1990). "Deep Partial Skin Thickness Burns—a Reproducible Animal-Model to Study Burn Wound-Healing." *Burns* 16(1): 13-16.

Kemp, N. J., J. Park, et al. (2005). "High-sensitivity determination of birefringence in turbid media with enhanced polarization-sensitive optical coherence tomography." *Journal of the Optical Society of America a-Optics Image Science and Vision* 22(3): 552-560.

Kerrigan-Baumrind, L. A., H. A. Quigley, et al. (2000). "Number of ganglion cells in glaucoma eyes compared with threshold visual field tests in the same persons." *Investigative Ophthalmology & Visual Science* 41(3): 741-8.

Kesen, M. R., G. L. Spaeth, et al. (2002). "The Heidelberg Retina Tomograph vs clinical impression in the diagnosis of glaucoma." *American Journal of Ophthalmology* 133(5): 613-6.

Kienle, A. and R. Hibst (1995). "A New Optimal Wavelength for Treatment of Port-Wine Stains." *Physics in Medicine and Biology* 40(10): 1559-1576.

Kienle, A., L. Lilge, et al. (1996). "Spatially resolved absolute diffuse reflectance measurements for noninvasive determination of the optical scattering and absorption coefficients of biological tissue." *Applied Optics* 35(13): 2304-2314.

Kim, B. Y. and S. S. Choi (1981). "Analysis and Measurement of Birefringence in Single-Mode Fibers Using the Backscattering Method." *Optics Letters* 6(11): 578-580.

Kimel, S., L. O. Svaasand, et al. (1994). "Differential Vascular-Response to Laser Photothermolysis." *Journal of Investigative Dermatology* 103(5): 693-700.

Kloppenberg, F. W. H., G. Beerthuizen, et al. (2001). "Perfusion of burn wounds assessed by Laser Doppler Imaging is related to burn depth and healing time." *Burns* 27(4): 359-363.

Knighton, R. W. and X. R. Huang (2002). "Analytical methods for scanning laser polarimetry." *Optics Express* 10(21): 1179-1189.

Knighton, R. W., X. R. Huang, et al. (2002). "Analytical model of scanning laser polarimetry for retinal nerve fiber layer assessment." *Investigative Ophthalmology & Visual Science* 43(2): 383-392.

Knuettel, A. R. S., Joseph M.: Shay, M.; Knutson, Jay R. (1994). "Stationary low-coherence light imaging and spectroscopy using a CCD camera." *Proc. SPIE* , vol. 2135: p. 239-250.

Knuttel, A. and M. Boehlau-Godau (2000). "Spatially confined and temporally resolved refractive index and scattering evaluation in human skin performed with optical coherence tomography." *Journal of Biomedical Optics* 5(1): 83-92.

Knuttel, A. and J. M. Schmitt (1993). "Stationary Depth-Profiling Reflectometer Based on Low-Coherence Interferometry." *Optics Communications* 102(3-4): 193-198.

Knuttel, A., J. M. Schmitt, et al. (1994). "Low-Coherence Reflectometry for Stationary Lateral and Depth Profiling with Acoustooptic Deflectors and a Ccd Camera." *Optics Letters* 19(4): 302-304.
Kobayashi, M., H. Hanafusa, et al. (1991). "Polarization-Independent Interferometric Optical-Time-Domain Reflectometer." *Journal of Lightwave Technology* 9(5): 623-628.
Kolios, M. C., M. D. Sherar, et al. (1995). "Large Blood-Vessel Cooling in Heated Tissues—a Numerical Study." *Physics in Medicine and Biology* 40(4): 477-494.
Koozekanani, D., K. Boyer, et al. (2001). "Retinal thickness measurements from optical coherence tomography using a Markov boundary model." *Ieee Transactions on Medical Imaging* 20(9): 900-916.
Kop, R. H. J. and R. Sprik (1995). "Phase-sensitive interferometry with ultrashort optical pulses." *Review of Scientific Instruments* 66(12): 5459-5463.
Kramer, R. Z., J. Bella, et al. (1999). "Sequence dependent conformational variations of collagen triple-helical structure." *Nature Structural Biology* 6(5): 454-7.
Kulkarni, M. D., T. G. van Leeuwen, et al. (1998). "Velocity-estimation accuracy and frame-rate limitations in color Doppler optical coherence tomography." *Optics Letters* 23(13): 1057-1059.
Kwon, Y. H., C. S. Kim, et al. (2001). "Rate of visual field loss and long-term visual outcome in primary open-angle glaucoma." *American Journal of Ophthalmology* 132(1): 47-56.
Kwong, K. F., D. Yankelevich, et al. (1993). "400-Hz Mechanical Scanning Optical Delay-Line." *Optics Letters* 18(7): 558-560.
Landers, J., I. Goldberg, et al. (2002). "Analysis of risk factors that may be associated with progression from ocular hypertension to primary open angle glaucoma." *Clin Experiment Ophthalmogy* 30(4): 242-7.
Laszlo, A. and A. Venetianer (1998). Heat resistance in mammalian cells: Lessons and challenges. *Stress of Life*. 851: 169-178.
Laszlo, A. and A. Venetianer (1998). "Heat resistance in mammalian cells: lessons and challenges. [Review] [52 refs]." *Annals of the New York Academy of Sciences* 851: 169-78.
Laufer, J., R. Simpson, et al. (1998). "Effect of temperature on the optical properties of ex vivo human dermis and subdermis." *Physics in Medicine and Biology* 43(9): 2479-2489.
Lederer, D. E., J. S. Schuman, et al. (2003). "Analysis of macular volume in normal and glaucomatous eyes using optical coherence tomography." *American Journal of Ophthalmology* 135(6): 838-843.
Lee, P. P., Z. W. Feldman, et al. (2003). "Longitudinal prevalence of major eye diseases." *Archives of Ophthalmology* 121(9): 1303-1310.
Lehrer, M. S., T. T. Sun, et al. (1998). "Strategies of epithelial repair: modulation of stem cell and transit amplifying cell proliferation." *Journal of Cell Science* 111(Pt 19): 2867-75.
Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." *Survey of Ophthalmology* 24(Suppl): 335-610.
Leitgeb, R., C. K. Hitzenberger, et al. (2003). "Performance of fourier domain vs. time domain optical coherence tomography." *Optics Express* 11(8): 889-894.
Leitgeb, R., L. F. Schmetterer, et al. (2002). "Flow velocity measurements by frequency domain short coherence interferometry." *Proc. SPIE* 4619: 16-21.
Leitgeb, R. A., W. Drexler, et al. (2004). "Ultrahigh resolution Fourier domain optical coherence tomography." *Optics Express* 12(10): 2156-2165.
Leitgeb, R. A., C. K. Hitzenberger, et al. (2003). "Phase-shifting algorithm to achieve high-speed long-depth-range probing by frequency-domain optical coherence tomography." *Optics Letters* 28(22): 2201-2203.
Leitgeb, R. A., L. Schmetterer, et al. (2003). "Real-time assessment of retinal blood flow with ultrafast acquisition by color Doppler Fourier domain optical coherence tomography." *Optics Express* 11(23): 3116-3121.
Leitgeb, R. A., L. Schmetterer, et al. (2004). "Real-time measurement of in vitro flow by Fourier-domain color Doppler optical coherence tomography." *Optics Letters* 29 (2): 171-173.

LeRoyBrehonnet, F. and B. LeJeune (1997). "Utilization of Mueller matrix formalism to obtain optical targets depolarization and polarization properties." *Progress in Quantum Electronics* 21(2): 109-151.
Leske, M. C., A. M. Connell, et al. (1995). "Risk factors for open-angle glaucoma. The Barbados Eye Study. [see comments]." *Archives of Ophthalmology* 113(7): 918-24.
Leske, M. C., A. M. Connell, et al. (2001). "Incidence of open-angle glaucoma: the Barbados Eye Studies. The Barbados Eye Studies Group. [see comments]." *Archives of Ophthalmology* 119(1): 89-95.
Leske, M. C., A. Heijl, et al. (1999). "Early Manifest Glaucoma Trial. Design and Baseline Data." *Ophthalmology* 106(11): 2144-2153.
Lewis, S. E., J. R. DeBoer, et al. (2005). "Sensitive, selective, and analytical improvements to a porous silicon gas sensor." *Sensors and Actuators B: Chemical* 110(1): 54-65.
Lexer, F., C. K. Hitzenberger, et al. (1999). "Dynamic coherent focus OCT with depth- independent transversal resolution." *Journal of Modern Optics* 46(3): 541-553.
Li, X., C. Chudoba, et al. (2000). "Imaging needle for optical coherence tomography." *Optics Letters* 25: 1520-1522.
Li, X., T. H. Ko, et al. (2001). "Intraluminal fiber-optic Doppler imaging catheter for structural and functional optical coherence tomography." *Optics Letters* 26: 1906-1908.
Liddington, M. I. and P. G. Shakespeare (1996). "Timing of the thermographic assessment of burns." *Burns* 22(1): 26-8.
Lindmo, T., D. J. Smithies, et al. (1998). "Accuracy and noise in optical Doppler tomography studied by Monte Carlo simulation." *Physics in Medicine and Biology* 43(10): 3045-3064.
Liu, J., X. Chen, et al. (1999). "New thermal wave aspects on burn evaluation of skin subjected to instantaneous heating." *IEEE Transactions on Biomedical Engineering* 46(4): 420-8.
Luke, D. G., R. McBride, et al. (1995). "Polarization mode dispersion minimization in fiber-wound piezoelectric cylinders." *Optics Letters* 20(24): 2550-2552.
MacNeill, B. D., I. K. Jang, et al. (2004). "Focal and multi-focal plaque distributions in patients with macrophage acute and stable presentations of coronary artery disease." *Journal of the American College of Cardiology* 44(5): 972-979.
Mahgerefteh, D. and C. R. Menyuk (1999). "Effect of first-order PMD compensation on the statistics of pulse broadening in a fiber with randomly varying birefringence." *Ieee Photonics Technology Letters* 11(3): 340-342.
Maitland, D. J. and J. T. Walsh, Jr. (1997). "Quantitative measurements of linear birefringence during heating of native collagen." *Lasers in Surgery & Medicine* 20(3): 310-8.
Majaron, B., S. M. Srinivas, et al. (2000). "Deep coagulation of dermal collagen with repetitive Er : YAG laser irradiation." *Lasers in Surgery and Medicine* 26(2): 215-222.
Mansuripur, M. (1991). "Effects of High-Numerical-Aperture Focusing on the State of Polarization in Optical and Magnetooptic Data-Storage Systems." *Applied Optics* 30(22): 3154-3162.
Marshall, G. W., S. J. Marshall, et al. (1997). "The dentin substrate: structure and properties related to bonding." *Journal of Dentistry* 25(6): 441-458.
Martin, P. (1997). "Wound healing—Aiming for perfect skin regeneration." *Science* 276 (5309): 75-81.
Martinez, O. E. (1987). "3000 Times Grating Compressor with Positive Group-Velocity Dispersion—Application to Fiber Compensation in 1.3-1.6 Mu-M Region." *Ieee Journal of Quantum Electronics* 23(1): 59-64.
Martinez, O. E., J. P. Gordon, et al. (1984). "Negative Group-Velocity Dispersion Using Refraction." *Journal of the Optical Society of America a-Optics Image Science and Vision* 1(10): 1003-1006.
McKinney, J. D., M. A. Webster, et al. (2000). "Characterization and imaging in optically scattering media by use of laser speckle and a variable-coherence source." *Optics Letters* 25(1): 4-6.
Miglior, S., M. Casula, et al. (2001). "Clinical ability of Heidelberg retinal tomograph examination to detect glaucomatous visual field changes." *Ophthalmology* 108 (9): 1621-7.
Milner, T. E., D. M. Goodman, et al. (1996). "Imaging laser heated subsurface chromophores in biological materials: Determination of lateral physical dimensions." *Physics in Medicine and Biology* 41(1): 31-44.

Milner, T. E., D. M. Goodman, et al. (1995). "Depth Profiling of Laser-Heated Chromophores in Biological Tissues by Pulsed Photothermal Radiometry." *Journal of the Optical Society of America a-Optics Image Science and Vision* 12 (7): 1479-1488.

Milner, T. E., D. J. Smithies, et al. (1996). "Depth determination of chromophores in human skin by pulsed photothermal radiometry." *Applied Optics* 35(19): 3379-3385.

Mishchenko, M. I. and J. W. Hovenier (1995). "Depolarization of Light Backscattered by Randomly Oriented Nonspherical Particles." *Optics Letters* 20(12): 1356-&.

Mistlberger, A., J. M. Liebmann, et al. (1999). "Heidelberg retina tomography and optical coherence tomography in normal, ocular-hypertensive, and glaucomatous eyes." *Ophthalmology* 106(10): 2027-32.

Mitsui, T. (1999). "High-speed detection of ballistic photons propagating through suspensions using spectral interferometry." *Japanese Journal of Applied Physics* Part 1-Regular Papers Short Notes & Review Papers 38(5A): 2978-2982.

Molteno, A. C., N. J. Bosma, et al. (1999). "Otago glaucoma surgery outcome study: long-term results of trabeculectomy—1976 to 1995." *Ophthalmology* 106(9): 1742-50.

Morgner, U., W. Drexler, et al. (2000). "Spectroscopic optical coherence tomography." *Optics Letters* 25(2): 111-113.

Morgner, U., F. X. Kartner, et al. (1999). "Sub-two-cycle pulses from a Kerr-lens mode-locked Ti : sapphire laser (vol. 24, p. 411, 1999)." *Optics Letters* 24(13): 920-920.

Mourant, J. R., A. H. Hielscher, et al. (1998). "Evidence of intrinsic differences in the light scattering properties of tumorigenic and nontumorigenic cells." *Cancer Cytopathology* 84(6): 366-374.

Muller, M., J. Squier, et al. (1998). "Dispersion pre-compensation of 15 femtosecond optical pulses for high-numerical-aperture objectives." *Journal of Microscopy-Oxford* 191: 141-150.

Muscat, S., N. McKay, et al. (2002). "Repeatability and reproducibility of corneal thickness measurements by optical coherence tomography." *Investigative Ophthalmology & Visual Science* 43(6): 1791-5.

Musch, D. C., P. R. Lichter, et al. (1999). "The Collaborative Initial Glaucoma Treatment Study. Study Design, Methods, and Baseline Characteristics of Enrolled Patients." *Ophthalmology* 106: 653-662.

Neerken, S., Lucassen, G.W., Bisschop, M.A., Lenderink, E., Nuijs, T.A.M. (2004). "Characterization of age-related effects in human skin: A comparative study that applies confocal laser scanning microscopy and optical coherence tomography." *Journal of Biomedical Optics* 9(2): 274-281.

Nelson, J. S., K. M. Kelly, et al. (2001). "Imaging blood flow in human port-wine stain in situ and in real time using optical Doppler tomography." *Archives of Dermatology* 137(6): 741-744.

Newson, T. P., F. Farahi, et al. (1988). "Combined Interferometric and Polarimetric Fiber Optic Temperature Sensor with a Short Coherence Length Source." *Optics Communications* 68(3): 161-165.

November, L. J. (1993). "Recovery of the Matrix Operators in the Similarity and Congruency Transformations—Applications in Polarimetry." *Journal of the Optical Society of America a-Optics Image Science and Vision* 10(4): 719-739.

Oh, W. Y., S. H. Yun, et al. (2005). "Wide tuning range wavelength-swept laser with two semiconductor optical amplifiers." *Ieee Photonics Technology Letters* 17(3): 678-680.

Oka, K. and T. Kato (1999). "Spectroscopic polarimetry with a channeled spectrum." *Optics Letters* 24(21): 1475-1477.

Okugawa, T. and K. Rotate (1996). "Real-time optical image processing by synthesis of the coherence function using real-time holography." *Ieee Photonics Technology Letters* 8(2): 257-259.

Oshima, M., R. Torii, et al. (2001). "Finite element simulation of blood flow in the cerebral artery." *Computer Methods in Applied Mechanics and Engineering* 191 (6-7): 661-671.

Pan, Y. T., H. K. Xie, et al. (2001). "Endoscopic optical coherence tomography based on a microelectromechanical mirror." *Optics Letters* 26(24): 1966-1968.

Parisi, V., G. Manni, et al. (2001). "Correlation between optical coherence tomography, pattern electroretinogram, and visual evoked potentials in open-angle glaucoma patients." *Ophthalmology* 108(5): 905-12.

Park, B. H., M. C. Pierce, et al. (2005). "Real-time fiber-based multi-functional spectral-domain optical coherence tomography at 1.3 mu m." *Optics Express* 13(11): 3931-3944.

Park, D. H., J. W. Hwang, et al. (1998). "Use of laser Doppler flowmetry for estimation of the depth of burns." *Plastic and Reconstructive Surgery* 101(6): 1516-1523.

Pendry, J. B., A. J. Holden, et al. (1999). "Magnetism from conductors and enhanced nonlinear phenomena." *Ieee Transactions on Microwave Theory and Techniques* 47(11): 2075-2084.

Penninckx, D. and V. Morenas (1999). "Jones matrix of polarization mode dispersion." *Optics Letters* 24(13): 875-877.

Pierce, M. C., M. Shishkov, et al. (2005). "Effects of sample arm motion in endoscopic polarization-sensitive optical coherence tomography." *Optics Express* 13(15): 5739-5749.

Pircher, M., E. Gotzinger, et al. (2003). "Measurement and imaging of water concentration in human cornea with differential absorption optical coherence tomography." *Optics Express* 11(18): 2190-2197.

Pircher, M., E. Gotzinger, et al. (2003). "Speckle reduction in optical coherence tomography by frequency compounding." *Journal of Biomedical Optics* 8(3): 565-569.

Podoleanu, A. G., G. M. Dobre, et al. (1998). "En-face coherence imaging using galvanometer scanner modulation." *Optics Letters* 23(3): 147-149.

Podoleanu, A. G. and D. A. Jackson (1999). "Noise analysis of a combined optical coherence tomograph and a confocal scanning ophthalmoscope." *Applied Optics* 38(10): 2116-2127.

Podoleanu, A. G., J. A. Rogers, et al. (2000). "Three dimensional OCT images from retina and skin." *Optics Express* 7(9): 292-298.

Podoleanu, A. G., M. Seeger, et al. (1998). "Transversal and longitudinal images from the retina of the living eye using low coherence reflectometry." *Journal of Biomedical Optics* 3(1): 12-20.

Poole, C. D. (1988). "Statistical Treatment of Polarization Dispersion in Single-Mode Fiber." *Optics Letters* 13(8): 687-689.

Povazay, B., K. Bizheva, et al. (2002). "Submicrometer axial resolution optical coherence tomography." *Optics Letters* 27(20): 1800-1802.

Qi, B., A. P. Himmer, et al. (2004). "Dynamic focus control in high-speed optical coherence tomography based on a microelectromechanical mirror." *Optics Communications* 232(1-6): 123-128.

Radhakrishnan, S., A. M. Rollins, et al. (2001). "Real-time optical coherence tomography of the anterior segment at 1310 nm." *Archives of Ophthalmology* 119(8): 1179-1185.

Rogers, A. J. (1981). "Polarization-Optical Time Domain Reflectometry—a Technique for the Measurement of Field Distributions." Applied Optics 20(6): 1060-1074.

Rollins, A. M. and J. A. Izatt (1999). "Optimal interferometer designs for optical coherence tomography." *Optics Letters* 24(21): 1484-1486.

Rollins, A. M., R. Ung-arunyawee, et al. (1999). "Real-time in vivo imaging of human gastrointestinal ultrastructure by use of endoscopic optical coherence tomography with a novel efficient interferometer design." *Optics Letters* 24(19): 1358-1360.

Rollins, A. M., S. Yazdanfar, et al. (2002). "Real-time in vivo colors Doppler optical coherence tomography." *Journal of Biomedical Optics* 7(1): 123-129.

Rollins, A. M., S. Yazdanfar, et al. (2000). "Imaging of human retinal hemodynamics using color Doppler optical coherence tomography." *Investigative Ophthalmology & Visual Science* 41(4): S548-S548.

Sandoz, P. (1997). "Wavelet transform as a processing tool in white-light interferometry." *Optics Letters* 22(14): 1065-1067.

Sankaran, V., M. J. Everett, et al. (1999). "Comparison of polarized-light propagation in biological tissue and phantoms." *Optics Letters* 24(15): 1044-1046.

Sankaran, V., J. T. Walsh, et al. (2000). "Polarized light propagation through tissue phanto, ehms containing densely packed scatterers." *Optics Letters* 25(4): 239-241.

Sarunic, M. V., M. A. Choma, et al. (2005). "Instantaneous complex conjugate resolved spectral domain and swept-source OCT using 3×3 fiber couplers." *Optics Express* 13(3): 957-967.

Sathyam, U. S., B. W. Colston, et al. (1999). "Evaluation of optical coherence quantitation of analytes in turbid media by use of two wavelengths." *Applied Optics* 38(10): 2097-2104.

Schmitt, J. M. (1997). "Array detection for speckle reduction in optical coherence microscopy." *Physics in Medicine and Biology* 42(7): 1427-1439.

Schmitt, J. M. (1999). "Optical coherence tomography (OCT): A review." *Ieee Journal of Selected Topics in Quantum Electronics* 5(4): 1205-1215.

Schmitt, J. M. and A. Knuttel (1997). "Model of optical coherence tomography of heterogeneous tissue." *Journal of the Optical Society of America a-Optics Image Science and Vision* 14(6): 1231-1242.

Schmitt, J. M., S. L. Lee, et al. (1997). "An optical coherence microscope with enhanced resolving power in thick tissue." *Optics Communications* 142(4-6): 203-207.

Schmitt, J. M., S. H. Xiang, et al. (1998). "Differential absorption imaging with optical coherence tomography." *Journal of the Optical Society of America a-Optics Image Science and Vision* 15(9): 2288-2296.

Schmitt, J. M., S. H. Xiang, et al. (1999). "Speckle in optical coherence tomography." *Journal of Biomedical Optics* 4(1): 95-105.

Schmitt, J. M., M. J. Yadlowsky, et al. (1995). "Subsurface Imaging of Living Skin with Optical Coherence Microscopy." *Dermatology* 191(2): 93-98.

Shi, H., J. Finlay, et al. (1997). "Multiwavelength 10-GHz picosecond pulse generation from a single-stripe semiconductor diode laser." *Ieee Photonics Technology Letters* 9(11): 1439-1441.

Shi, H., I. Nitta, et al. (1999). "Demonstration of phase correlation in multiwavelength mode-locked semiconductor diode lasers." *Optics Letters* 24(4): 238-240.

Simon, R. (1982). "The Connection between Mueller and Jones Matrices of Polarization Optics." *Optics Communications* 42(5): 293-297.

Smithies, D. J., T. Lindmo, et al. (1998). "Signal attenuation and localization in optical coherence tomography studied by Monte Carlo simulation." *Physics in Medicine and Biology* 43(10): 3025-3044.

Sorin, W. V. and D. F. Gray (1992). "Simultaneous Thickness and Group Index Measurement Using Optical Low-Coherence Reflectometry." *Ieee Photonics Technology Letters* 4(1): 105-107.

Sticker, M., C. K. Hitzenberger, et al. (2001). "Quantitative differential phase measurement and imaging in transparent and turbid media by optical coherence tomography." *Optics Letters* 26(8): 518-520.

Sticker, M., M. Pircher, et al. (2002). "En face imaging of single cell layers by differential phase-contrast optical coherence microscopy." *Optics Letters* 27(13): 1126-1128.

Stoller, P., B. M. Kim, et al. (2002). "Polarization-dependent optical second-harmonic imaging of a rat-tail tendon." *Journal of Biomedical Optics* 7(2): 205-214.

Sun, C. S. (2003). "Multiplexing of fiber-optic acoustic sensors in a Michelson interferometer configuration." *Optics Letters* 28(12): 1001-1003.

Swanson, E. A., J. A. Izatt, et al. (1993). "In-Vivo Retinal Imaging by Optical Coherence Tomography." *Optics Letters* 18(21): 1864-1866.

Takada, K., A. Himeno, et al. (1991). "Phase-Noise and Shot-Noise Limited Operations of Low Coherence Optical-Time Domain Reflectometry." *Applied Physics Letters* 59(20): 2483-2485.

Takenaka, H. (1973). "Unified Formalism for Polarization Optics by Using Group-Theory I (Theory)." *Japanese Journal of Applied Physics* 12(2): 226-231.

Tanno, N., T. Ichimura, et al. (1994). "Optical Multimode Frequency-Domain Reflectometer." *Optics Letters* 19(8): 587-589.

Tan-no, N., T. Ichimura, et al. (1994). "Optical Multimode Frequency-Domain Reflectometer." *Optics Letters* 19(8): 587-589.

Targowski, P., M. Wojtkowski, et al. (2004). "Complex spectral OCT in human eye imaging in vivo." *Optics Communications* 229(1-6): 79-84.

Tearney, G. J., S. A. Boppart, et al. (1996). "Scanning single-mode fiber optic catheter- endoscope for optical coherence tomography (vol. 21, p. 543, 1996)." *Optics Letters* 21(12): 912-912.

Tearney, G. J., B. E. Bouma, et al. (1996). "Rapid acquisition of in vivo biological images by use of optical coherence tomography." *Optics Letters* 21(17): 1408-1410.

Tearney, G. J., B. E. Bouma, et al. (1997). "In vivo endoscopic optical biopsy with optical coherence tomography." *Science* 276(5321): 2037-2039.

Tearney, G. J., M. E. Brezinski, et al. (1996). "Catheter-based optical imaging of a human coronary artery." *Circulation* 94(11): 3013-3013.

Tearney, G. J., M. E. Brezinski, et al. (1997). "In vivo endoscopic optical biopsy with optical coherence tomography." *Science* 276(5321): 2037-9.

Tearney, G. J., M. E. Brezinski, et al. (1997). "Optical biopsy in human gastrointestinal tissue using optical coherence tomography." *American Journal of Gastroenterology* 92(10): 1800-1804.

Tearney, G. J., M. E. Brezinski, et al. (1995). "Determination of the refractive index of highly scattering human tissue by optical coherence tomography." *Optics Letters* 20(21): 2258-2260.

Tearney, G. J., I. K. Jang, et al. (2000). "Porcine coronary imaging in vivo by optical coherence tomography." *Acta Cardiologica* 55(4): 233-237.

Tearney, G. J., R. H. Webb, et al. (1998). "Spectrally encoded confocal microscopy." *Optics Letters* 23(15): 1152-1154.

Tearney, G. J., H. Yabushita, et al. (2003). "Quantification of macrophage content in atherosclerotic plaques by optical coherence tomography." *Circulation* 107(1): 113-119.

Tower, T. T. and R. T. Tranquillo (2001). "Alignment maps of tissues: I. Microscopic elliptical polarimetry." *Biophysical Journal* 81(5): 2954-2963.

Tower, T. T. and R. T. Tranquillo (2001). "Alignment maps of tissues: II. Fast harmonic analysis for imaging." *Biophysical Journal* 81(5): 2964-2971.

Troy, T. L. and S. N. Thennadil (2001). "Optical properties of human skin in the near infrared wavelength range of 1000 to 2200 nm." *Journal of Biomedical Optics* 6 (2): 167-176.

Vabre, L., A. Dubois, et al. (2002). "Thermal-light full-field optical coherence tomography." *Optics Letters* 27(7): 530-532.

Vakhtin, A. B., D. J. Kane, et al. (2003). "Common-path interferometer for frequency-domain optical coherence tomography." *Applied Optics* 42(34): 6953-6958.

Vakhtin, A. B., K. A. Peterson, et al. (2003). "Differential spectral interferometry: an imaging technique for biomedical applications." *Optics Letters* 28(15): 1332-1334.

Vakoc, B. J., S. H. Yun, et al. (2005). "Phase-resolved optical frequency domain imaging." *Optics Express* 13(14): 5483-5493.

van Leeuwen, T. G., M. D. Kulkarni, et al. (1999). "High-flow-velocity and shear-rate imaging by use of color Doppler optical coherence tomography." *Optics Letters* 24(22): 1584-1586.

Vansteenkiste, N., P. Vignolo, et al. (1993). "Optical Reversibility Theorems for Polarization—Application to Remote-Control of Polarization." *Journal of the Optical Society of America a-Optics Image Science and Vision* 10(10): 2240-2245.

Vargas, O., E. K. Chan, et al. (1999). "Use of an agent to reduce scattering in skin." *Lasers in Surgery and Medicine* 24(2): 133-141.

Wang, R. K. (1999). "Resolution improved optical coherence-gated tomography for imaging through biological tissues." *Journal of Modern Optics* 46(13): 1905-1912.

Wang, X. J., T. E. Milner, et al. (1997). "Measurement of fluid-flow-velocity profile in turbid media by the use of optical Doppler tomography." *Applied Optics* 36(1): 144-149.

Wang, X. J., T. E. Milner, et al. (1995). "Characterization of Fluid-Flow Velocity by Optical Doppler Tomography." *Optics Letters* 20(11): 1337-1339.

Wang, Y. M., J. S. Nelson, et al. (2003). "Optimal wavelength for ultrahigh-resolution optical coherence tomography." *Optics Express* 11(12): 1411-1417.

Wang, Y. M., Y. H. Zhao, et al. (2003). "Ultrahigh-resolution optical coherence tomography by broadband continuum generation from a photonic crystal fiber." *Optics Letters* 28(3): 182-184.

Watkins, L. R., S. M. Tan, et al. (1999). "Determination of interferometer phase distributions by use of wavelets." *Optics Letters* 24(13): 905-907.

Wetzel, J. (2001). "Optical coherence tomography in dermatology: a review." *Skin Research and Technology* 7(1): 1-9.

Wentworth, R. H. (1989). "Theoretical Noise Performance of Coherence-Multiplexed Interferometric Sensors." *Journal of Lightwave Technology* 7(6): 941-956.

Westphal, V., A. M. Rollins, et al. (2002). "Correction of geometric and refractive image distortions in optical coherence tomography applying Fermat's principle." *Optics Express* 10(9): 397-404.

Westphal, V., S. Yazdanfar, et al. (2002). "Real-time, high velocity-resolution color Doppler optical coherence tomography." *Optics Letters* 27(1): 34-36.

Williams, P. A. (1999). "Rotating-wave-plate Stokes polarimeter for differential group delay measurements of polarization-mode dispersion." *Applied Optics* 38(31): 6508-6515.

Wojtkowski, M., T. Bajraszewski, et al. (2003). "Real-time in vivo imaging by high-speed spectral optical coherence tomography." *Optics Letters* 28(19): 1745-1747.

Wojtkowski, M., A. Kowalczyk, et al. (2002). "Full range complex spectral optical coherence tomography technique in eye imaging." *Optics Letters* 27(16): 1415-1417.

Wojtkowski, M., R. Leitgeb, et al. (2002). "In vivo human retinal imaging by Fourier domain optical coherence tomography." *Journal of Biomedical Optics* 7(3): 457-463.

Wojtkowski, M., R. Leitgeb, et al. (2002). "Fourier domain OCT imaging of the human eye in vivo." *Proc. SPIE* 4619: 230-236.

Wojtkowski, M., V. J. Srinivasan, et al. (2004). "Ultrahigh-resolution, high-speed, Fourier domain optical coherence tomography and methods for dispersion compensation." *Optics Express* 12(11): 2404-2422.

Wong, B. J. F., Y. H. Zhao, et al. (2004). "Imaging the internal structure of the rat cochlea using optical coherence tomography at 0.827 mu m and 1.3 mu m." *Otolaryngology-Head and Neck Surgery* 130(3): 334-338.

Yang, C., A. Wax, et al. (2001). "Phase-dispersion optical tomography." *Optics Letters* 26(10): 686-688.

Yang, C., A. Wax, et al. (2001). "Phase-referenced interferometer with subwavelength and subhertz sensitivity applied to the study of cell membrane dynamics." *Optics Letters* 26(16): 1271-1273.

Yang, C. H., A. Wax, et al. (2001). "Phase-dispersion optical tomography." *Optics Letters* 26(10): 686-688.

Yang, C. H., A. Wax, et al. (2000). "Interferometric phase-dispersion microscopy." *Optics Letters* 25(20): 1526-1528.

Yang, V. X. D., M. L. Gordon, et al. (2002). "Improved phase-resolved optical Doppler tomography using the Kasai velocity estimator and histogram segmentation." *Optics Communications* 208(4-6): 209-214.

Yang, V. X. D., M. L. Gordon, et al. (2003). "High speed, wide velocity dynamic range Doppler optical coherence tomography (Part I): System design, signal processing, and performance." *Optics Express* 11(7): 794-809.

Yang, V. X. D., M. L. Gordon, et al. (2003). "High speed, wide velocity dynamic range Doppler optical coherence tomography (Part II): Imaging in vivo cardiac dynamics of *Xenopus laevis*." *Optics Express* 11(14): 1650-1658.

Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." *Optics Express* 11(19): 2416-2424.

Yang, V. X. D., B. Qi, et al. (2003). "In vivo feasibility of endoscopic catheter-based Doppler optical coherence tomography." *Gastroenterology* 124(4): A49-A50.

Yao, G. and L. H. V. Wang (2000). "Theoretical and experimental studies of ultrasound-modulated optical tomography in biological tissue." *Applied Optics* 39(4): 659-664.

Yazdanfar, S. and J. A. Izatt (2002). "Self-referenced Doppler optical coherence tomography." *Optics Letters* 27(23): 2085-2087.

Yazdanfar, S., M. D. Kulkarni, et al. (1997). "High resolution imaging of in vivo cardiac dynamics using color Doppler optical coherence tomography." *Optics Express* 1 (13) : 424-431.

Yazdanfar, S., A. M. Rollins, et al. (2000). "Imaging and velocimetry of the human retinal circulation with color Doppler optical coherence tomography." *Optics Letters* 25(19): 1448-1450.

Yazdanfar, S., A. M. Rollins, et al. (2000). "Noninvasive imaging and velocimetry of human retinal blood flow using color Doppler optical coherence tomography." *Investigative Ophthalmology & Visual Science* 41(4): S548-S548.

Yazdanfar, S., A. M. Rollins, et al. (2003). "In vivo imaging of human retinal flow dynamics by color Doppler optical coherence tomography." *Archives of Ophthalmology* 121(2): 235-239.

Yazdanfar, S., C. H. Yang, et al. (2005). "Frequency estimation precision in Doppler optical coherence tomography using the Cramer-Rao lower bound." *Optics Express* 13(2): 410-416.

Yun, S. H., C. Boudoux, et al. (2004). "Extended-cavity semiconductor wavelength-swept laser for biomedical imaging." *Ieee Photonics Technology Letters* 16(1): 293-295.

Yun, S. H., C. Boudoux, et al. (2003). "High-speed wavelength-swept semiconductor laser with a polygon-scanner-based wavelength filter. " *Optics Letters* 28(20): 1981-1983.

Yun, S. H., G. J. Tearney, et al. (2004). "Pulsed-source and swept-source spectral- domain optical coherence tomography with reduced motion artifacts." *Optics Express* 12(23): 5614-5624.

Yun, S. H., G. J. Tearney, et al. (2004). "Removing the depth-degeneracy in optical frequency domain imaging with frequency shifting." *Optics Express* 12(20): 4822-4828.

Yun, S. H., G. J. Tearney, et al. (2004). "Motion artifacts in optical coherence tomography with frequency-domain ranging." *Optics Express* 12(13): 2977-2998.

Zhang, J., J. S. Nelson, et al. (2005). "Removal of a mirror image and enhancement of the signal-to-noise ratio in Fourier-domain optical coherence tomography using an electro-optic phase modulator." *Optics Letters* 30(2): 147-149.

Zhang, Y., M. Sato, et al. (2001). "Numerical investigations of optimal synthesis of several low coherence sources for resolution improvement." *Optics Communications* 192(3-6): 183-192.

Zhang, Y., M. Sato, et al. (2001). "Resolution improvement in optical coherence tomography by optimal synthesis of light-emitting diodes." *Optics Letters* 26(4): 205-207.

Zhao, Y., Z. Chen, et al. (2002). "Real-time phase-resolved functional optical coherence tomography by use of optical Hilbert transformation." *Optics Letters* 27(2): 98-100.

Zhao, Y. H., Z. P. Chen, et al. (2000). "Doppler standard deviation imaging for clinical monitoring of in vivo human skin blood flow." *Optics Letters* 25(18): 1358-1360.

Zhao, Y. H., Z. P. Chen, et al. (2000). "Phase-resolved optical coherence tomography and optical Doppler tomography for imaging blood flow in human skin with fast scanning speed and high velocity sensitivity." *Optics Letters* 25(2): 114-116.

Zhou, D., P. R. Prucnal, et al. (1998). "A widely tunable narrow linewidth semiconductor fiber ring laser." *IEEE Photonics Technology Letters* 10(6): 781-783.

Zuluaga, A. F. and R. Richards-Kortum (1999). "Spatially resolved spectral interferometry for determination of subsurface structure." *Optics Letters* 24(8): 519-521.

Zvyagin, A. V., J. B. FitzGerald, et al. (2000). "Real-time detection technique for Doppler optical coherence tomography." *Optics Letters* 25(22): 1645-1647.

Marc Nikles et al., "Brillouin gain spectrum characterization in single-mode optical fibers", *Journal of Lightwave Technology* 1997, 15 (10): 1842-1851.

Tsuyoshi Sonehara et al., "Forced Brillouin Spectroscopy Using Frequency-Tunable Continuous-Wave Lasers", *Physical Review Letters* 1995, 75 (23): 4234-4237.

Hajime Tanaka et al., "New Method of Superheterodyne Light Beating Spectroscopy for Brillouin-Scattering Using Frequency-Tunable Lasers", *Physical Review Letters* 1995, 74 (9): 1609-1612.

Webb RH et al. "Confocal Scanning Laser Ophthalmoscope", *Applied Optics* 1987, 26 (8): 1492-1499.

Andreas Zumbusch et al. "Three-dimensional vibrational imaging by coherent anti-Stokes Raman scattering", *Physical Review Letters* 1999, 82 (20): 4142-4145.

Katrin Kneipp et al., "Single molecule detection using surface-enhanced Raman scattering (SERS)", *Physical Review Letters* 1997, 78 (9): 1667-1670.

K.J. Koski et al., "Brillouin imaging" *Applied Physics Letters* 87, 2005.

Boas et al., "Diffusing temporal light correlation for burn diagnosis", *SPIE*, 1999, 2979:468-477.

David J. Briers, "Speckle fluctuations and biomedical optics: implications and applications", *Optical Engineering*, 1993, 32(2):277-283.Clark et al., "Tracking Speckle Patterns with Optical Correlation", *SPIE*, 1992, 1772:77-87.

Clark et al., "Tracking Speckle Patterns with Optical Correlation", *SPIE*, 1992, 1772:77-87.

Facchini et al., "An endoscopic system for DSPI", *Optik*, 1993, 95(1):27-30.

Hrabovsky, M., "Theory of speckle dispacement and decorrelation: application in mechanics", *SPIE*, 1998, 3479:345-354.

Sean J. Kirkpatrick et al., "Micromechanical behavior of cortical bone as inferred from laser speckle data", *Journal of Biomedical Materials Research*, 1998, 39(3):373-379.

Sean J. Kirkpatrick et al., "Laser speckle microstrain measurements in vascular tissue", *SPIE*, 1999, 3598:121-129.

Loree et al., "Mechanical Properties of Model Atherosclerotic Lesion Lipid Pools", *Arteriosclerosis and Thrombosis*, 1994, 14(2):230-234.

Podbielska, H. "Interferometric Methods and Biomedical Research", *SPIE*, 1999, 2732:134-141.

Richards-Kortum et al., "Spectral diagnosis of atherosclerosis using an optical fiber laser catheter", *American Heart Journal*, 1989, 118(2):381-391.

Ruth, B. "blood flow determination by the laser speckle method", *Int J Microcirc: Clin Exp*, 1990, 9:21-45.

Shapo et al., "Intravascular strain imaging: Experiments on an Inhomogeneous Phantom", *IEEE Ultrasonics Symposium* 1996, 2:1177-1180.

Shapo et al., "Ultrasonic displacement and strain imaging of coronary arteries with a catheter array", *IEEE Ultrasonics Symposium* 1995, 2:1511-1514.

Thompson et al., "Imaging in scattering media by use of laser speckle", *Opt. Soc. Am. A.*, 1997, 14(9):2269-2277.

Thompson et al., "Diffusive media characterization with laser speckle", *Applied Optics*, 1997, 36(16):3726-3734.

Tuchin, Valery V., "Coherent Optical Techniques for the Analysis of Tissue Structure and Dynamics," *Journal of Biomedical Optics*, 1999, 4(1):106-124.

M. Wussling et al., "Laser diffraction and speckling studies in skeletal and heart muscle", *Biomed, Biochim, Acta*, 1986, 45(1/2):S 23-S 27.

T. Yoshimura et al., "Statistical properties of dynamic speckles", *J. Opt. Soc. Am A*. 1986, 3(7):1032-1054.

Zimnyakov et al., "Spatial speckle correlometry in applications to tissue structure monitoring", *Applied Optics* 1997, 36(22): 5594-5607.

Zimnyakov et al., "A study of statistical properties of partially developed speckle fields as applied to the diagnosis of structural changes in human skin", *Optics and Spectroscopy*, 1994, 76(5): 747-753.

Zimnyakov et al., "Speckle patterns polarization analysis as an approach to turbid tissue structure monitoring", *SPIE*1999, 2981:172-180.

Ramasamy Manoharan et al., "Biochemical analysis and mapping of atherosclerotic human artery using FT-IR microspectroscopy", *Atherosclerosis*, May 1993, 181-1930.

N.V. Salunke et al., "Biomechanics of Atherosclerotic Plaque" *Critical Reviews™ in Biomedical Engineering* 1997, 25(3):243-285.

D. Fu et al., "Non-invasive quantitative reconstruction of tissue elasticity using an iterative forward approach", Phys. Med. Biol. 2000 (45): 1495-1509.

S.B. Adams Jr. et al., "The use of polarization sensitive optical coherence tomography and elastography to assess connective tissue", Optical Soc. of American Washington 2002, p. 3.

International Search Report for International Patent application No. PCT/US2005/039740.

International Written Opinion for International Patent application No. PCT/US2005/039740.

International Search Report for International Patent application No. PCT/US2005/030294.

International Written Opinion for International Patent application No. PCT/US2005/043951.

International Search Report for International Patent application No. PCT/US2005/043951.

Erdelyi et al. "Generation of diffraction-free beams for applications in optical microlithography", J. Vac. Sci. Technol. B 15 (12), Mar./Apr. 1997, pp. 287-292.

International Search Report for International Patent application No. PCT/US2005/023664.

International Written Opinion for International Patent application No. PCT/US2005/023664.

Tearney et al., "Spectrally encoded miniature endoscopy" Optical Society of America; Optical Letters vol. 27, No. 6, Mar. 15, 2002; pp. 412-414.

Yelin et al., "Double-clad Fiber for Endoscopy" Optical Society of America; Optical Letters vol. 29, No. 20, Oct. 16, 2005; pp. 2408-2410.

International Search Report for International Patent application No. PCT/US2001/049704.

International Search Report for International Patent application No. PCT/US2004/039454.

International Written Opinion for International Patent application No. PCT/US2004/039454.

PCT International Preliminary Report on Patentability for International Application No. PCT/US2004/038404 dated Jun. 2, 2006.

Notice of Reasons for Rejection and English translation for Japanese Patent Application No. 2002-538830.

Office Action dated Aug. 24, 2006 for U.S. Appl. No. 10/137,749.

Barry Cense et al., "Spectral-domain polarization-sensitive optical coherence tomography at 850nm", Coherence Domain Optical Methods and Optical Coherence Tomography in Biomedicine IX, 2005, pp. 159-162.

A. Ymeti et al., "Integration of microfluidics with a four-channel integrated optical Young interferometer immunosensor", Biosensors and Bioelectronics, Elsevier Science Publishers, 2005, pp. 1417-1421.

PCT International Search Report for Application No. PCT/US2006/018865 filed May 5, 2006.

International Written Opinion for International Patent application No. PCT/US2006/018865 filed May 5, 2006.

John M. Poneros, "Diagnosis of Barrett's esophagus using optical coherence tomography", Gastrointestinal Endoscopy clinics of North America, 14 (2004) pp. 573-588.

P.F. Escobar et al., "Diagnostic efficacy of optical coherence tomography in the management of preinvasive and invasive cancer of uterine cervix and vulva", Int. Journal of Gynecological Cancer 2004, 14, pp. 470-474.

Ko T et al., "Ultrahigh resolution in vivo versus ex vivo OCT imaging and tissue preservation", Conference on Lasers and electro-optics, 2001, pp. 252-253.

Paul M. Ripley et al., "A comparison of Artificial Intelligence techniques for spectral classification in the diagnosis of human pathologies based upon optical biopsy", Journal of Optical Society of America, 2000, pp. 217-219.

Wolfgang Drexler et al., "Ultrahigh-resolution optical coherence tomography", Journal of Biomedical Optics Spie USA, 2004, pp. 47-74.

PCT International Search Report for Application No. PCT/US2006/016677 filed Apr. 28, 2006.

International Written Opinion for International Patent application No. PCT/US2006/016677 filed Apr. 28, 2006.

Office Action dated Nov. 13, 2006 for U.S. Appl. No. 10/501,268.

Office Action dated Nov. 20, 2006 for U.S. Appl. No. 09/709,162.

PCT International Search Report and Written Opinion for Application No. PCT/US2004/023585 filed Jul. 23, 2004.

Office Action dated Dec. 6, 2006 for U.S. Appl. No. 10/997,789.

Elliott, K. H. "The use of commercial CCD cameras as linear detectors in the physics undergraduate teaching laboratory", European Journal of Physics 19, 1998, pp. 107-117.

Lauer, V. "New approach to optical diffraction tomography yielding a vector equation of diffraction tomography and a novel tomographic microscope", Journal of Microscopy vol. 205, Issue 2, 2002, pp. 165-176.

Yu, P. et al. "Imaging of tumor necroses using full-frame optical coherence imaging", Proceedings of SPIE vol. 4956, 2003, pp. 34-41.

Zhao, Y. et al. "Three-dimensional reconstruction of in vivo blood vessels in human skin using phase-resolved optical Doppler tomography", IEEE Journal of Selected Topics in Quantum Electronics 7.6 (2001): 931-935.

Office Action dated Dec. 18, 2006 for U.S. Appl. No. 10/501,276.

Devesa, Susan S. et al. (1998) "Changing Patterns in the Incidence of Esphegeal and Gastric Carcinoma in the United States." *American Cancer Society* vol. 83, No. 10 pp. 2049-2053.

Barr, H et al. (2005) "Endoscopic Therapy for Barrett's Oesophaugs" *Gut* vol. 54:875-884.

Johnston, Mark H.(2005) "Technology Insight: Ablative Techniques for Barrett's Esophagus—Current and Emerging Trends" www.Nature.com/clinicalpractice/gasthep.

Falk, Gary W. et al. (1997) "Surveillance of Patients with Barrett's Esophagus for Dysplasia and Cancer with Ballon Cytology" *Gastroenterology* vol. 112, pp. 1787-1797.

Sepchler, Stuart Jon. (1997) "Barrett's Esophagus: Should We Brush off this Balloning Problem?" *Gastroenterology* vol. 112, pp. 2138-2152.

Froehly, J. et al. (2003) "Multiplexed 3D Imaging Using Wavelength Encoded Spectral Interferometry: A Proof of Principle" *Optics Communications* vol. 222, pp. 127-136.

Kubba A.K. et al. (1999) "Role of p53 Assessment in Management of Barrett's Esophagus" *Digestive Disease and Sciences* vol. 44, No. 4. pp. 659-667.

Reid, Brian J. (2001) "p53 and Neoplastic Progression in Barrett's Esophagus" *The American Journal of Gastroenterology* vol. 96, No. 5, pp. 1321-1323.

Sharma, P. et al.(2003) "Magnification Chromoendoscopy for the Detection of Intestinal Metaplasia and Dysplasia in Barrett's Oesophagus" *Gut* vol. 52, pp. 24-27.

Kuipers E.J et al. (2005) "Diagnostic and Therapeutic Endoscopy" *Journal of Surgical Oncology* vol. 92, pp. 203-209.

Georgakoudi, Irene et al. (2001) "Fluorescence, Reflectance, and Light-Scattering Spectroscopy for Evaluating Dysplasia in Patients with Barrett's Esophagus" *Gastroenterology* vol. 120, pp. 1620-1629.

Adrain, Alyn L. et al. (1997) "High-Resolution Endoluminal Sonography is a Sensitive Modality for the Identification of Barrett's Meaplasia" *Gastrointestinal Endoscopy* vol. 46, No. 2, pp. 147-151.

Canto, Marcia Irene et al (1999) "Vital Staining and Barrett's Esophagus" *Gastrointestinal Endoscopy* vol. 49, No. 3, part 2, pp. 12-16.

Evans, John A. et al. (2006) "Optical Coherence Tomography to Identify Intramucosal Carcinoma and High-Grade Dysplasia in Barrett's Esophagus" *Clinical Gastroenterology and Hepatology* vol. 4, pp. 38-3.

Poneros, John M. et al. (2001) "Diagnosis of Specialized Intestinal Metaplasia by Optical Coherence Tomography" *Gastroenterology* vol. 120, pp. 7-12.

Ho, W. Y. et al. (2005) "115 KHz Tuning Repetition Rate Ultrahigh-Speed Wavelength-Swept Semiconductor Laser" *Optics Letters* col. 30, No. 23, pp. 3159-3161.

Brown, Stanley B. et al. (2004) "The Present and Future Role of Photodynamic Therapy in Cancer Treatment" *The Lancet Oncology* vol. 5, pp. 497-508.

Boogert, Jolanda Van Den et al. (1999) "Endoscopic Ablation Therapy for Barrett's Esophagua with High-Grade Dysplasia: A Review" *The American Journal of Gastroenterology* vol. 94, No. 5, pp. 1153-1160.

Sampliner, Richard E. et al. (1996) "Reversal of Barrett's Esophagus with Acid Suppression and Multipolar Electrocoagulation: Preliminary Results" *Gastrointestinal Endoscopy* vol. 44, No. 5, pp. 532-535.

Sampliner, Richard E. (2004) "Endoscopic Ablative Therapy for Barrett's Esophagus: Current Status" *Gastrointestinal Endoscopy* vol. 59, No. 1, pp. 66-69.

Soetikno, Roy M. et al. (2003) "Endoscopic Mucosal resection" *Gastrointestinal Endoscopy* vol. 57, No. 4, pp. 567-579.

Ganz, Robert A. et al. (2004) "Complete Ablation of Esophageal Epithelium with a Balloon-based Bipolar Electrode: A Phased Evaluation in the Porcine and in the Human Esophagus" *Gastrointestinal Endoscopy* vol. 60, No. 6, pp. 1002-1010.

Pfefer, Jorje at al. (2006) "Performance of the Aer-O-Scope, A Pneumatic, Self Propelling, Self Navigating Colonoscope in Animal Experiments" *Gastrointestinal Endoscopy* vol. 63, No. 5, pp. AB223.

Overholt, Bergein F. et al. (1999) "Photodynamic Therapy for Barrett's Esophagus: Follow-Up in 100 Patients" *Gastrointestinal Endoscopy* vol. 49, No. 1, pp. 1-7.

Vogel, Alfred et al. (2003) "Mechanisms of Pulsed Laser Ablation of Biological Tissues" *American Chemical Society* vol. 103, pp. 577-644.

McKenzie, A. L. (1990) "Physics of Thermal Processes in Laser-Tissue Interaction" *Phys. Med. Biol* vol. 35, No. 9, pp. 1175-1209.

Anderson, R. Rox et al. (1983) "Selective Photothermolysis" Precise Microsurgery by Selective Absorption of Pulsed Radiation *Science* vol. 220, No. 4596, pp. 524-527.

Jacques, Steven L. (1993) "Role of Tissue Optics and Pulse Duration on Tissue Effects During High-Power Laser Irradiation" *Applied Optics* vol. 32, No. 13, pp. 2447-2454.

Nahen, Kester et al. (1999) "Investigations on Acoustic On-Line Monitoring of IR Laser Ablation of burned Skin" *Lasers in Surgery and Medicine* vol. 25, pp. 69-78.

Jerath, Maya R. et al. (1993) "Calibrated Real-Time Control of Lesion Size Based on Reflectance Images" *Applied Optics* vol. 32, No. 7, pp. 1200-1209.

Jerath, Maya R. et al (1992) "Dynamic Optical Property Changes: Implications for Reflectance Feedback Control of Photocoagulation" *Journal of Photochemical,.Photobiology. B: Biol* vol. 16, pp. 113-126.

Deckelbaum, Lawrence I. (1994) "Coronary Laser Angioplasty" *Lasers in Surgery and Medicine* vol. 14, pp. 101-110.

Kim, B.M. et al. (1998) "Optical Feedback Signal for Ultrashort Laser Pulse Ablation of Tissue" *Applied Surface Science* vol. 127-129, pp. 857-862.

Brinkman, Ralf et al. (1996) "Analysis of Cavitation Dynamics During Pulsed Laser Tissue Ablation by Optical On-Line Monitoring" *IEEE Journal of Selected Topics in Quantum Electronics* vol. 2, No. 4, pp. 826-835.

Whelan, W.M. et al. (2005) "A novel Strategy for Monitoring Laser Thermal Therapy Based on Changes in Optothermal Properties of Heated Tissues" *International Journal of Thermophysics* vol. 26., No. 1, pp. 233-241.

Thomsen, Sharon et al. (1990) "Microscopic Correlates of Macroscopic Optical Property Changes During Thermal Coagulation of Myocardium" *SPIE* vol. 1202, pp. 2-11.

Khan, Misban Huzaira et al. (2005) "Intradermally Focused Infrared Laser Pulses: Thermal Effects at Defined Tissue Depths" *Lasers in Surgery and Medicine* vol. 36, pp. 270-280.

Neumann, R.A. et al. (1991) "Enzyme Histochemical Analysis of Cell Viability After Argon Laser-Induced Coagulation Necrosis of the Skin" *Journal of the American Academy of Dermatology* vol. 25, No. 6, pp. 991-998.

Nadkarni, Seemantini K. et al (2005) "Charaterization of Atherosclerotic Plaques by Laser Speckle Imaging" *Circulation* vol. 112, pp. 885-892.

Zimnyakov, Dmitry A. et al (2002) "Speckle-Contrast Monitoring of Tissue Thermal Modification" *Applied Optics* vol. 41, No. 28, pp. 5989-5996.

Morelli, J.G., et al (1986) "Tunable Dye Laser (577 nm) Treatment of Port Wine Stains" *Lasers in Surgery and Medicine* vol. 6, pp. 94-99.

French, P.M.W. et al. (1993) "Continuous-wave Mode-Locked $Cr^{4+}$: YAG Laser" *Optics Letters* vol. 18, No. 1, pp. 39-41.

Sennaroglu, Alphan at al. (1995) "Efficient Continuous-Wave Chromium-Doped YAG Laser" *Journal of Optical Society of America* vol. 12, No. 5, pp. 930-937.

Bouma, B et al. (1994) "Hybrid Mode Locking of a Flash-Lamp-Pumped Ti: $AI_2O_3$ Laser" *Optics Letters* vol. 19, No. 22, pp. 1858-1860.

Bouma, B et al. (1995) "High Resolution Optical Coherence Tomography Imaging Using a Mode-Locked Ti: $Al_2O_3$ Laser Source" *Optics Letters* vol. 20, No. 13, pp. 1486-1488.

Fernández, Cabrera Delia et al. "Automated detection of retinal layer structures on optical coherence tomography images", *Optics Express* vol. 13, No. 25, Oct. 4, 2005, pp. 10200-10216.

Ishikawa, Hiroshi et al. "Macular Segmentation with optical coherence tomography", Investigative Ophthalmology & Visual Science, vol. 46, No. 6, Jun. 2005, pp. 2012-2017.
Hariri, Lida P. et al. "Endoscopic Optical Coherence Tomography and Laser-Induced Fluorescence Spectroscopy in a Murine Colon Cancer Model", Laser in Surgery and Medicine, vol. 38, 2006, pp. 305-313.
PCT International Search Report and Written Opinion for Application No. PCT/US2006/031905 dated May 3, 2007.
PCT International Search Report and Written Opinion for Application No. PCT/US2007/060481 dated May 23, 2007.
PCT International Search Report and Written Opinion for Application No. PCT/US2007/060717 dated May 24, 2007.
PCT International Search Report and Written Opinion for Application No. PCT/US2007/060319 dated Jun. 6, 2007.
D. Yelin et al., "Three-dimensional imaging using spectral encoding heterodyne interferometry", Optics Letters, Jul. 15, 2005, vol. 30, No. 14, pp. 1794-1796.
Akiba, Masahiro et al. "En-face optical coherence imaging for three-dimensional microscopy", SPIE, 2002, pp. 8-15.
Office Action dated Aug. 10, 2007 for U.S. Appl. No. 10/997,789.
Office Action dated Feb. 2, 2007 for U.S. Appl. No. 11/174,425.
PCT International Search Report and Written Opinion for Application No. PCT/US2007/060657 dated Aug. 13, 2007.
Joo, Chulmin et al., Spectral-domain optical coherence phase microscopy for quantitative phase-contrast imaging, Optics Letters, Aug. 15, 2005, vol. 30, No. 16, pp. 2131-2133.
Guo, Bujin et al., "Laser-based mid-infrared reflectance imaging of biological tissues", Optics Express, Jan. 12, 2004, vol. 12, No. 1, pp. 208-219.
Office Action dated Mar. 28, 2007 for U.S. Appl. No. 11/241,907.
Office Action dated May 23, 2007 for U.S. Appl. No. 10/406,751.
Office Action dated May 23, 2007 for U.S. Appl. No. 10/551,735.
PCT International Search Report and Written Opinion for Application No. PCT/US2007/061815 dated Aug. 2, 2007.
Sir Randall, John et al., "Brillouin scattering in systems of biological significance", Phil. Trans. R. Soc. Lond. A 293, 1979, pp. 341-348.
Takagi, Yasunari, "Application of a microscope to Brillouin scattering spectroscopy", Review of Scientific Instruments, No. 12, Dec. 1992, pp. 5552-5555.
Lees, S. et al., "Studies of Compact Hard Tissues and Collagen by Means of Brillouin Light Scattering", Connective Tissue Research, 1990, vol. 24, pp. 187-205.
Berovic, N. "Observation of Brillion scattering from single muscle fibers", European Biophysics Journal, 1989, vol. 17, pp. 69-74.
PCT International Search Report and Written Opinion for Application No. PCT/US2007/062465 dated Aug. 8, 2007.
Pyhtila John W. et al., "Rapid, depth-resolved light scattering measurements using Fourier domain, angle-resolved low coherence interferometry", Optics Society of America, 2004.
Pyhtila John W. et al., "Determining nuclear morphology using an improved angle-resolved low coherence interferometry system", Optics Express, Dec. 15, 2003, vol. 11, No. 25, pp. 3473-3484.
Desjardins A.E., et al., "Speckle reduction in OCT using massively-parallel detection and frequency-domain ranging", Optics Express, May 15, 2006, vol. 14, No. 11, pp. 4736-4745.
Nadkarni, Seemantini K., et al., "Measurement of fibrous cap thickness in atherosclerotic plaques by spatiotemporal analysis of laser speckle images", Journal of Biomedical Optics, vol. 11 Marsh/Apr. 2006, pp. 021006-1-021006-8.

PCT International Search Report and Written Opinion for Application No. PCT/US2007/066017 dated Aug. 30, 2007.
Yamanari M. et al., "Polarization sensitive Fourier domain optical coherence tomography with continuous polarization modulation", Proc. of SPIE, vol. 6079, 2006.
Zhang Jun et al., "Full range polarization-sensitive Fourier domain optical coherence tomography", Optics Express, Nov. 29, 2004, vol. 12, No. 24, pp. 6033-6039.
European Patent Office Search report for Application No. 01991092.6-2305 dated Jan. 12, 2006.
PCT International Search Report and Written Opinion for Application No. PCT/US2007/060670 dated Sep. 21, 2007.
J. M. Schmitt et al., "Speckle in Optical Coherence Tomography: An Overview", SPIE vol. 3726, pp. 450-461.
Office Action dated Oct. 11, 2007 for U.S. Appl. No. 11/534,095.
Office Action dated Oct. 9, 2007 for U.S. Appl. No. 09/709,162.
Notice of Allowance dated Oct. 3, 2007 for U.S. Appl. No. 11/225,840.
Siavash Yazdanfar et al., "In Vivo imaging in blood flow in human retinal vessels using color Doppler optical coherence tomography", SPIE, 1999 vol. 3598, pp. 177-184.
Office Action dated Oct. 30, 2007 for U.S. Appl. No. 11/670,069.
Office Action dated Nov. 15, 2007 for U.S. Appl. No. 11/285,301.
Tang C. L. et al., "Wide-band electro-optical tuning of semiconductor lasers", Applied Physics Letters, vol. 30, No. 2, Jan. 15, 1977, pp. 113-116.
Tang C. L. et al., "Transient effects in wavelength-modulated dye lasers", Applied Physics Letters, vol. 26, No. 9, May 1, 1975, pp. 534-537.
Telle M. John, et al., "Very rapid tuning of cw dye laser", Applied Physics Letters, vol. 26, No. 10, May 15, 1975, pp. 572-574.
Telle M. John, et al., "New method for electro-optical tuning of tunable lasers", Applied Physics Letters, vol. 24, No. 2, Jan. 15, 1974, pp. 85-87.
Wang, Xueding et al., "Propagation of polarized light in birefringent turbid media: time-resolved simulations", Optical Imaging Laboratory, Biomedical Engineering Program, Texas A&M University, 2001.
Smith, P.J, M., E.M.; Taylor, C.M.; Selviah, F.R.; Day, S.E.; Commander, L.G., "Variable-Focus Microlenses as a Potential Technology for Endoscopy", 2001.
Lewis, Neil E., et al. "Applications of Fourier Transform Infrared Imaging Microscopy in Neurotoxicity", Annals New York Academy of Sciences, pp. 234-246, May 1997.
Yabushita, H.B., B.E.; Houser, S.L.; Aretz, H.T.; Jang, I.; Schlendorf, K.H.; Kauffman, C.R.; Shiskov, M.; halpern E.F.; Tearney, G.J., "Measurement of Thin Fibrous Caps in Atherosclerotic Plaques by Optical Coherence Tomography", about Jun. 25, 2002.
Barfuss et al. (1989), "Modified Optical Frequency Domain Reflectometry with High Spatial Resolution for Components of Integrated Optic Systems", Journal of Light Technology, IEEE, vol. 7., No. 1.
Yun et al., (2004), "Removing the Depth-Degeneracy in Optical Frequency Domain Imaging with Frequency Shifting", Optics Express, vol. 12, No. 20.
Office Action dated Aug. 18, 2009 for U.S. Appl. No. 12/277,178.
Office Action dated Aug. 13, 2009 for U.S. Appl. No. 10/136,813.
Office Action dated Aug. 6, 2009 for U.S. Appl. No. 11/624,455.

* cited by examiner

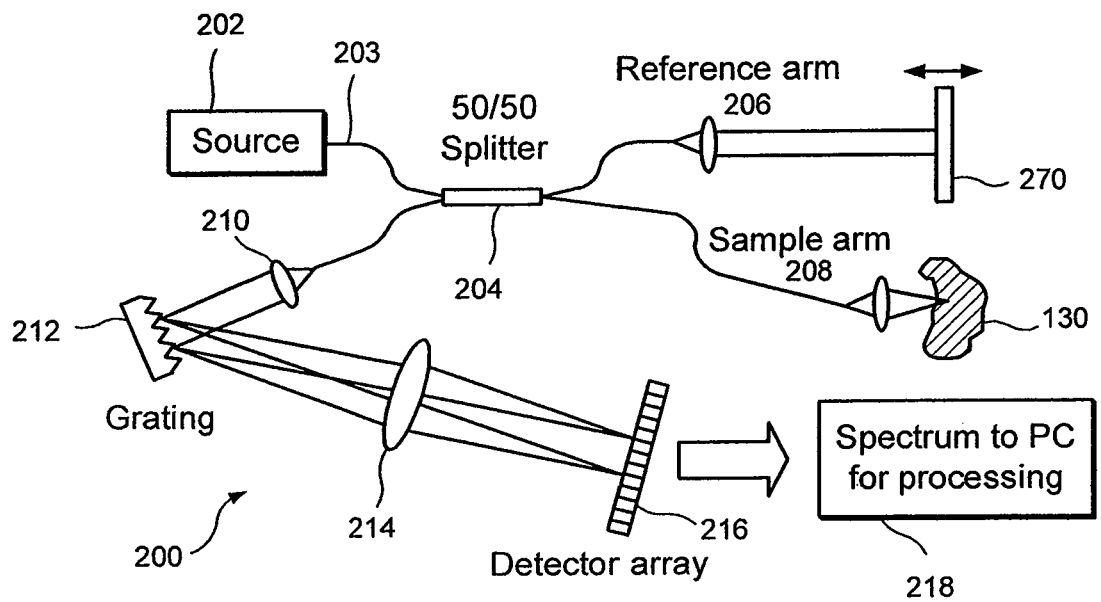
F I G. 3
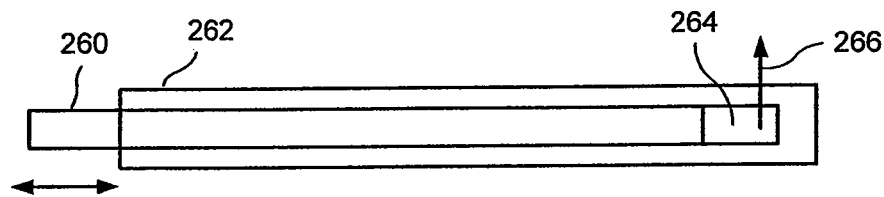
F I G. 4

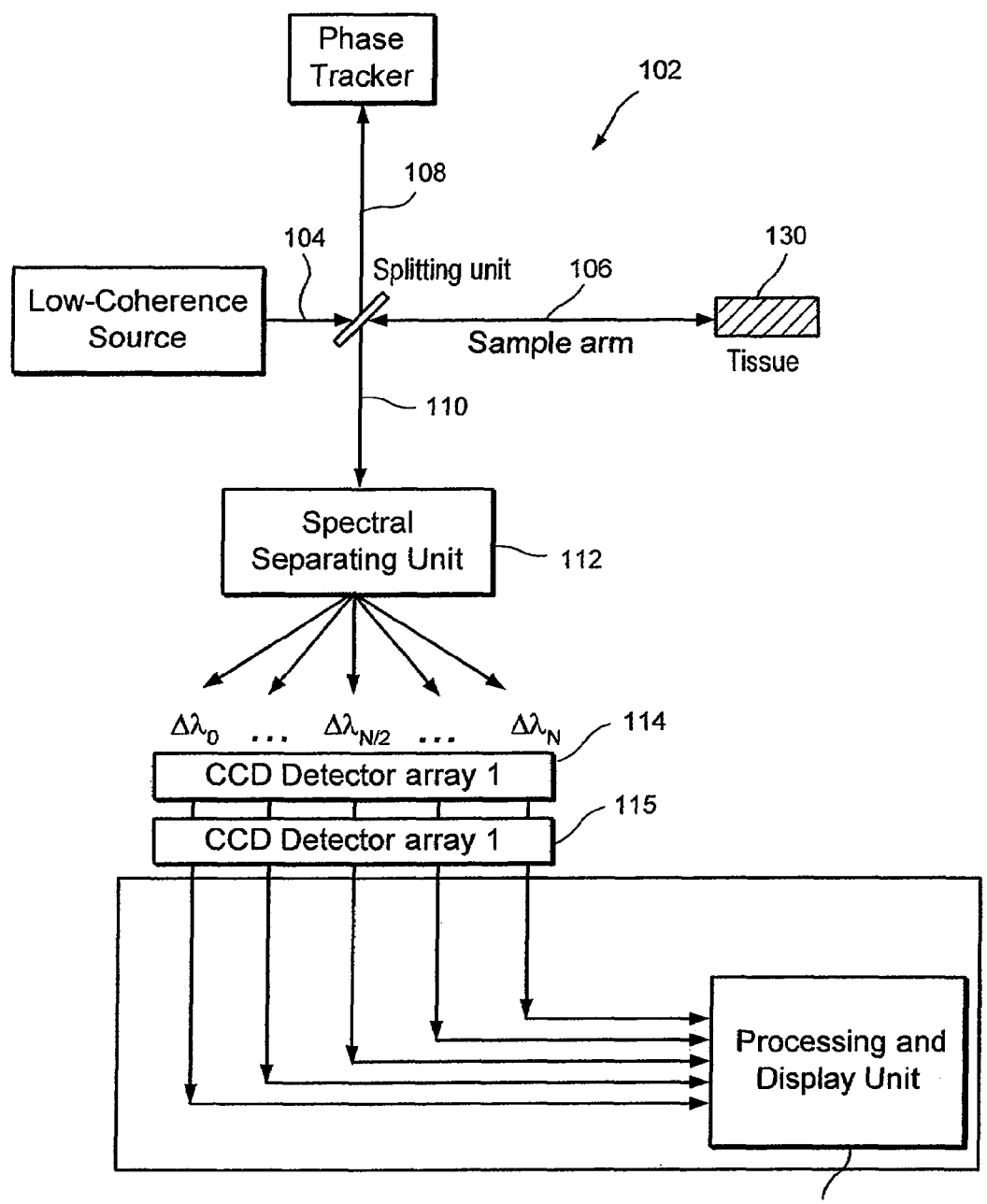
F I G. 5

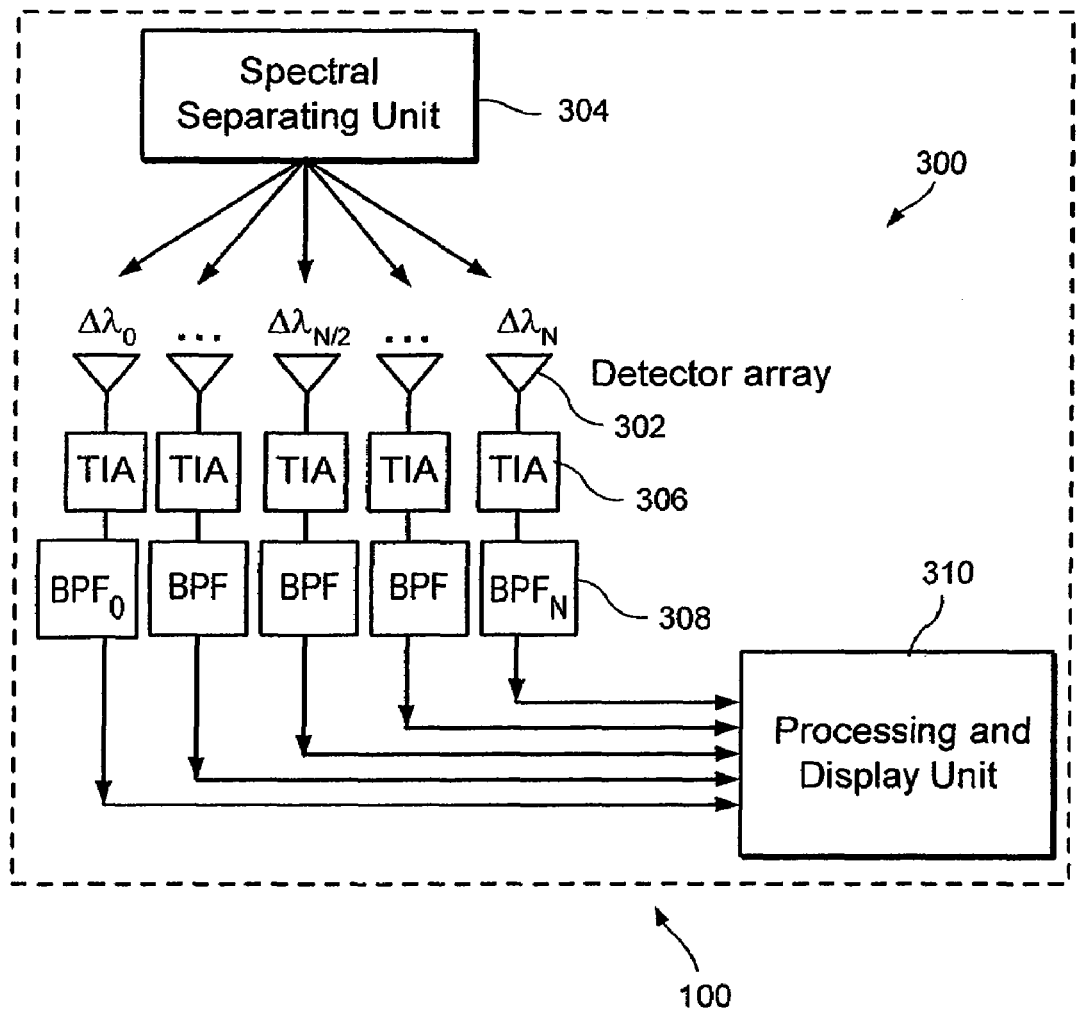
F I G. 6

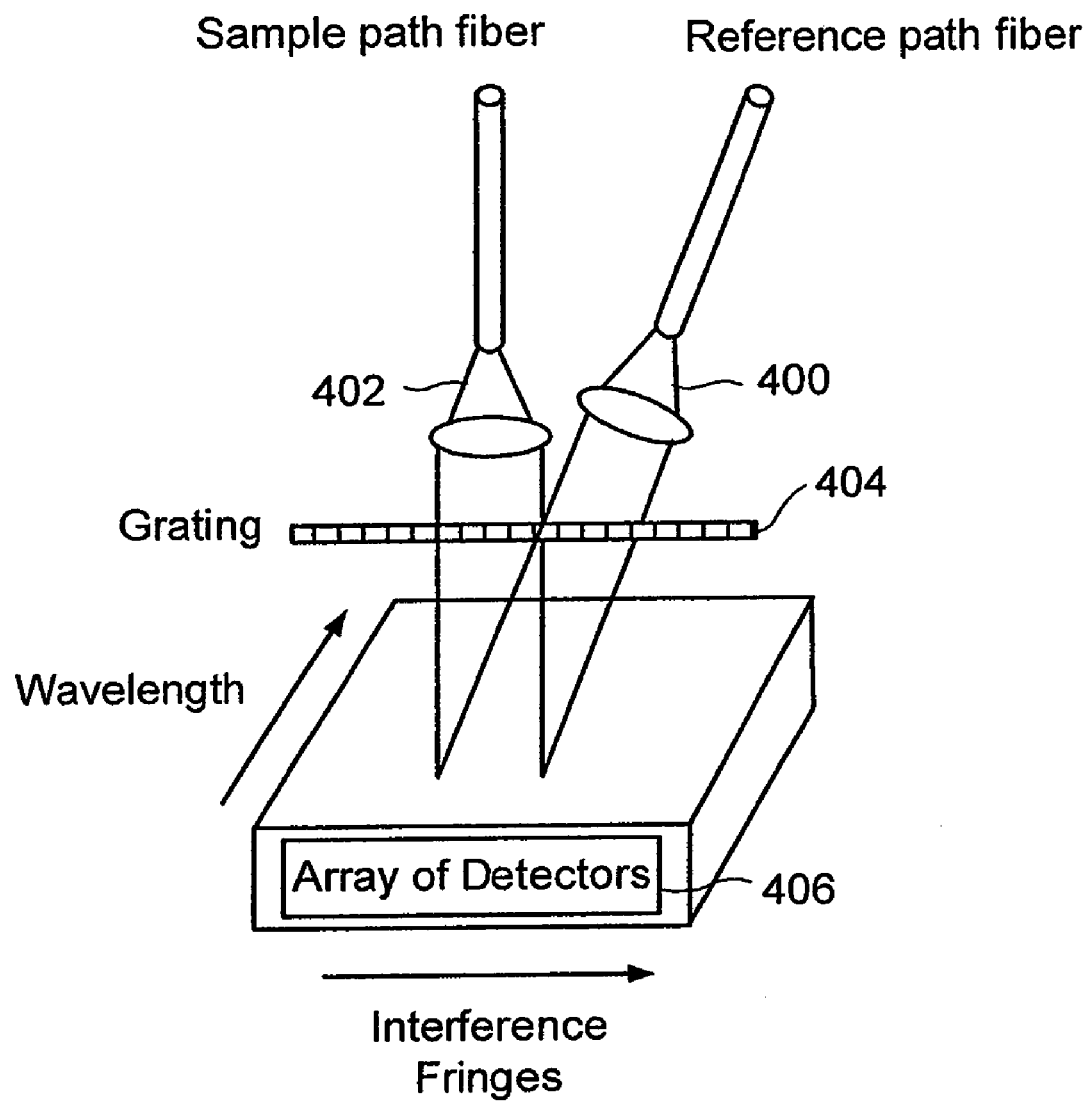
F I G. 9

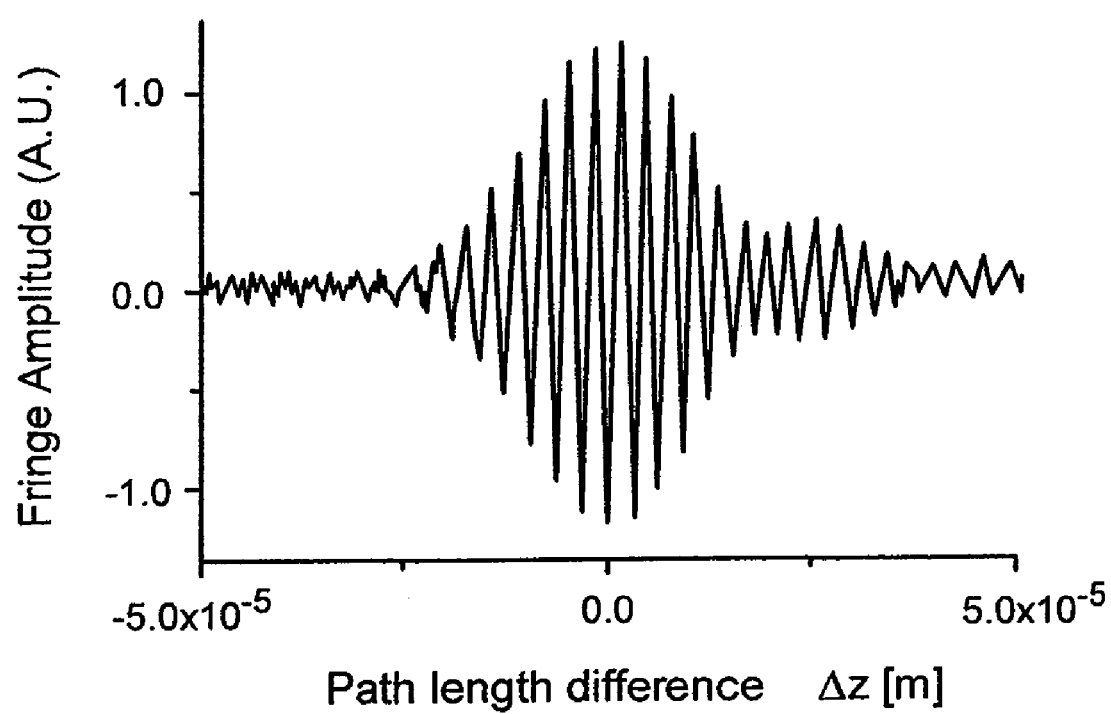
F I G. 14

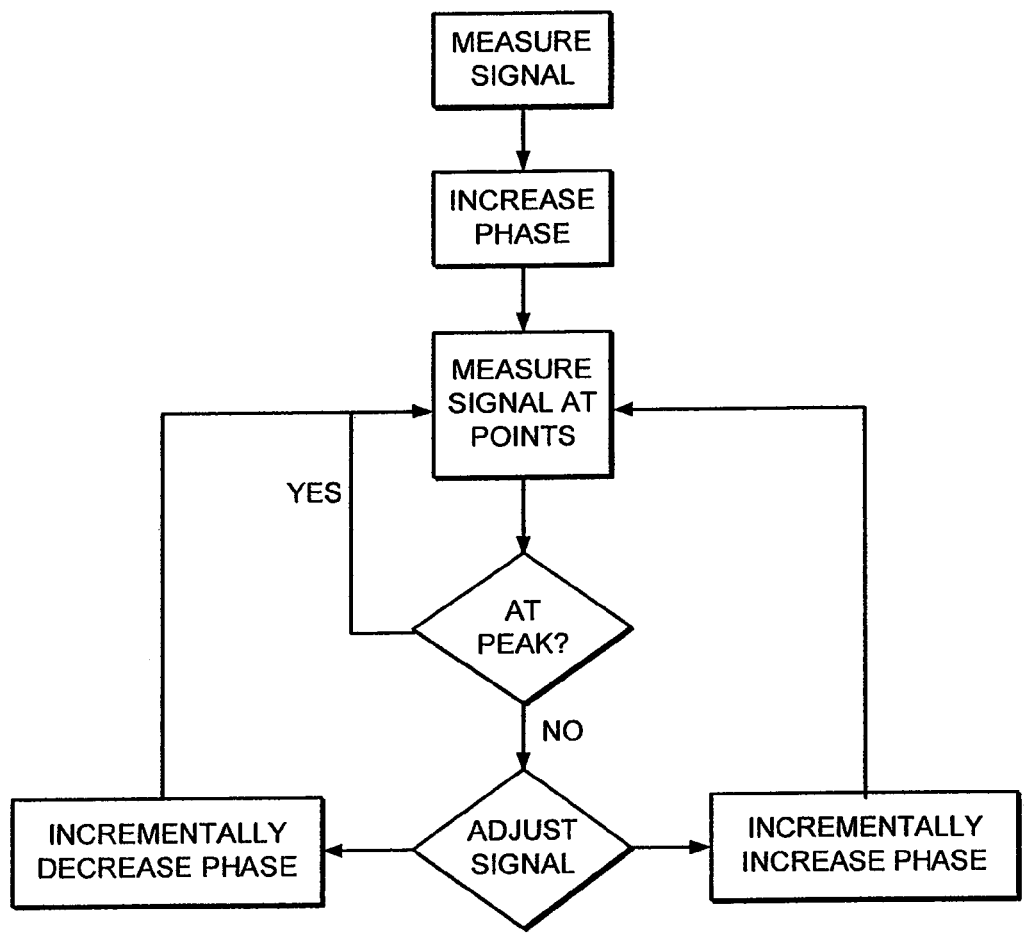
F I G. 15A

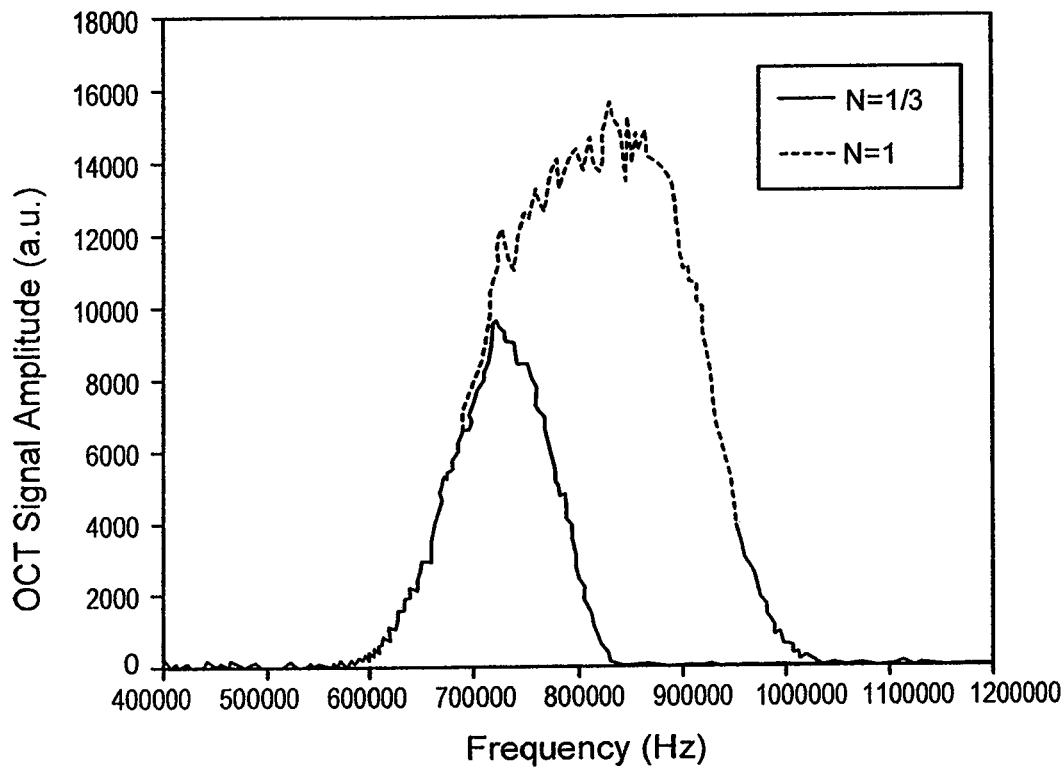
F I G. 17
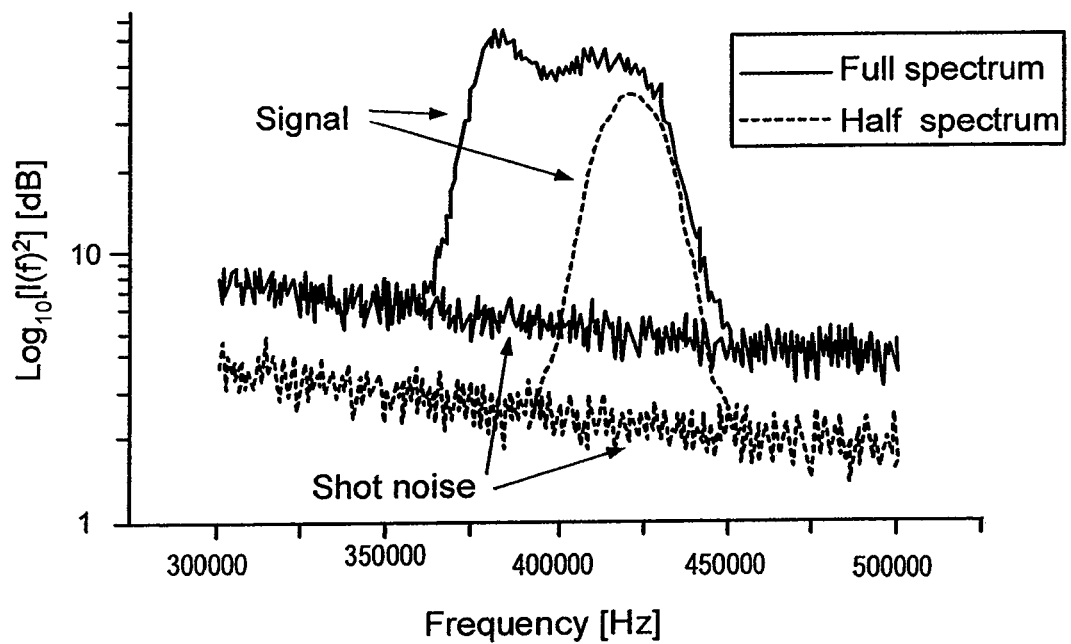
F I G. 18

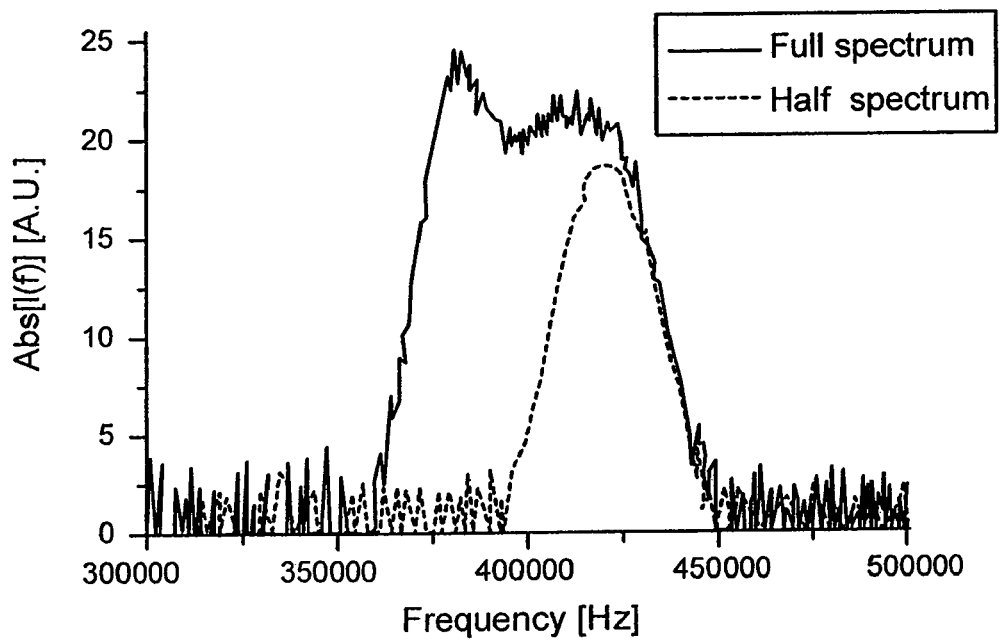
F I G. 19
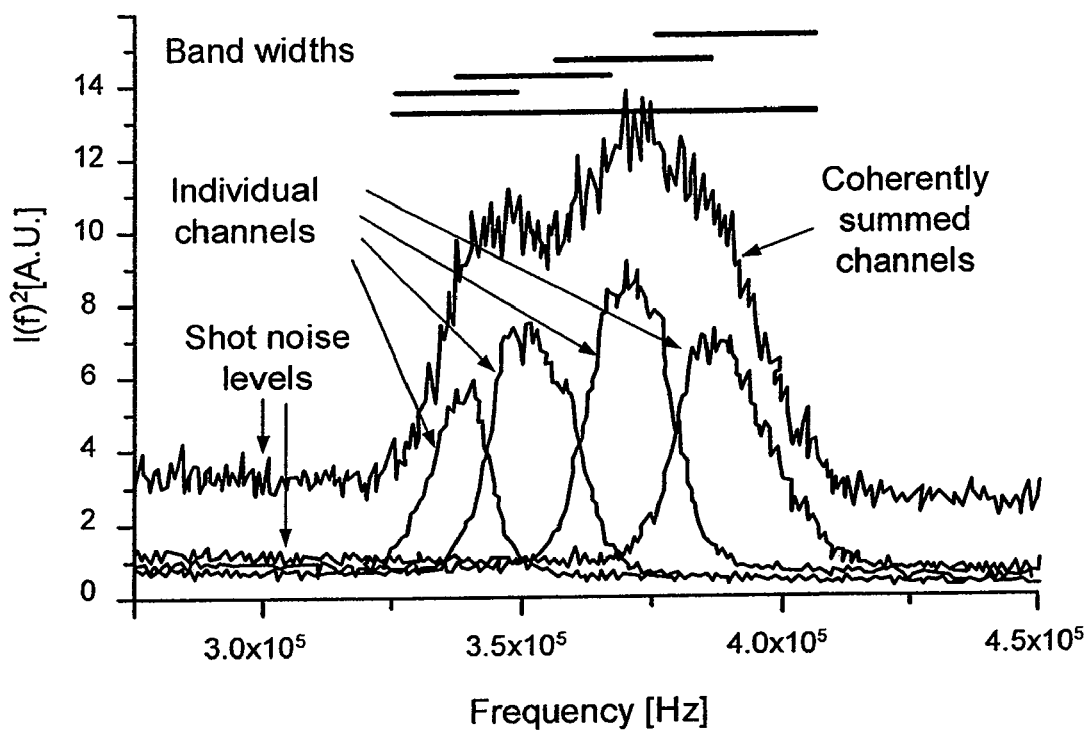
F I G. 20

APPARATUS AND METHOD FOR RANGING AND NOISE REDUCTION OF LOW COHERENCE INTERFEROMETRY LCI AND OPTICAL COHERENCE TOMOGRAPHY OCT SIGNALS BY PARALLEL DETECTION OF SPECTRAL BANDS

CROSS REFERENCE TO RELATED APPLICATION

The present application is a divisional of U.S. patent application Ser. No. 10/501,276, filed Jul. 9, 2004 now U.S. Pat. No. 7,355,716, which is U.S. National Phase of International Application No. PCT/US03/02349 filed Jan. 24, 2003. This application also claims benefit of U.S. provisional patent application No. 60/351,904, filed Jan. 24, 2002, entitled APPARATUS AND METHOD FOR RANGING AND SHOT NOISE REDUCTION OF LOW COHERENCE INTERFEROMETRY (LCI) AND OPTICAL COHERENCE TOMOGRAPHY (OCT) SIGNALS BY PARALLEL DETECTION OF SPECTRAL BANDS, and previously-copending U.S. application Ser. No. 10/136,813, filed Apr. 30, 2002, entitled METHOD AND APPARATUS FOR IMPROVING IMAGE CLARITY AND SENSITIVITY IN OPTICAL COHERENCE TOMOGRAPHY USING DYNAMIC FEEDBACK TO CONTROL FOCAL PROPERTIES AND COHERENCE GATING (now issued as U.S. Pat. No. 7,355,716 on Apr. 8, 2008), both commonly assigned to the assignee of the present application, the disclosures of which are incorporated by reference in its entirety herein.

FIELD OF THE INVENTION

The present invention relates to apparatus, method, logic arrangement and storage medium for dramatically increasing the sensitivity in the detection of optical coherence tomography and low coherence interferometry signals by detecting a parallel set of spectral bands, each band being a unique combination of optical frequencies.

BACKGROUND OF THE ART

Two methods currently exist to implement depth ranging in turbid media. The first method is known as Low Coherence Interferometry ("LCI"). This method uses a scanning system to vary the reference arm length and acquire the interference signal at a detector and demodulating the fringe pattern to obtain the coherence envelope of the source cross correlation function. Optical coherence tomography ("OCT") is a means for obtaining a two-dimensional image using LCI. OCT is described by Swanson et al. in U.S. Pat. No. 5,321,501. Multiple variations on OCT have been patented, but many suffer from less than optimal signal to noise ratio ("SNR"), resulting in non-optimal resolution, low imaging frame rates, and poor depth of penetration. Power usage is a factor in such imaging techniques. For example in ophthalmic uses, only a certain number of milliwatts of power is tolerable before thermal damage can occur. Thus, boosting power is not feasible to increase SNR in such environments. It would be desirable to have a method of raising the SNR without appreciably increasing power requirements.

A second method for depth ranging in turbid media is known in the literature as spectral radar. In spectral radar the real part of the cross spectral density of sample and reference arm light is measured with a spectrometer. Depth profile information is encoded on the cross-spectral density modulation. Prior designs for spectral radar is primarily found in the literature.

The use of spectral radar concepts to increase the signal to noise ratio of LCI and OCT have been described earlier. However, in this description, only the real part of the complex spectral density is measured and the method uses a large number of detector elements (about 2,000) to reach scan ranges on the order of a millimeter. It would be desirable to have a method that would allow for an arbitrary number of detector elements. Secondly, the previously described method uses a single charge coupled device ("CCD") to acquire the data. Since the charge storage capacity is limited, it requires a reduction of the reference arm power to approximately the same level as the sample arm power, giving rise to auto correlation noise on the sample arm light. In addition, since no carrier is generated, the 1/f noise will dominate the noise in this system. Thirdly, even with the short integration times of state of the art CCD technology, phase instabilities in the interferometer reduce fringe visibility of the cross spectral density modulation.

SUMMARY OF THE INVENTION

The present invention can increase the SNR of LCI and OCT by splitting the LCI broad bandwidth source into a number "N" of spectral bands. In one exemplary embodiment, the N spectral bands are individually detected and processed to provide an increase in the SNR by a factor of N. This increase in SNR enables LCI or OCT imaging by a factor of N times faster, or alternatively allows imaging at the same speed with a source that has N times lower power. As a result, the present invention overcomes two of the most important shortcomings of conventional LCI and OCT, namely, source availability and scan speed. The factor N may reach more than 1,000, and allows construction of OCT and LCI systems that can be more than three orders of magnitude improved from OCT and LCI technology currently in practice.

The present invention improves current data acquisition speeds and availability of sources for OCT. Shot noise is due to the statistical fluctuations of the current that are due to the quantized or discrete electric charges. The reduction of shot noise allows for much lower source powers or much higher acquisition rates. Limitations in current data acquisition rates (approximately 4 frames/sec) are imposed by available source power and availability of fast mechanisms for scanning delay. An increase in the sensitivity of the detection by a factor of 8 would allow real time imaging at a speed of about 30 frames per second. An increase of the sensitivity by a factor of about 1,000-2,000 would allow for the use of sources with much lower powers and higher spectral bandwidths which are readily available, cheaper to produce, and can generate higher resolution LCI or OCT scans.

For ophthalmic applications of OCT, the efficient detection preferably allows for a significant increase of acquisition speed. The limitation in ophthalmic applications is the power that is allowed to enter the eye according to the ANSI standards (approximately 700 microwatts at 830 nm). Current data acquisition speed in ophthalmic applications is approximately 100-500 A-lines per second. The power efficient detection would allow for A-line acquisition rates on the order of about 100,000 A-lines per second, or video rate imaging at about 3,000 A-lines per image.

The gain in SNR is achieved because the shot noise has a white noise spectrum. An intensity present at the detector at frequency $\omega$ (or wavelength $\lambda$) contributes only to the signal at frequency $\omega$, but the shot noise is generated at all frequencies. By narrowing the optical band width per detector, the shot noise contribution at each frequency can be reduced, while the signal component remains the same.

In summary, the present invention improves a performance of LCI and OCT, and as a result, can be used in developing LCI and OCT diagnostic technologies for medical and non-medical applications.

According to certain exemplary embodiment of the present invention, logic arrangement to provide data associated with optical imaging of at least one portion of a sample. For example, when executed by a processing arrangement, the processing arrangement can be configured to receive signals that correspond to spectral bands of more than one electromagnetic signals from a detecting arrangement. The detecting arrangement can detect the spectral bands that are separated from the electromagnetic signals by a spectral separating arrangement. The spectral separating arrangement can receive the electromagnetic signals from an interferometer, and the electromagnetic signals may be associated with characteristics of at least one of a plurality of portions of the sample. At least two of the portions of the sample may be irradiated simultaneously. The spectral bands can be generated as a function of the electro-magnetic radiation which is associated with at least one electromagnetic radiation received from a transmissive reference. Further, the data can be generated based on information corresponding to the received signals. A storage medium including executable instructions thereon to provide data associated with optical imaging of such portion of the sample can also be provided. For example, when the executable instructions are executed by the processing system, the executable instructions can configure the processing system to execute the procedures described herein above.

Other features and advantages of the present invention will become apparent upon reading the following detailed description of embodiments of the invention, when taken in conjunction with the appended claims.

BRIEF DESCRIPTION OF THE DRAWINGS

The invention is illustrated in the drawings in which like reference characters designate the same or similar parts throughout the figures of which:

FIG. 3 is a schematic view of a system with one detector array according to one embodiment of the present invention.

FIG. 4 is a detail of a probe.

FIG. 5 is a schematic view of separating unit in combination with two integrating CCD arrays for detection of the dual-balanced wavelength demultiplexed signal.

FIG. 6 is a schematic view of a preferred embodiment of a standalone system

FIG. 9 is a schematic view of using beam recombination to provide one dimension of interference information along one dimension of a two-dimensional detector array, while performing wavelength separating along the other dimension of the two dimensional array.

FIG. 14 is a graph of a typical interference patter as a function of path length difference between sample arm and reference arm.

FIGS. 15A-C are flow diagrams of a method.

FIG. 17 is a graph of frequency versus amplitude spectrum subtracted from the shot noise (experimental data) for the N=1 (dotted line) and N=⅓ (solid line) cases.

FIG. 18 is a graph of power density for the full spectrum as a function of frequency.

FIG. 19 is a graph after subtraction of the shot noise levels.

FIG. 20 is a graph after processing the signals.

DETAILED DESCRIPTION OF THE PREFERRED EMBODIMENTS

Overview

Certain exemplary embodiments of the present invention include a hybrid method that implements aspects of LCI and OCT where the reference arm is scanned, and spectral radar, which does not require reference arm scanning.

In one embodiment, the signal in the detection arm of an OCT system is split into more than one spectral band before detection. Each spectral band is detected by a separate photodetector and amplified. For each spectral band, the signal can be band pass filtered around the signal band by analog electronics and digitized, or, alternatively, the signal may be digitized and band pass filtered in software. As a consequence, the shot noise contribution to the signal can be reduced by a factor equal to the number of spectral bands, while output of the signal remains the same. The reduction of the shot noise increases the dynamic range and sensitivity of the system.

In another exemplary embodiment of the present invention, an apparatus is provided for spectral radar that does not require reference arm scanning. For many detectors, no ranging or reference arm scanning is needed, and the method may be similar to the method which can be employed for a spectral radar except that phase information of the cross spectral density is preferably preserved.

In other exemplary embodiments, the present invention describes an arrangement for spectral radar that eliminate phase instability in the interferometer, obtaining the complex spectral density and eliminating auto correlation noise on the sample arm light, relative intensity noise, and 1/f noise.

Theory

Time Domain Versus Spectral Domain OCT

Nearly all conventional OCT systems are based on Time Domain scanning. In such conventional systems, the length of the reference arm in a Michelson interferometer is rapidly scanned over a distance corresponding to the imaging depth range. An alternative procedure to scanning the reference arm, is one that measures the cross-spectral density at the detection arm of the Michelson interferometer using a spectrometer. In Spectral Domain OCT, no mechanical (e.g., motionless) scanning of the reference arm is required, while an apparatus for generating a phase shift can be used. Only recently was it recognized that a significant signal to noise gain can be achieved by direct measurement of the cross-spectral density.

Figure 1:
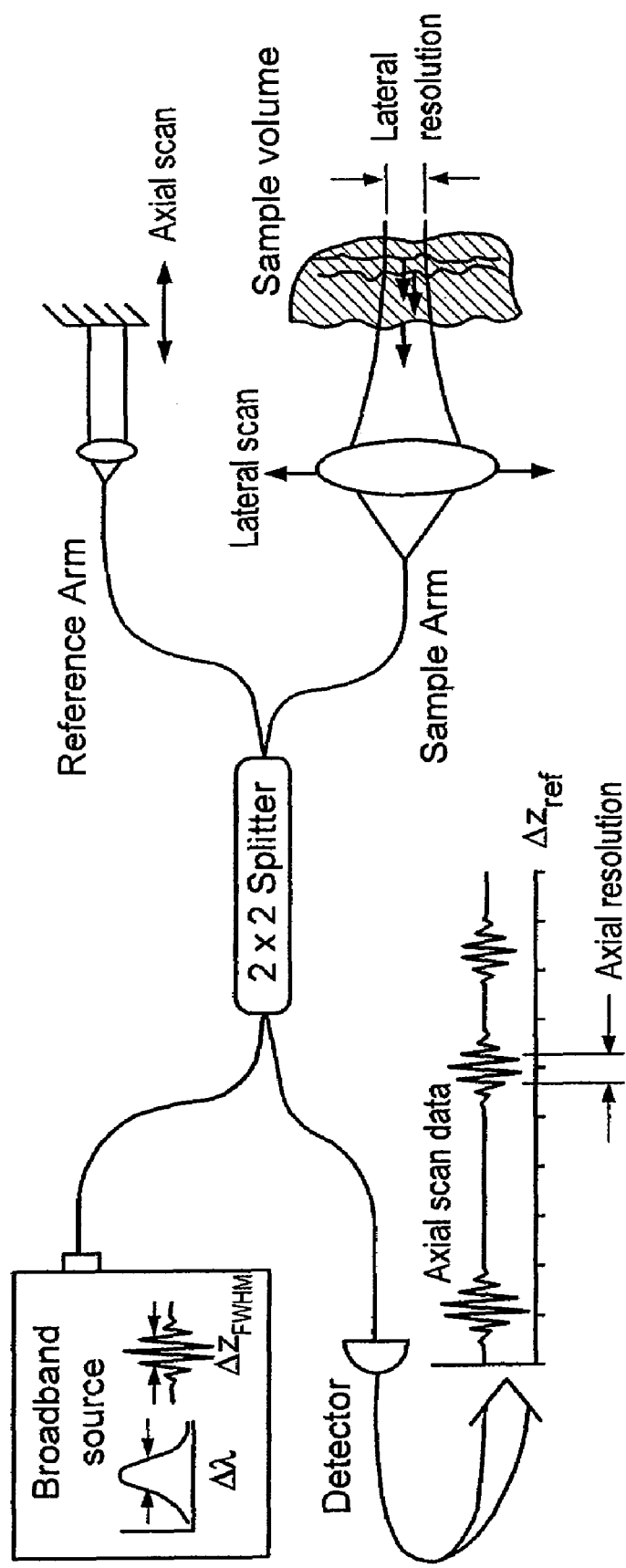
FIG. 1 is a schematic view of a conventional system.

FIG. 1 shows a schematic of a conventional Time Domain OCT system. On scanning the reference arm path length, interference fringes are formed corresponding to positions that match the distance to the three structures drawn in the sample volume. A single detector is used to detect the interference fringes. By envelope detection of the fringe patterns, an image is constructed that maps tissue reflectivity to a given location.

Certain exemplary embodiments of the present invention provide a detection principle based on Spectral Radar concepts (further referred to as Spectral Domain OCT) or a hybrid method between Spectral Domain and Time Domain OCT that can be more sensitive than current state of the art Time Domain OCT, allowing a substantial increase in the acquisition speed to resolution ratio.

Principle of Shot Noise Reduction in Spectral Domain OCT

The best signal to noise performance of Time Domain OCT systems is obtained when the noise is shot noise limited. Shot noise can be reduced significantly by replacing the single element detector with a multi-element array detector. When the detection arm light is spectrally dispersed on the array detector, each element of the array detects a small wavelength fraction of the spectral width of the source. The shot noise is preferably reduced by a factor equal to the number of elements of the array. The principle of the signal to noise improvement is based on the white noise characteristic of shot noise and the observation that only electromagnetic waves of the same wavelength produce interference fringes.

The shot noise power density $N_{shot}(f)$ (in units [W/Hz], [A$^2$/Hz] or [V$^2$/Hz]) is proportional to the current (or equivalently the optical power times the quantum efficiency) generated in the detector. For a monochromatic beam of wavelength $\lambda_1$ entering the interferometer, the fringe frequency or carrier f at the detector is determined by the velocity v of the mirror, $f_1=2v/\lambda_1$. The shot noise is proportional to the power (or spectral density $S(\omega)$) at wavelength $\lambda_1$. A second wavelength $\lambda_2$ is preferably coupled into the interferometer. A second fringe frequency or carrier at frequency $f_2=2v/\lambda_2$ is simultaneously present. The shot noise at this second frequency is preferably the sum of the shot noise generated by the optical power at wavelength $\lambda_1$ and $\lambda_2$. Also, at frequency $f_1$ the shot noise is the sum of the shot noise generated by the optical power at wavelength $\lambda_1$ and $\lambda_2$. Thus, at both frequencies a cross-shot noise term is generated by the simultaneous presence of both wavelengths at the detector. By spectrally dispersing each wavelength to a separate detector, the cross shot noise term can be eliminated. In this way, Spectral Domain OCT offers a significant improvement of signal to noise ratio over Time Domain OCT systems.

Signal to Noise Analysis of Time Domain Versus Spectral Domain OCT.

Signal

Analysis of the Signal to Noise Ratio (SNR) in Time Domain OCT has been described in related publications. The interference fringe peak amplitude in time domain OCT is given by $$I_{peak} = \sqrt{P_{ref} P_{sample}}, \quad (1)$$

with $P_{ref}$, $P_{sample}$ the reference and sample arm power in Watts, respectively. In terms of electrical power at the detector, the signal in units [A$^2$] is defined as $$S = \eta^2 e^2 P_{ref} P_{sample}/E_v^2, \quad (2)$$

with $\eta$ the quantum efficiency, e the charge quantum and $E_v=hc/\lambda$ the photon energy. The reference and sample arm powers are given by the respective reflected spectral densities, $$P_{ref,sample} = \int S_{ref,sample}(\omega) d\omega. \quad (3)$$

Assuming that the reference and sample spectral densities are equal to the source spectral density $S(\omega)$, where the sample arm spectral density is attenuated by a large factor, i.e., $S_{ref}(\omega)=S(\omega)$, $S_{sample}(\omega))=\alpha S(\omega))$ with $\alpha<<1$, and inserting the above expression of reference and sample arm into the original definition of the signal gives, $$S = \eta^2 e^2 \alpha \left[\int S(\omega) d\omega\right]^2 / E_v^2. \quad (4)$$

Thermal, Shot Noise and Relative Intensity Noise Contributions

Three contributions to the total noise of OCT signals are: thermal noise, shot noise and relative intensity noise. Thermal noise is generated by the feedback resistor, shot noise is related to the finite nature of the charge quantum resulting in statistical fluctuations on the current, and relative intensity noise is related to the temporal fluctuations due to chaotic character of classical light sources. These three contributions to the noise density in units [A$^2$/Hz] are given by, $$N_{noise}(f) = \frac{4kT}{R_{fb}} + \frac{2\eta e^2 P_{ref}}{E_v} + 2\left(\frac{\eta e P_{ref}}{E_v}\right)^2 \tau_{coh}, \quad (5)$$

k is Boltzmann's constant, T the temperature in Kelvin, $R_{fb}$ the value of the feedback resistor, and $\tau_{coh}$ the coherence time of the source. Coherence time is related to the full spectral width at half maximum $\Delta\lambda$ of a Gaussian source by the following relation, $\tau_{coh}=\sqrt{2\ln2/\pi}\lambda_0^2/(c\Delta\lambda)$. Shot noise limited detection is achieved when the second term in Eq. (5) dominates the other noise contributions.

Signal to Noise Ratio (SNR)

The signal to noise ratio (SNR) is given by $$SNR = \frac{S}{N_{noise}(f)BW}, \quad (6)$$

with BW the signal bandwidth, and parameters S and $N_{noise}(f)$ as described above.

Space and Frequency Domain Description of the OCT Signal

The OCT signal is most easily described in the space domain. For a single object in the sample arm, the interference term of the OCT signal is proportional to the real part of the Fourier transform of the source spectrum $S(\omega)$, $$I(\Delta z) \propto \text{Re} \int \exp(ik\Delta z) S(k) dk, \quad (7)$$

with $\Delta z$ the path length difference between sample and reference arm and k the wave vector. As a function of time, the OCT signal is given by, $$I(t) \propto \text{Re} \int \exp(2i\omega t v/c) S(\omega) d\omega, \quad (8)$$

with v the reference arm mirror velocity. The frequency spectrum of the signal is given by a Fourier transform of the signal in the time domain, resulting in a complex function. The absolute value of this function is equal to the spectral density, $$|I(f)| = |\int I(t) e^{2i\pi f t} dt| = S(\pi f c/v), \quad (9)$$

which shows that the signal bandwidth is directly proportional to the source spectral width and scales linearly with the reference arm mirror velocity, i.e., imaging speed. Eq. (9) also directly relates the absolute value of the frequency spectrum, $|I(f)|$, to the signal S (Eq. (4)).

Eq (9) also demonstrates that each angular frequency of the light source or equivalently each wavelength of the source is represented at its own frequency in the measured interferometric signal. The depth profile information I(t) can be obtained from the complex cross spectral density I(f) by a Fourier transform.

The complex cross spectral density can also be obtained by splitting the signal I(t) in several spectral bands using a dispersive or interferometric element. At each detector, only part of the complex cross spectral density is determined. Combining the cross spectral densities of each detector, the full spectral density of the signal is retrieved.

Thus, the same information can be obtained by separating spectral components to individual detectors. Combining the signal of all detectors in software or hardware would result in the same signal as obtained with a single detector.

Signal to Noise Gain with Spectral Domain OCT

In the detection arm, the spectrum can be split into two equal halves, where two detectors each detect one half of the spectrum. According to Eq (9), the frequency spectra at detectors 1 and 2 are given by $|I_1(f)|=S(\pi f c/v)$ for $f<f_0$, $I_1(f)=0$ for $f>f_0$ and $I_2(f)=0$ for $f<f_0$, $|I_2(f)|=S(\pi f c/v)$ for $f>f_0$, respectively. The frequency spectrum as would be acquired by a single detector in time domain OCT is given by the sum of $I_1(f)$ and $I_2(f)$; $I(f)=I_1(f)+I_2(f)$. Thus, the signal S after combining the spectra is equal, however $I_1(f)=0$ for $f>f_0$ and $I_2(f)=0$ for $f<f_0$, the bandwidth BW per detector can be reduced by a factor of 2.

The noise is determined by the sum of the shot noise contributions at detectors one and two. From Eqs. (5) and (6), the shot noise per detector is proportional to the reference arm power at the detector times the bandwidth for the detector. Since the spectrum was split in equal halves, the reference power at detectors 1 and 2 is, respectively, $$P_{ref}^1 = 0.5 P_{ref}, \quad P_{ref}^2 = 0.5 P_{ref} \quad (10)$$

The sum of the shot noise contribution for the two detectors is, $$N_{noise}^{SD} \propto P_{ref}^1 \times 0.5 BW + P_{ref}^2 \times 0.5 BW = 0.5 P_{ref} BW, \quad (11)$$

which may compared with the shot noise of a single detector in time domain OCT, $$N_{noise}^{TD} \propto P_{ref} BW. \quad (12)$$

Thus, by spectrally dispersing the detection arm light over two separate detectors, the signal remains the same, while the noise is reduced by a factor of 2, resulting in a net SNR gain by a factor of 2.

Extending the above analysis, it can be demonstrated that the shot noise contribution is reduced by a factor equal to the number of detectors. The sum of shot noises for N detector elements, where each detector element receives one $N^{th}$ of the total reference power, is given by, $$N_{noise} = \frac{2\eta e^2 P_{ref}}{E_v} \frac{BW}{N}. \quad (13)$$

The signal is the same as in Time Domain OCT, and the SNR ratio for Spectral Domain OCT is given by, $$\frac{S}{N_{noise}} = \frac{\eta P_{sample} N}{2 E_v BW}. \quad (14)$$

Thus Spectral Domain OCT enables a SNR improvement over Time Domain OCT of a hundred to a thousand fold, depending on the number of detector elements N. Using a charge coupled array or an integrating device as a detector, such as, but not limited to, a line scan camera, the ratio N/BW is replaced by the integration time $\tau_i$ of the array, which results in, $$\frac{S}{N_{noise}} = \frac{\eta P_{sample} \tau_i}{2 E_v}. \quad (15)$$

Advantages

The exemplary embodiment of the present invention reduce shot noise and other forms of noise which allows for much lower source powers, or much higher acquisition rates than current systems. The increased detection sensitivity allows for real time imaging. Such imaging speed can help practitioners where motion artifacts are a continuing problem, such as in gastrointestinal, ophthalmic and arterial imaging environments. By increasing the frame rate while maintaining or improving the signal to noise ratio such artifacts can be minimized. The present invention also enable one to screen large areas of tissues with OCT and allows clinical viable screening protocols using this method.

Figure 2:
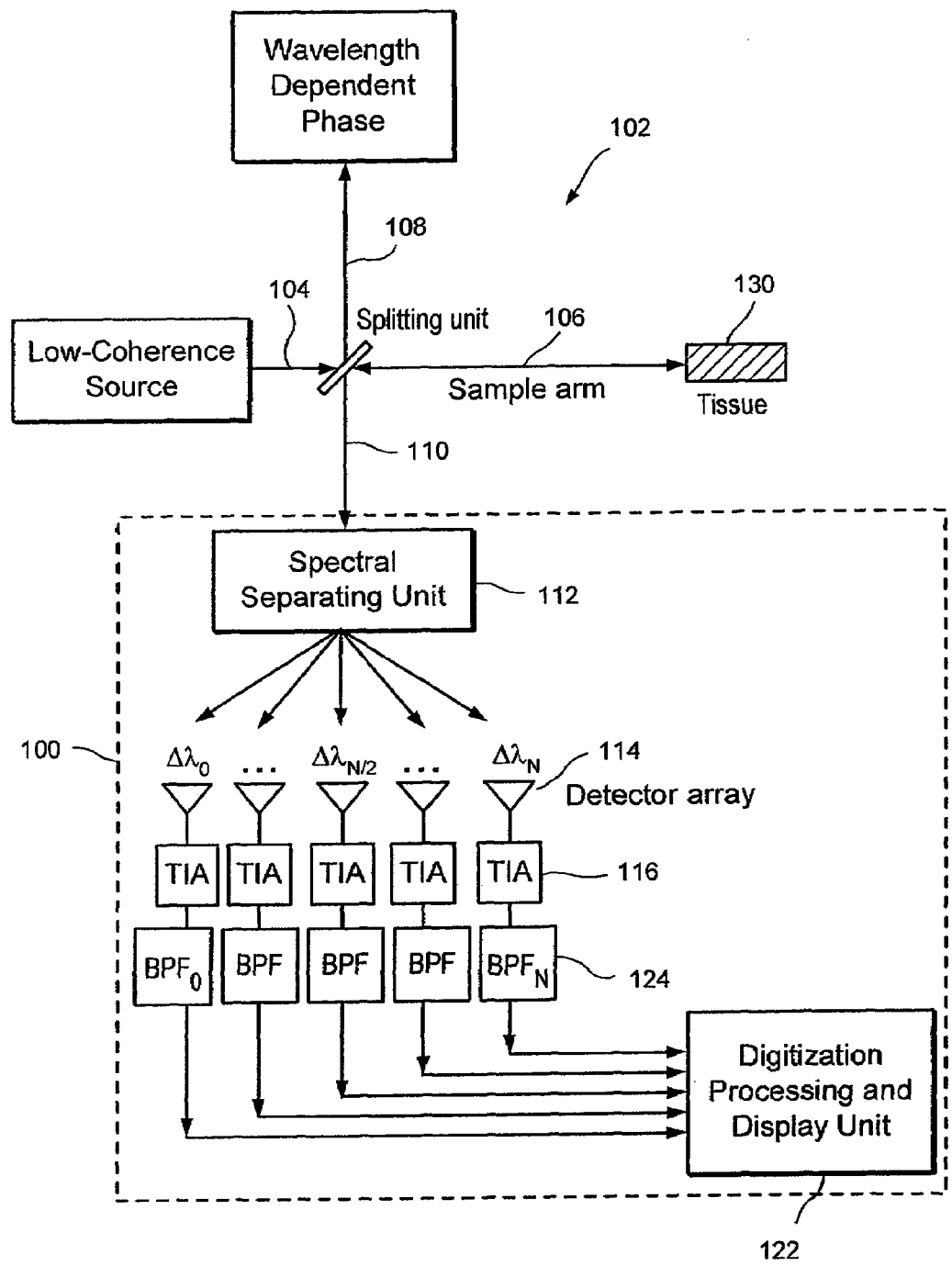
FIG. 2 is a schematic view of a preferred embodiment of the parallel detection scheme for LCI.

FIG. 2 shows a top level system 100 configuration according to an exemplary embodiment of the present invention, which comprises an interferometer 102 with a source arm 104, a sample arm 106, a reference arm 108, and a detection arm 110 with a spectral separating unit 112, multiple detectors 114, amplifiers 116, optional analog processing electronics 118 (not shown, but known to those skilled in the art), and A/D converters 120 (not shown, but known to those skilled in the art) for conversion of signals. A processing and display unit 122 has optionally digital band pass filtering ("BPF") units 124, Digital Fast Fourier Transforms ("FFTs") 126 (not shown), coherent combination of signals, and data processing and display algorithms. The detector array 114 may be 1×N for simple intensity ranging and imaging and/or Doppler sensitive detection, 2×N for dual balanced detection, 2×N for simple intensity ranging and/or polarization and/or Doppler sensitive detection, or 4×N for combined dual balanced and polarization and/or Doppler sensitive detection. Alternatively, an M×N array may be used for arbitrary number "M" of detectors 114 to allow detection of transverse spatial information on the sample 130.

FIG. 3 shows a schematic of one exemplary embodiment of a Spectral Domain OCT system 200, which includes a light source 202, splitter 204, reference arm 206, sample arm 208, tissue sample 130, optical element 210, grating 212, lens 214, detector 216 array, and processor 218. The detection arm light is dispersed by the grating 212 and the spectrum imaged onto a detector array 216. By stepping the reference arm 206 length over a distance $\lambda/8$, the cross spectral density of reference arm 206 and sample arm 208 light can be determined. A Fourier transform of the cross spectral density generates the depth profile information.

Sources

The source arm 203 contains at least light source 202 that is used to illuminate the interferometer with low-coherence light. The source temporal coherence length is preferably shorter than a few microns (a preferred range is about 0.5 µm-30 µm). Examples of sources include, but are not limited to, semiconductor optical amplifier, superluminescent diodes, light-emitting diodes, solid-state femtosecond sources, amplified spontaneous emission, continuum sources, thermal sources, combinations thereof and the like. Other appropriate sources known to those skilled in the art may be used. While light is referred to herein as the source, it is intended that other electromagnetic radiation ranges may be suitable for use, depending on the circumstances.

Interferometer

The sample arm 208 collects light reflected from the tissue sample 130 and is combined with the light from the reference arm 206 to form interference fringes. The reference arm 206 returns light back to be combined with the source arm 203. The reference arm can also be transmissive with no reflection. This action of beam splitting/recombining may be performed using a beam splitter 204 (Michelson), or circulator(s) (Mach-Zehnder) or other means known to those skilled in the art for separating a beam into multiple paths and recombining these multiple beams in a manner that interference between the beams may be detected. The splitting may be accomplished in free space or by using a splitter 204 having passive fiber optic or waveguide components.

Sample Arm

For LCI applications, the sample arm may be terminated by an optical probe comprising a cleaved (angled, flat, or polished) optical fiber or free space beam. A lens (such as, but not limited to, aspherical, gradient index, spherical, diffractive, ball, drum or the like) may be used to focus the beam on or within the sample. Beam directing elements (such as, but not limited to, mirror, prism, diffractive optical element or the like) may also be contained within the probe to direct the focused beam to a desired position on the sample. For OCT applications, the position of the beam may be changed on the sample as a function of time, allowing reconstruction of a two-dimensional image. Altering the position of the focused beam on the sample may be accomplished by a scanning mirror (such as, but not limited to, a galvanometer, piezoelectric actuator or the like), electrooptic actuator, or moving the optical fiber (for example, rotating the optical fiber, or linearly translating the optical fiber). The sample arm probe may be a fiber optic probe that has an internally moving element where the motion is initiated at a proximal end of the probe and the motion is conveyed by a motion transducing arrangement (such as, but not limited to, wire, guidewire, speedometer cable, spring, optical fiber and the like) to the distal end. The fiber optic probe may be enclosed in a stationary sheath which is optically transparent where the light exits the probe at the distal end. FIG. 4 shows a detail view having an inner cable 260 (which may rotate or linearly translate along the axis of the probe), an outer transparent or semi-transparent sheath 262, distal optics 264, and remitted light 266 (which may be at any angle with respect to axis of catheter).

Reference Arm Delay

A mechanism 270 in the reference arm 206 allows for scanning the group delay of the reference arm 206. This group delay can be produced by any of a number of techniques known to those skilled in the art, such as, but not limited to, stretching an optical fiber, free space translational scanning using a piezoelectric transducer, or via a grating based pulse shaping optical delay line. Preferably, the delay is introduced by a non-mechanical or motionless arrangement. By "non-mechanical" it is meant that no mechanically moving parts are utilized. The absence of mechanically moving parts is believed to reduce the known deficiencies of using mechanical devices to introduce delay. As opposed to traditional LCI or OCT systems described in the literature, the reference arm 206 in the present invention does not necessarily need to scan over the full ranging depth in the sample, and preferably scans over at least a fraction of the ranging depth equal to one over the number of detectors (1/N). This scanning feature is fundamentally different from known delay scanning schemes used in conventional known LCI and OCT systems. The reference arm 206 optionally has a phase modulator mechanism (described more fully herein), such as, but not limited to, an acoustooptic modulator, electrooptic phase modulator or the like, for generating a carrier frequency. In order to reduce the scan range of the reference arm 206, the spectrum is preferably split into a plurality of spectral bands according to a method that will be explained below.

Detection

Referring to FIG. 2, in the detection arm 110 spectral separating unit separates the spectral components and the signal is forwarded to separate detectors 114. The detectors 114 may preferably consist of photodiodes (such as, but not limited to, silicon, InGaAs, extended InGaAs, and the like). Alternatively, a one or two dimensional array of detectors 114 (such as, but not limited to, photodiode array, CCD, CMOS array, active CMOS array, CMOS "smart pixel" arrays, combinations thereof and the like) may be employed for detection. Two detectors 114 for each spectral band may be used for polarization sensitive detection following separation of the recombined light into orthogonal polarization eigenstates. Detector 114 arrays may be 1×N for simple intensity ranging and imaging and/or Doppler sensitive detection, 2×N for dual balanced detection, 2×N for intensity ranging and imaging and/or polarization sensitive and/or Doppler sensitive detection, or 4×N for combined dual balanced and intensity ranging and/or Doppler sensitive and/or polarization sensitive detection. Alternatively, an M×N array may be used for arbitrary M to allow detection of transverse spatial information on the sample 40.

Detector signals can be amplified by Trans Impedance Amplifiers ("TIAs") 116, band pass filters 124 (digitally or using analog circuitry) and digitized by A/D converters and stored in a computer 122 for further processing. Each detector 114 is preferably configured to be shot noise limited. Shot noise limited detection is preferably achieved by adjusting the intensity of light returned from the reference arm 108 so that the shot noise dominates over the thermal noise of the resistor in the TIA 116 and is higher than the relative intensity noise ("RIN"). Each detector 114 is balanced for such dual noise reduction.

In one embodiment of the present invention, the number of detectors 114, N can be in the range of 2-10,000 or more. A preferred range of N is about 8-10,000 detectors. In one preferred embodiment, eight detectors 114 (or a number in that area) can provide real time, or close to real time, imaging.

Alternatively, another way for detection includes an integrating one-dimensional or two-dimensional detector 114 array which is capable of obtaining images at a rate preferably greater than 1/f noise (f=frequency) (see FIG. 5). Optionally, the BPF can be implemented discretely following digitization. An additional modification includes using an optional second detector 115 array for balanced detection which allows increased reference arm power and acquisition speed due to reduction of RIN and 1/f noise. In a preferred embodiment, a phase tracking apparatus and/or algorithm is used in the reference arm 108 to reduce signal attenuation due to fringe instability.

This system could be implemented using a single detector 114 with dual-balanced detection enabled by either interleaving dual balanced rows of the array detector or by placing two similar array detectors adjacent to one another. If two array detectors 114 and 115 are used, the values are subtracted from one another to achieve dual balance detection. If more than two array detectors are used the signals can be selectively subtracted and complex spectral density can be obtained.

The spectral intensity as a function of wavelength is preferably constant. However, if it is not, the spectrum can be shaped in the reference, sample and/or source arms to make it constant. Spectral shapers are known in the art.

Processing

The signal of each detector 114 is band pass filtered around the signal frequency, such as by FFT's. The signal of all detectors 114 can be combined as explained hereinabove to obtain the complex cross spectral density in the frequency domain. By Fourier transform, the complex cross spectral density can be converted to a depth profile in the tissue. Several methods to process the complex spectral density to obtain depth profile information are known to those skilled in the art, such as, but not limited to, by obtaining at least two signals with a pi/2 phase shift in the reference arm and then reconstructing the complex spectral density by some linear combination of the two signals.

Following detection analog processing includes a trans impedance amplifier, band pass filter, and digitization of the signal. This signal may then be converted to reflectivity as a function of depth by the Fourier transform operation. Digital processing includes digitization, digital band pass filtering in either the frequency domain or time domain (FIR or IIR filter) and inverse Fourier transformation to recover the tissue reflectivity as a function of depth.

System Integration

Processing of the multiple signals may be performed using an imaging or diagnostic console which performs basic operations including, mathematical image reconstruction, display, data storage. Alternatively, another embodiment, shown in FIG. 6, shows a standalone detection and processing system 300 that may be connected to OCT and/or LCI systems already in use. In this case, the detector 302 and digitization may be performed in the standalone unit. The input to the standalone unit would be the light combined from both reference and sample arms, as previously described. The output of the system would be an interferometric signal similar to previous OCT or LCI console inputs, but with increased SNR. The standalone unit would contain a splitter 304 for splitting the wavelengths into spectral bands, multiple detectors 302, analog electronics, including TIA's 306 and an arrangement for reconstructing the interferometric signal, as previously described. The arrangement for reconstructing the interferometric signal would include either analog or digital arrangement where the analog arrangement includes band pass filters ("BPF's") 308, and analog arrangement for adding the individual interferograms from each wavelength band. The digital arrangement would include an analog to digital converter, and a CPU 310 capable of recombining the interferograms from each spectral band into a single full bandwidth interferometric signal. The reconstructed interferogram may be then the output of the standalone system or alternatively, the reconstructed interferograms demodulated signal may be used as the input to the pre-existing system console.

Scan Range of the Reference arm.

The ranging depth in the sample 130 is determined by the resolution with which the cross spectral density can be determined. In a method using a single detector the spectral resolution of the complex spectral density is determined by the scan range of the reference arm. The larger the scan range, the higher the spectral resolution and the larger the ranging depth in the sample. In a system with a spectral separating unit and multiple detectors, the resolution of the cross spectral density is a combination of reference arm scan range and spectral separating characteristics.

Any suitable wavelength band shape may be used for separating. For arbitrary spectral band shapes, the scan range of the reference arm 18 is determined by the delay that is needed to completely resolve the spectral components in each band.

Figure 7:
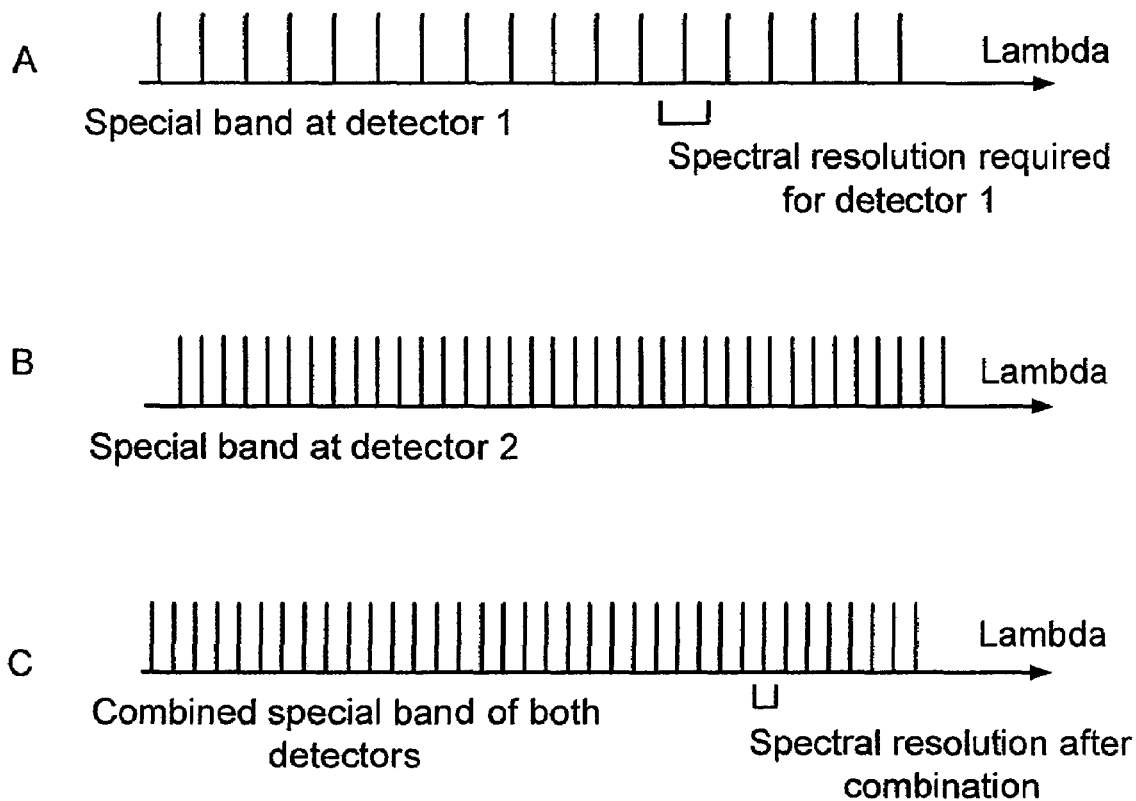
FIG. 7 is a schematic view showing spectral separating into 2 bands.
Figure 8:
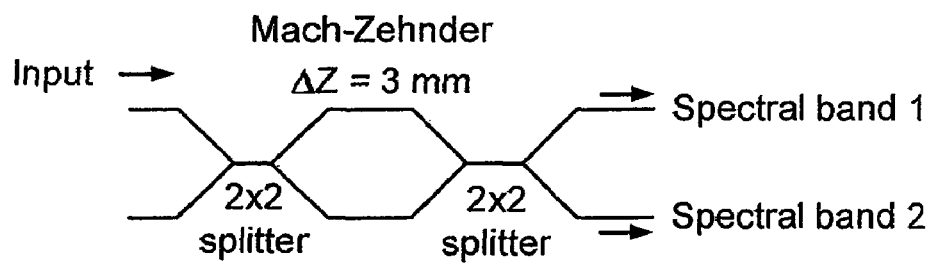
FIG. 8 is a schematic of spectral separating into 4 bands. The spectral resolution preferably used for each detector is twice as coarse as in the case of multiplexing into 2 bands.

For instance, in one preferred embodiment, as depicted in FIG. 7, a spectral separating unit can split the spectrum into two bands where each band consists of a set of narrow spectra in a comb-like structure. FIG. 7A shows the spectral band at detector #1. FIG. 7B shows the spectral band at detector #2. FIG. 7C shows the combined spectral band of both detectors. Interleaving the comb-like spectral bands of each detector 24 gives back a continuous spectrum. The resolution needed to resolve the spectrum at an individual detector is half of what it would need to be in a single detector system, and thus the scan range of the reference arm can be reduced by a factor of two, while maintaining the same ranging depth in the sample 130. In an alternative embodiment, the spectral separating unit can be in the reference arm. In FIG. 8 an example is shown for splitting up the spectrum in several spectral bands. In this example the scan range of the reference arm can be reduced by a factor relating to the number of spectral bands while maintaining the same ranging depth in the sample.

Embodiments of the Wavelength Separating Filter

Several techniques are known to separate or disperse the spectrum. One method uses a grating and a micro lens array to focus spectral components onto individual detectors. A second method uses prisms instead of a grating. A third method uses a grating and an addressable mirror array (such as, but not limited to, a "MEMS" mirror or digital light processing ("DLP") apparatus or the like) to direct spectral components to individual detectors. A fourth method uses a linear array of optical filters prior to the array of individual detectors. A fifth method uses waveguides etched into a material or manufactured from fiber optic components to generate a pattern with the desired filter action. As an example, in FIG. 8 an exemplary embodiment of a wave guide filter is provided that splits the spectrum into bands. A sixth method would use arrayed waveguide gratings ("AWG") to create the interleaved or arbitrary spectral bands.

Relative Intensity Noise

One of the noise terms that is present at the detectors is relative intensity noise ("RIN") or Bose-Einstein noise. RIN noise likely becomes dominant over shot noise for spectral widths less than a few nanometers. For many detector configurations, the spectral width at each detector may likely be smaller than a few nanometers, and the relative intensity noise can dominate the overall system noise. Thus, balanced detection, can preferably be implemented to eliminate the RIN. Several methods known in the art exist to implement balanced detection. One such method will be discussed below in further detail. For example, but not by way of limitation, as shown in FIG. 9, light from the reference arm 400 and sample arm 402 is incident on a grating 404 at slightly different angles and reflected and focused onto a linear N×M photo detector array 406. Along the N direction (column) of the array, wavelength is encoded. Along the M direction (row) of the array, the interference pattern of the sample and reference arm at a particular wavelength is recorded. Since sample and reference arm light were incident at slightly different angles, a pattern of interference maxima and minima will be present in the column direction. Balanced detection can be implemented by subtracting diode signals that are exactly out of phase with respect to the maxima and minima pattern. Alternatively, balanced detection can be implemented by measuring the amplitude of the interference pattern in the column direction which may be accomplished by subtracting the maxima or the interference pattern from the minima of the interference pattern along the column. An alternative embodiment for balanced detection is combining the reference and sample arm light 400, 402 to produce two outputs that have interference signals with a π phase shift between them. This may be accomplished by taking both output ports of a beam splitter or other beam-recombining element. The two signals may then be detected separately and subtracted. Since the signals that contain the interference terms are shifted by π in phase, these terms add constructively upon the operation of subtraction. The portion of signal that contains RIN, however, cancels upon subtraction. The subtraction operation can occur for all M elements and be conducted in the analog or digital domain. If subtraction is performed in the analog domain, the bandwidth of the signal is reduced by a factor of 2, preferably decreasing specified parameters of the digitization and data transfer across the computer bus.

Figure 10:
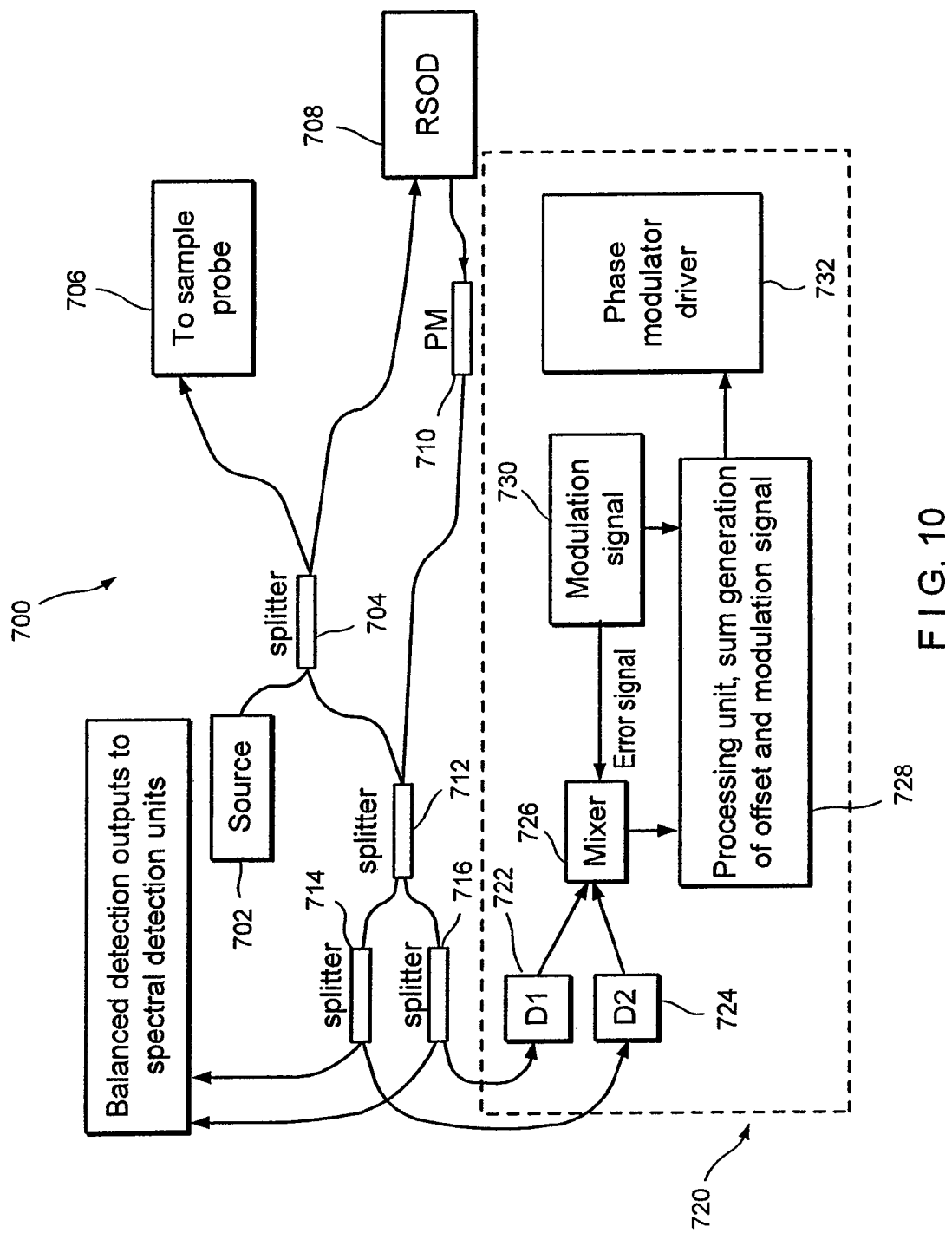
FIG. 10 is a schematic view of a phase tracking system according to one embodiment of the present invention.

An example of such balanced detection is shown in FIG. 10, which is described more fully hereinbelow. The balance detection outputs are subtracted to generate a balanced signal that cancels RIN.

Signal Processing to Reconstruct the Signal after Spectral Separating and Detection.

Two cases will be discussed below as nonlimiting illustrations of exemplary embodiments of the present invention, firstly the case of continuous spectral bands (blocks), and secondly the comb-like spectral bands as depicted in FIG. 7

Case A: Continuous spectral bands.

The detection arm light is split into N spectral blocks, where each spectral block contains the intensity between two optical frequencies, $$B_N = \int_{\omega_N}^{\omega_{N+1}} S_{ref}(\omega c/2v) d\omega \quad (20)$$

The signal for the full spectral width is obtained by an FFT of the signal in each band, an optional compensation of dispersion and other corrections to the phase and amplitude of each Fourier component to optimize the signal and to correct the spectral density for side lobe reduction, addition of the complex FFT spectra, and inverse FFT on the added complex FFT spectrum, optionally with data reduction before the inverse FFT, to obtain the optionally demodulated function R(t), which is the interferometric response for a depth scan with the full source spectrum.

Case B1: Comb like spectral bands and the reconstruction of the full depth range in the sample arm from reduced reference arm scans.

The following description provided below describes the principle of reconstruction of the full depth range in the sample arm from reduced reference arm scans according to the present invention. The procedure shall be explained in the case of separating the spectrum in two spectral bands. The exemplary method can be expanded for separating into many spectral bands.

The signal at the detector for a single detector system is defined by R(t). The depth range in the sample is given by the measurement time T of a single A-line (depth profile) times the group velocity generated by the reference arm delay line, $z_{range} = v_g T$ The smallest resolvable frequency after an FFT is given by 1/T, which gives a smallest resolvable angular frequency $\Delta\omega = 2\pi/T$. The filter as depicted in FIG. 8 splits the signal into two bands with peaks at $\omega = \omega_0$, $\omega_0 + 2\Delta\omega$, $\omega_0 + 4\Delta\omega$, etc. and $\omega = \omega_0 + \Delta\omega$, $\omega_0 + 3\Delta\omega$, etc., respectively.

$B_1(t)$ and $B_2(t)$ are the signals in band one and two respectively. The signal in spectral bands one and two after Fourier transform are given by $B_1(\omega) = R(\omega)\cos$.

This product in the Fourier domain can also be written as a convolution in the time domain. Assuming the signals periodic with time T, the signals $B_1(t)$ and $B_2(t)$ are given by $B_1(t) = R(t) + R(t+T/2)$ and $B_2(t) = R(t) - R(t+T/2)$.

Using the above equations, the signal R(t) from t=0 to t=T can be reconstructed from the signals $B_1(t)$ and $B_2(t)$ recorded from t=0 to t=T/2 by writing, $R(t) = B_1(t) + B_2(t)$ and $R(t+T/2) = B_1(t) - B_2(t)$ for $0 > t > T/2$. For higher N>2, the identical procedure is performed such that R(t) is reconstructed from $B_1$ to $B_N$.

This demonstrates that the signals $B_1(t)$ and $B_2(t)$ only need to be recorded over half the depth range $Z_{range}$. Thus, the depth ranging in the reference arm can be reduced by a factor of 2, while the ranging depth in the sample remains the same. If the signal is split into more spectral bands, like shown in FIG. 7, a similar procedure as described above allows reduction of the depth scan in the reference arm by a factor of N, while the ranging depth in the sample remains the same, and N the number of spectral bands.

Figure 11:
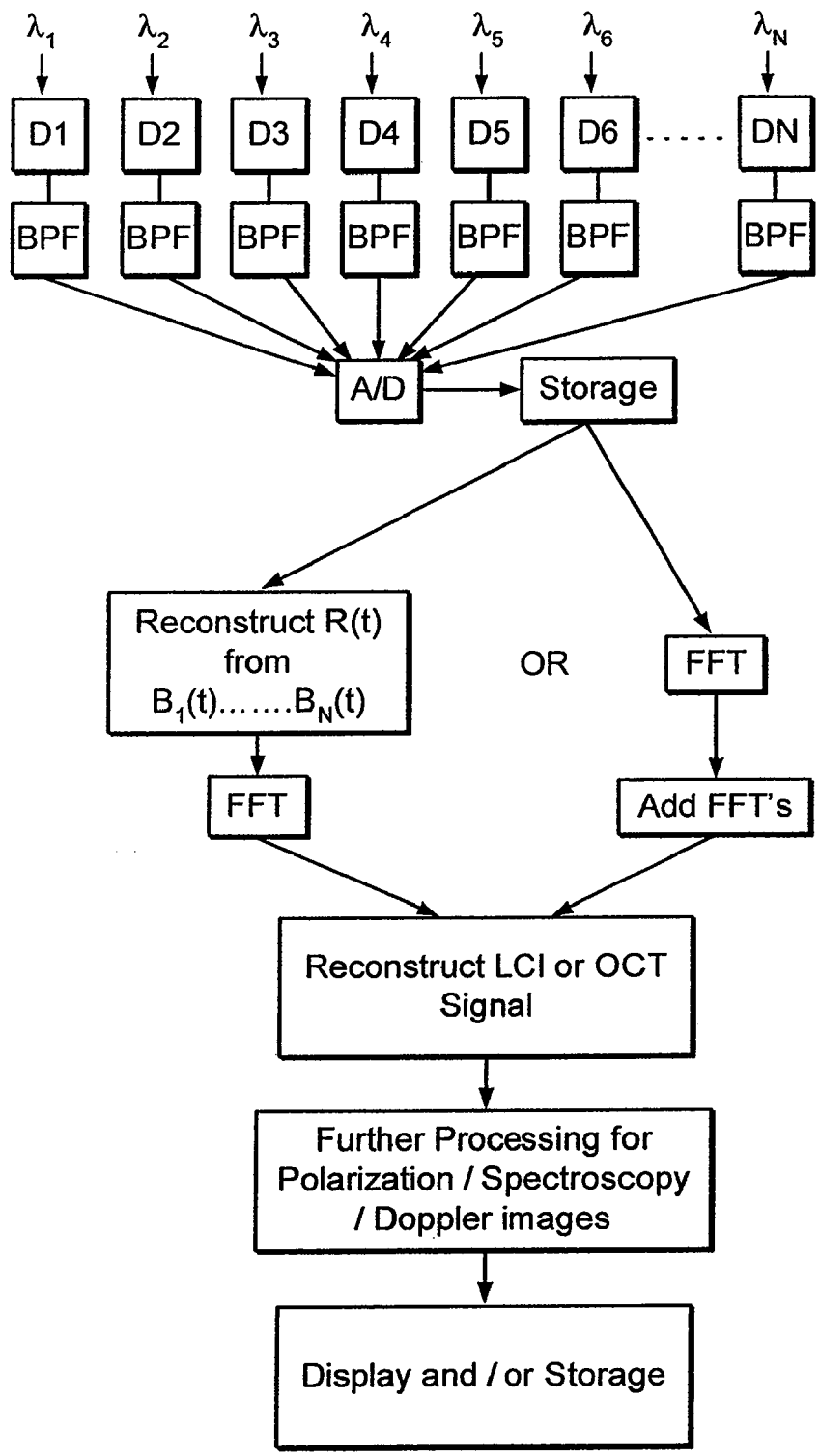
FIG. 11 is a flowchart depicting the reconstruction of LCI or OCT signal from wavelength bands.

An exemplary flow diagram of the procedure described above is shown in FIG. 11.

Case B2. Limit of large number of spectral bands

In the limit of a large number of spectral bands, $$N \geq \frac{L}{\lambda},$$

the optical path length change in the reference arm approaches that of a wavelength, λ. In this limit, only a phase change across one wavelength is needed for reconstructing the entire axial scan over length L. In this case, the reference arm path delay may be accomplished by using any of the aforementioned ways for scanning the reference arm delay. Other preferred methods according to the present invention include insertion of an electrooptic modulator, acoustooptic modulator or phase control rapidly scanning optical delay line ("RSOD") in the reference arm path to impart the path length delay of one wavelength. Also in this case, the wavelength separating unit does not separate the wavelengths into a comb pattern, but separates the spectrum into unique optical frequencies, with each frequency detected by a single detector.

Case C. Fourier domain reconstruction for arbitrary wavelength patterns

In contrast to the reconstruction of the LCI or OCT signal in the time or space domains, the signal may be reconstructed in the Fourier domain by adding the complex spectral components for each wavelength band to compose the Fourier transform of the LCI or OCT signal. Alterations of the phase for each Fourier component may be preferred in certain selected circumstances to correct for minimization of reference arm delay length.

Reconstruction of the Image or One Dimensional Axial Scan

Following reconstruction of the LCI or OCT signal in the real domain, the axial reflectivity may be determined by demodulating the reconstructed LCI or OCT signal. An arrangement for demodulation can include multiplication by a sinusoid and low pass filtering, envelope demodulation using envelope detection, square law demodulation and low pass filtering, quadrature demodulation followed by FIR, IIR filtering, or low pass filtering. In addition, the reconstruction of Stokes vectors (polarization) and flow from these LCI or OCT signals is known to those skilled in the art. Following reconstruction and demodulation, the data may be displayed in one or two-dimensional format (image) for interpretation and ultimately diagnosis of a tissue condition or defect in a medium. If the LCI or OCT signal is reconstructed in the Fourier domain, such reconstructed signal in the Fourier domain can be demodulated in the Fourier domain by shifting the Fourier spectrum and performing an inverse Fourier transform. As a result, the complex signal in the real domain (quadrature signal) is then reconstructed into axial reflectivity information by computing the amplitude of the real portion of the quadrature signal. The complex component is used for computing polarization or flow information. Alternatively, if the signal is reconstructed in the Fourier domain, it can be directly inverse Fourier transformed into the real domain and undergo the aforementioned processing described for the reconstructed real domain signals.

Figure 12:
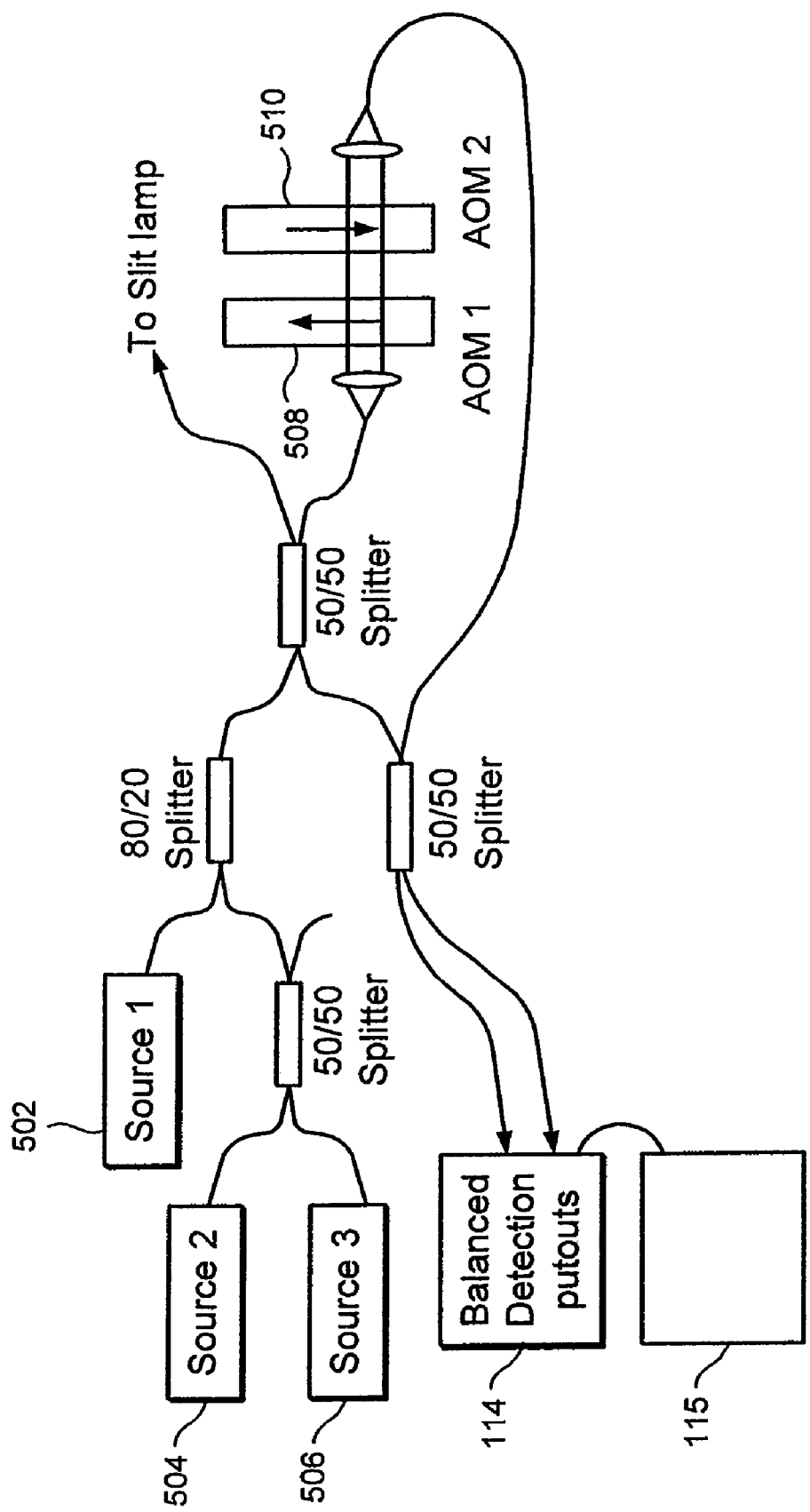
FIG. 12 is a schematic view of a spectral domain OCT interferometer design with a source combining the spectra of several superluminescent sources.

FIG. 12 shows an exemplary embodiment of a Spectral Domain OCT interferometer design 500 showing spectral compounding of light sources 502, 504, and 506 and acousto-optic generation of the carrier in the reference arm. The blocks labeled AOM are acousto-optic modulators 508, 510. The two outputs each go to separate spectral detection units 114, 115 (as depicted in FIGS. 3 and 13) for balanced detection.

After spectral compounding of the source light in the first 50/50 splitter and the 80/20 splitter, light enters a modified Michelson interferometer. A configuration that implements balanced detection is shown. The sample arm goes to the probe (e.g., a slit lamp). Reference arm light is transmitted through two acousto-optic modulators with a difference frequency of 10 kHz to generate a constant carrier frequency that is independent of wavelength. The balanced detection outputs go to separate spectral detection units.

Spectral Detection Unit

Figure 13:
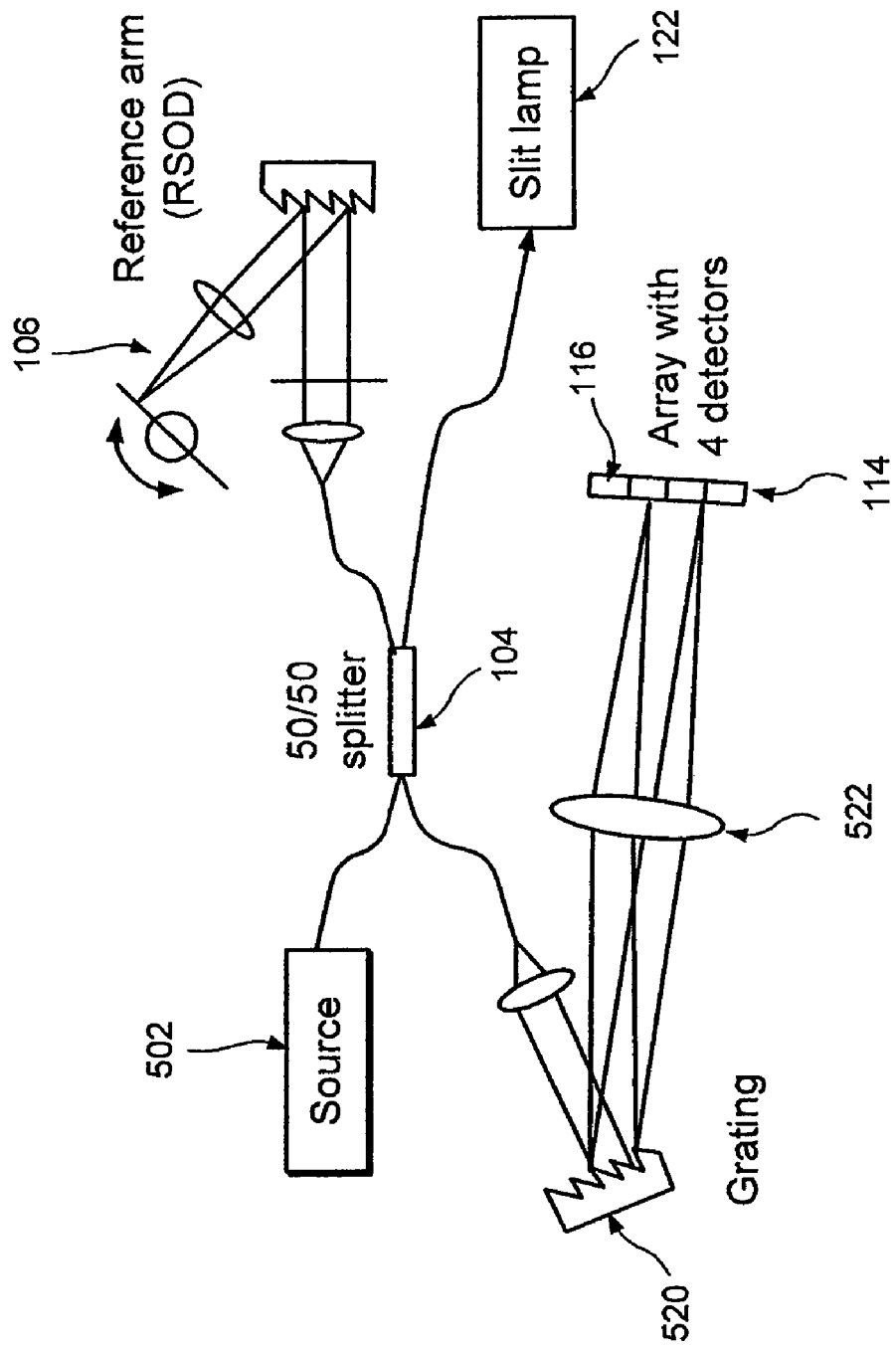
FIG. 13 is a schematic view of a system with a four detector array.

Referring to FIG. 13, the core of Spectral Domain OCT is spectral separation of the detection arm light onto a multi-element array 114. The detection arm beam 520 is spectrally separated by a grating 520 and focused by a lens 522 onto a multi-element array 114.

A scan cameras with N detector elements is used as spectral detection unit 128 (see FIG. 2). Preferably, balanced detection is implemented by adding a second line scan camera. As is known to those skilled in the art, the depth range is inversely proportional to the spectral resolution. When the real part of the complex spectral density is determined, ranging depth z is defined by, $$z = \frac{\lambda_0^2}{4\Delta\lambda}, \quad (18)$$

Line scan rates of 20 kHz can be achieved, allowing demodulation of a 10 kHz carrier to extract the complex cross-spectral density. Data is digitized and transferred to computer memory. Demodulation of the signal is done in software. Scan rates of 10,000 depth profiles per second or more can be achieved.

Dual Balanced Detection

Dual balanced detection is preferably used by the present invention, which is preferably utilized for the following reasons. Firstly, most light sources generate 1/f noise (f=frequency) at relatively low frequencies. Balanced detection will eliminate 1/f source noise. Secondly, an interference term of the sample arm light with itself (auto-correlation term) is present on top of the true signal term, which is the interference between sample and reference arm. This auto-correlation term can be eliminated by a differential technique. Balanced detection may eliminate this auto-correlation term from the measured signal. Thirdly, RIN can be reduced.

Data Acquisition and Processing Unit

The data rate at 20,000 spectral profiles per second, with 2000 detector elements and 8-10 bit resolution (the dynamic range of most line scan cameras) is 40-80 MB/sec. Maximum sustainable data transfer speed over the PCI bus is 100 MB/sec. In a computer with two independent PCI bridges to computer system memory, approximately 200 MB/sec of data can be transferred for real time processing of data from two line scan cameras simultaneously. Implementation of dual balanced detection in analog by subtracting line scan camera signals before digitization may reduce the data rate by a factor of 2. High-speed data acquisition boards are available at resolutions of 12-14 bits and speeds up to 100 M samples/sec. A single 2048 point fast Fourier transform on a 2.5 GHz Pentium 4 processor takes 50 μsec. These numbers show that real-time processing of Spectral Domain OCT data at 20,000 spectral profiles/sec is within reach of current data acquisition and processing power of dual processor PC's. The data collected by the spectrometer can be sampled with equal wavelength increments. Fourier transform, however, links z and k space (or t and w). Because of the non-linear relation between k and λ the spectrum from the spectrometer should be interpolated to create evenly spaced samples in k domain. To achieve the optimal point spread function, dispersion in the sample and reference arm of the interferometer should be balanced. We have shown that dispersion imbalance can be corrected for by digital processing, allowing for correct compensation of dispersion for individual eye lengths.

Phase Tracking

The present invention also provides apparatus and methods for phase tracking in spectral domain ("SD") OCT.

Fully Parallel SD OCT

One of the features of fully parallel SD OCT is spectral dispersion of the detection arm light onto a multi-element array such as but not limiting to an integrating device (e.g., CCD) and measurement of the real or complex spectral density at high speeds. The detection arm beam is separated by a spectral separating unit (e.g., grating) and focused onto the array. With respect to previous Spectral Domain OCT designs known in the art, two differences are apparent that will be discussed below: 1) implementation of balanced detection, and, 2) implementation of phase tracking.

Spectrometer design The depth range in SD OCT is inversely proportional to the spectral resolution. Using the complex spectral density, ranging depth z is given by, $$z = \frac{\lambda_0^2}{2n\Delta\lambda}. \tag{18}$$

Dual balanced detection: Dual balanced detection is advantageous for at least three reasons. First, most light sources generate 1/f noise at relatively low frequencies (tens of kHz range). In time domain ("TD") OCT systems 1/f noise is not a problem because the signal carrier is in general in the MHz range where 1/f noise is not significant. In SD OCT, balanced detection may likely eliminate 1/f source noise. Second, an interference of the sample arm light with itself (auto-correlation term) is present on top of the true signal. This auto-correlation term can be eliminated by a differential technique. Balanced detection can be used to eliminate this auto-correlation term from the measured signal. Third, balanced detection may reduce relative intensity or Bose Einstein noise.

Phase Tracking: Phase tracking is preferable to eliminate phase instabilities in the interferometer. Phase instabilities can cause individual interferometric fringes to shift in location. If detection is slow relative to the shifting of the fringes, the resulting averaging results in an artifactual decrease in the measured fringe amplitude. Fast detection arrays can capture the cross spectral density at a rate of 20 to 40 kHz, resulting in integration times of 50 to 25 µsec, respectively. Phase instabilities arising on a time frame shorter than the integration time of the array should be compensated.

FIG. 14 shows an exemplary interference pattern as a function of path length difference between sample and reference arm.

Phase locking circuitry is common in electronics, and is frequently used in radar and ultrasound. Active phase tracking can be implemented by modulating the interferometer path length difference at 10 MHz with an electro-optic phase modulator in the reference arm over a fraction of the wavelength. By demodulating the intensity measured by one detector at the output of the interferometer at the frequency of the path length modulation, an error signal can be generated indicating in which direction the phase modulator should shift to lock onto a fringe amplitude maximum. By adding an offset to the phase modulator as determined by the error signal, the phase tracker actively locks onto a fringe maximum. The phase modulator can only modulate the path length difference over a few wavelengths. The processing unit can determine if the phase modulator has reached its range limit, and jump by a full wave in phase to maintain lock on a different fringe maximum. This approach exploits the fact that phase should be controlled only modulo $2\pi$. In addition, the processing drives a slower component (e.g., the Rapid Scanning Optical Delay line) to extend the path length range of the phase modulator/RSOD combination over several millimeters. Phase locking can be performed on a fringe maximum, minimum, or zero crossing, based on the type of mixing performed in the demodulation circuit.

The present invention can also use autoranging technology, including processing algorithms, as disclosed in copending U.S. application Ser. No. 10/136,813, filed Apr. 30, 2002, entitled METHOD AND APPARATUS FOR IMPROVING IMAGE CLARITY AND SENSITIVITY IN OPTICAL COHERENCE TOMOGRAPHY USING DYNAMIC FEEDBACK TO CONTROL FOCAL PROPERTIES AND COHERENCE GATING, and commonly assigned to the assignee of the present invention, the disclosure of which is incorporated herein.

The autoranging mechanism may, in one exemplary embodiment, comprise a processor unit for (a) obtaining a first scan line; (b) locating a surface location "S" of a sample; (c) locating an optimal scan range "R" of the sample; (d) modifying a reference arm delay waveform to provide an output; (e) outputting the output to a reference arm; (f) determining whether the image is complete; and (g) moving to the next scan line if the image is not complete or remapping the image using the surface S data and the waveform data stored in the memory storage device if the image is complete.

If the light returned from the sample is of low amplitude, phase locking may be unstable due to the presence of noise. In another embodiment, a separate, preferably monochromatic, light source is input into the interferometer. The separate source wavelength may overlap with the broad bandwidth OCT or LCI source spectrum or may be centered at a different wavelength than the OCT or LCI source spectrum. The separate source is preferably of higher power and may be combined with the source arm (using wavelength division multiplexer, grating, prism, filter or the like) travel to the reference and sample arms and return back to the beam recombining element. The returned separate source light can then be separated from the OCT or LCI light following transmission back through the beam recombining element (i.e. beam splitter output). A separation arrangement can perform spectral separation by a dispersing element, such as a dichroic mirror, filter, grating, prism, wavelength division multiplexer or the like. The separate source will be detected separately from the OCT or LCI broad bandwidth light using one or more detectors. The higher power provided by this separate source can enable detection of a higher amplitude interference pattern, and provide an improved input to the phase tracker, thus enabling more stable phase tracking.

Figure 15:
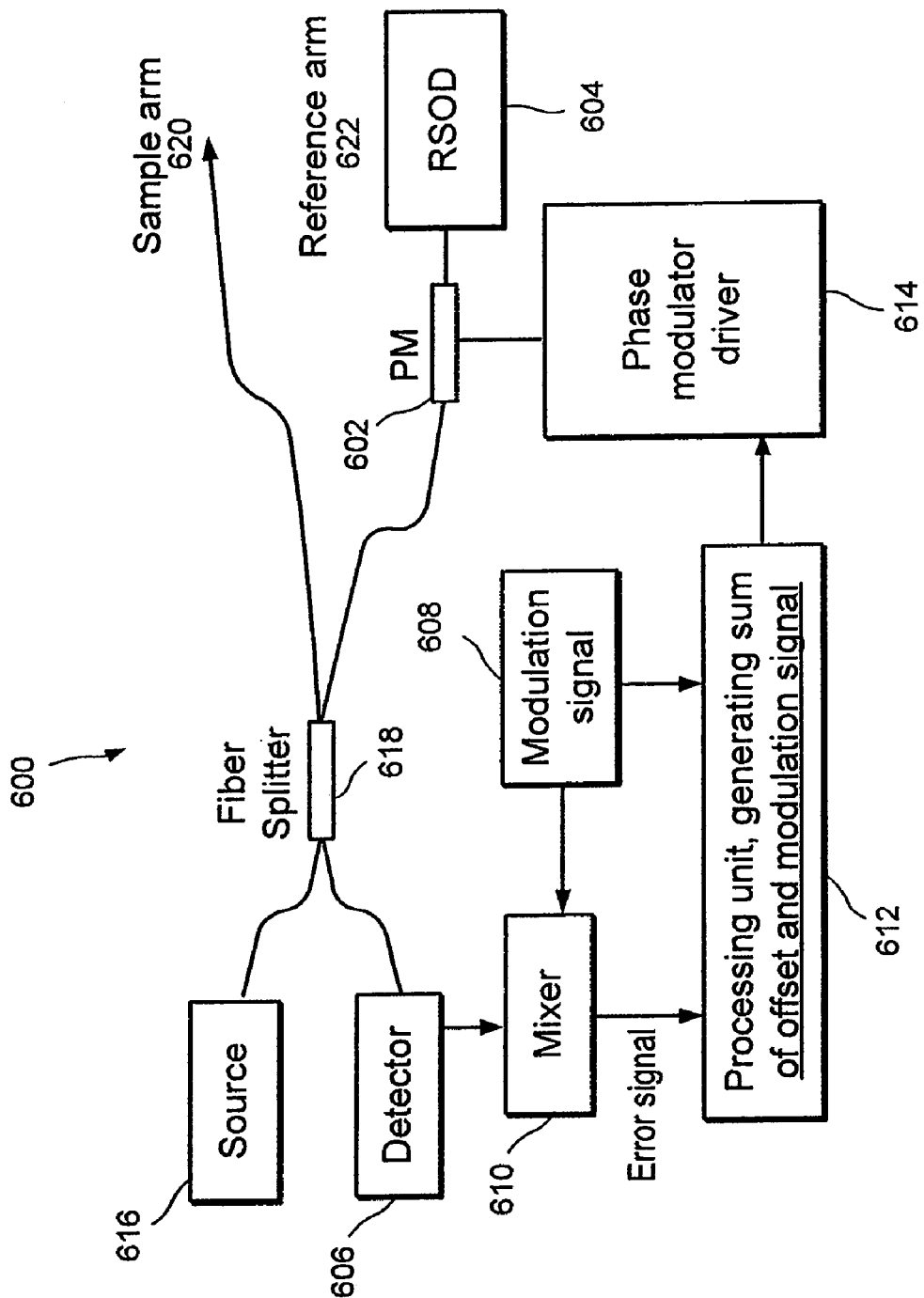
FIG. 15 is an embodiment of a phase tracker system with an extended phase lock range.

FIG. 15 shows one exemplary embodiment of a phase tracker system 600 according to the present invention with an extended phase lock range, by combining a fast element (EO phase modulator) 602 to modulate the path length difference over a small range, and a slower element (RSOD) 604 to modulate the path length over an extended range. The detector 606 signal is mixed with the phase modulator modulation frequency 608 by a mixer 610 and low pass filtered (filter not shown) to generate an error signal. The processing unit 612 preferably processes the error signal to generate an offset voltage, and adds this offset voltage to the modulation signal 608, so as to generate the output for the phase modulator driver 614. In addition, the processing unit 612 can generate a signal to the RSOD 604 to provide extended range tracking of the phase over distances of several millimeters. Light source 616, fiber splitter 618, sample arm 620 and reference arm 622 are shown, and are described herein.

Mixer Implementation: The intensity I(t) at the detector at a given moment within a single oscillation of the fringe pattern is given by $I(t)=\cos[\phi(t)]$ where the phase $\phi$ gives the position in the fringe. For $\phi=0$, the signal is at a fringe maximum, for $\phi=\pi$, the signal is at a fringe minimum. At an arbitrary moment t, the phase $\phi(t)$ is given by, $\phi(t)=\alpha+\beta\sin(\omega t)$ where $\alpha$ describes the position within a single oscillation of the fringe pattern, and $\beta^*\sin(\omega t)$ is the phase modulation introduced by the phase modulator, with $\beta$ the amplitude of the phase modulation, and ω the frequency of the phase modulation signal. The intensity at the photodetector I(t) can be mixed with a carrier at frequency ω and 2ω, resulting in the mixer signal MixerC(t), MixerS(t), Mixer2ωC(t) and Mixer2ωS(t), $$MixerC(t)=\cos(\omega t)*\cos(\alpha+\beta \sin(\omega t));$$

$$MixerS(t)=\sin(\omega t)*\cos(\alpha+\beta \sin(\omega t))$$

$$Mixer2\omega C(t)=\cos(2\omega t)*\cos(\alpha+\beta \sin(\omega t));$$

$$Mixer2\omega S(t)=\sin(2\omega t)*\cos(\alpha+\beta \sin(\omega t))$$

The time average over a single oscillation of the carrier frequency ω of MixerC, MixerS, Mixer2ωC and Mixer2ωS is given by, $$\overline{MixerC(t)}=0; \overline{MixerS(t)}=\sin(\alpha)*J_1(\beta);$$

$$\overline{Mixer2\omega C(t)}=\cos(\alpha)*J_2(\beta); \overline{Mixer2\omega S(t)}=0$$

where $J_1(\beta)$ and $J_2(\beta)$ are a Bessel functions of the first kind; its value depends on β, the amplitude of the phase modulation. Thus, the signal $\overline{MixerS(t)}$ and $\overline{Mixer2\omega C(t)}$ are proportional to $\sin(\alpha)$ and $\cos(\alpha)$, respectively, with α the position within a single oscillation of the fringe pattern. The mixer outputs $\overline{MixerS(t)}$ and $\overline{Mixer2\omega C(t)}$ are used as an error signal to generate an offset voltage to steer the phase modulator to a new center position that minimizes the error signal, and locks the interferometer output on a fringe maximum or minimum, or a zero crossing, respectively. The complex spectral density can now be determined by two consecutive array scans, one where the error signal sin(α) is minimized, and the next where the error signal cos(α) is minimized, resulting in a 90 degrees phase shift between the two interference patterns. Using this mixing arrangement, the complex spectral density can be obtained rapidly and without resorting to an additional mechanical arrangement for changing the phase of the reference arm light.

FIG. 10 shows one exemplary embodiment of a SD OCT system 700 with phase tracker for providing balanced detection according to the present invention. In this embodiment, a source 702 provides light which passes through a splitter 704, which sends part of the light to a sample probe 706 and the remainder of the light to a Rapid Scanning Optical Delay ("RSOD") line 708. Light is passed from the RSOD 708 to the phase modulator PM 710. Light from the phase modulator PM 710 is sent through a splitter 712, and then through two additional splitters 714 and 716, a portion of the output of which is sent as balanced detection outputs to spectral detection units (not shown, but as described elsewhere herein) and the remainder of the output is sent to the phase tracker assembly 720. In the phase tracker assembly 720, phase tracker detectors $D_1$ and $D_2$, 722 and 724, receive the partial output of the pair of splitters 714 and 716, which in turn send signal to a mixer 726 to generate an error signal. A processing unit 728 processes the error signal, where the sum generation of offset voltage and adds this to the modulation signal 730 to generate the output for the phase modulator driver 732. Modulation signal, shown at box 730, is forwarded to the mixer 726 and the processing unit 726. In addition, the fringe amplitude could be too small for the phase tracker to lock. Alternatively, a secondary source with longer coherence length could be coupled to the system 700 to provide a larger fringe amplitude to the phase tracker.

Figures 15B, 15C:
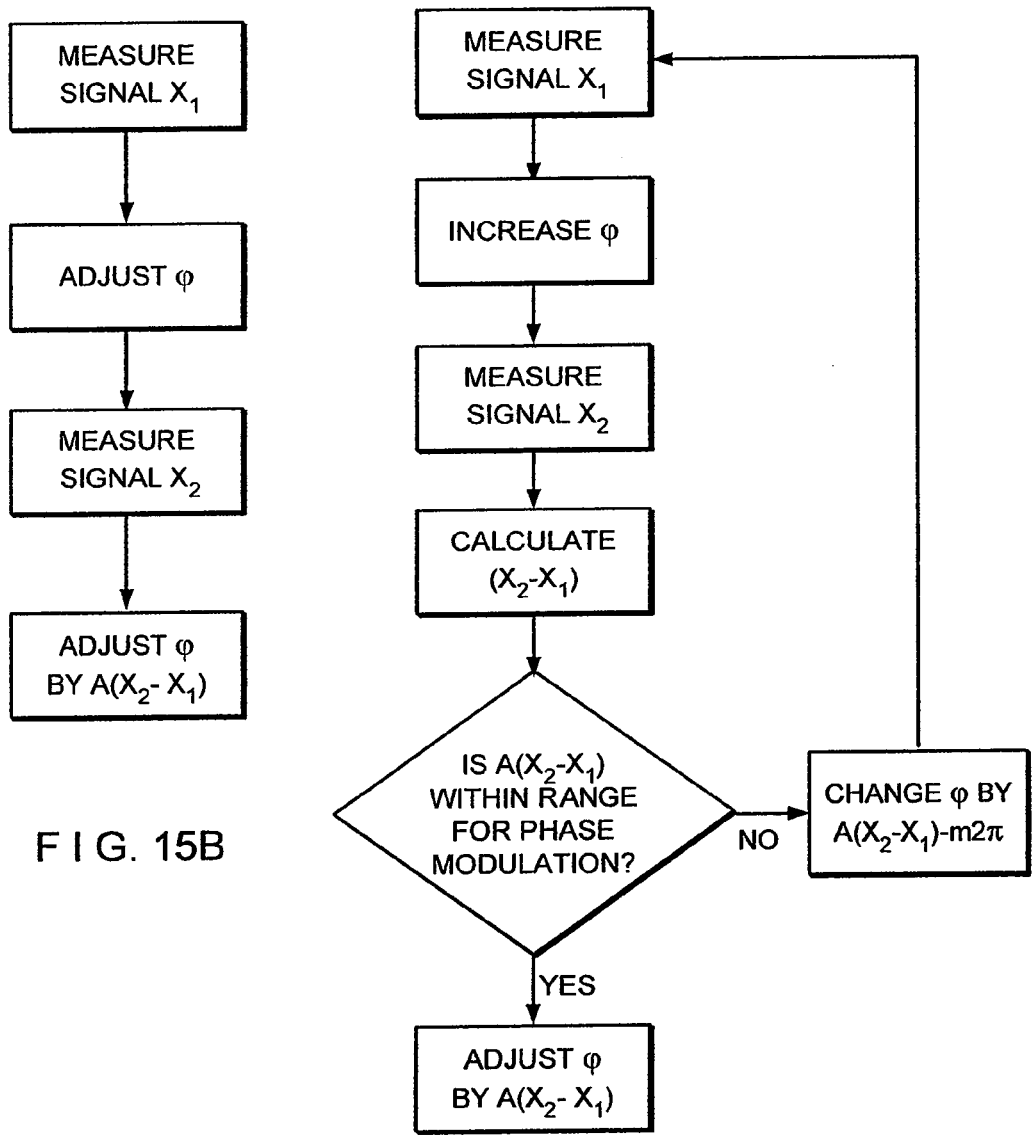

The present invention provides a method for tracking phase in an imaging system, as shown in FIGS. 15A-C the method comprising the steps of: (a) measuring a signal received from the sample arm; (b) increasing a phase of the signal; (c) measuring a first signal partition of the signal defined as $x_1$ at least one peak of the signal; (d) determining whether to increase or decrease the phase of the signal by an incremental amount; (e) after step (d), measuring a second signal partition of the signal following step d); and, if the signal is at its peak, remeasuring the signal and if the signal is not at its peak, repeating steps d) and e).

The method further may comprise that steps (a)-(f) are performed in parallel with other imaging processes. The adjustment of phase "φ" is defined as $A(x_2-x_1)$, where "A" is a constant. Furthermore, optionally, step d) may further comprise the substeps of d1) determining whether $A(x_2-x_1)$ is within range of the phase modulator; and d2) changing φ by an amount equal to $A(x_2-x_1)$ if $A(x_2-x_1)$ is within the range or changing φ by an amount equal to $A(x_2-x_1)-m2\pi$ if $A(x_2-x_1)$ is outside of the range, where M is an integer greater than 1. The method may optionally further comprise a substep d3) remeasuring signal $x_1$.

Data Acquisition and Processing Unit

In general, the data collected by the spectrometer are sampled with equal wavelength increments. Fourier transform, however, links z and k space (or t and w). Because of the non-linear relation between k and λ the acquired spectrum is interpolated to create evenly spaced samples in the k domain. Alternatively, the light could be dispersed in such a way on the detection array that the light is samples in equal intervals in k space, such that the interpolation becomes obsolete. Alternatively, the detection array spacing could be designed to sample the light evenly spread in the k domain, such that the interpolation becomes obsolete. To achieve the optimal point spread function, dispersion in the sample and reference arm of the interferometer should preferably be balanced. Dispersion imbalance can be corrected by digital processing.

The present invention provides a probe for locating atherosclerotic plaque in a blood vessel, comprising: an interferometer; a spectral separating unit which splits signal received from the interferometer into a plurality of optical frequencies; and a detector arrangement capable of detecting at least a portion of the optical frequencies received from the spectral separating unit.

The present invention further provides an apparatus for delivering a therapeutic agent, comprising: a probe disposed in the housing and comprising: an interferometer, a spectral separating unit which splits signal received from the interferometer into a plurality of optical frequencies, a detector arrangement capable of detecting at least a portion of the optical frequencies received from the spectral separating unit; and a conduit cooperating with the probe, and comprising a proximal end for receiving the therapeutic agent and a distal end for delivering the therapeutic agent at a predetermined location, the location being determined by imaging the environment in proximity to the distal end using the probe.

An exemplary embodiment of the present invention will be further described below in connection with the following example, which is set forth for purposes of illustration only.

EXAMPLE

The method according to the present invention was verified in the laboratory by the following experiment.

Figure 16:
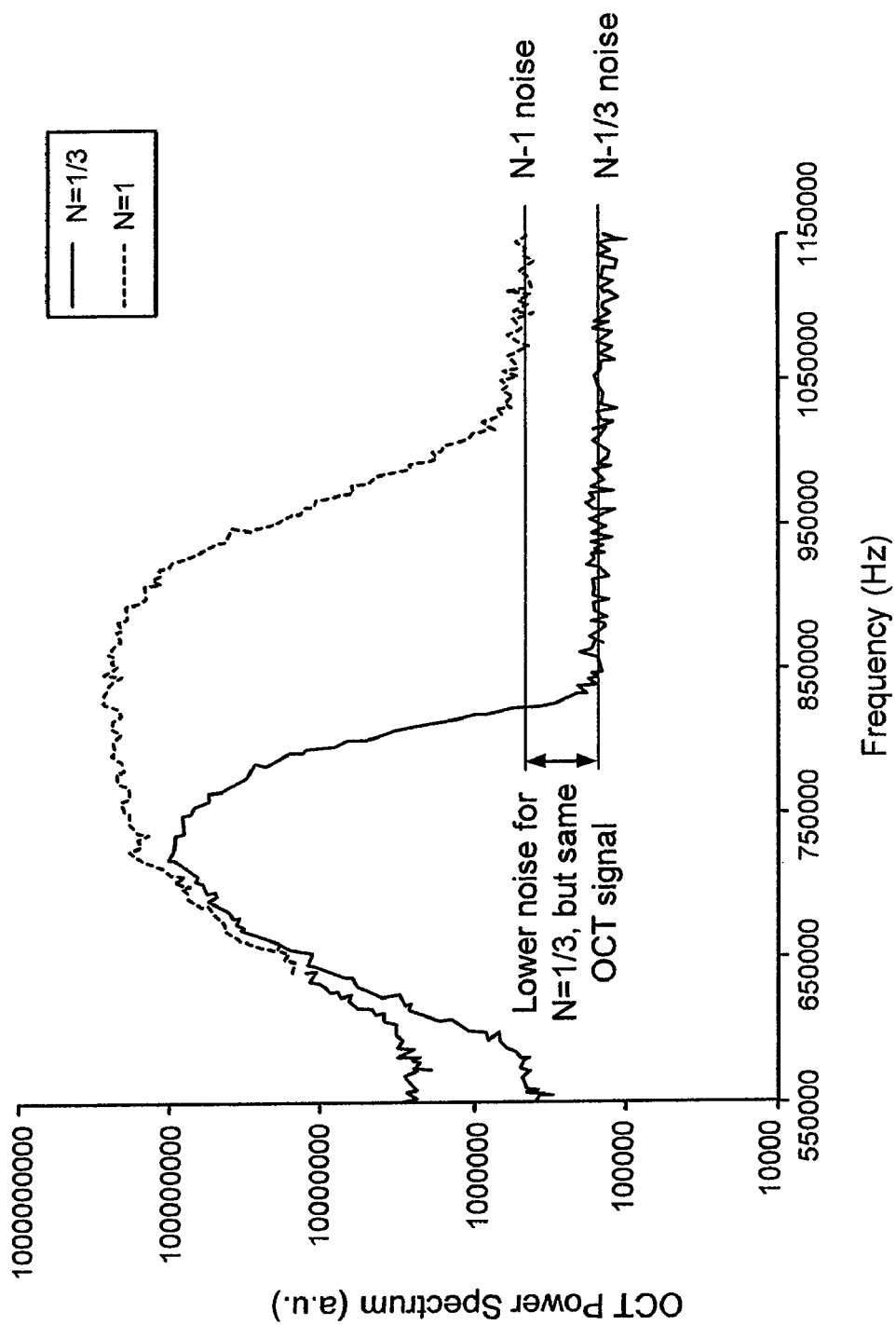
FIG. 16 is a graph of frequency versus OCT power spectrum.

In the existing OCT system, the shot noise power spectrum as determined from the spectral density due to the reference arm optical power was measured. Then ⅔ of the spectrum from the reference arm was blocked, and experimentally it was verified that the shot noise power spectrum was reduced by a factor of three, thus demonstrating that the shot noise is reduced by a factor of 3 if the spectrum is split in three spectral bands (see FIG. 16). The upper curve (gray dotted line) shows the power spectrum for the OCT signal with one detector. For the lower curve (solid line), the spectrum was limited by ⅓ with a corresponding factor of 3 improvement in signal to noise ratio. This data was generated by experiment, blocking ⅔ of the spectrum in a grating-based double-passed pulse shaping rapidly scanning optical delay line.

An object with low reflectivity was inserted in the sample arm. Using the full spectral width of the source, the power spectrum of the interference between sample and reference arm light was determined in the lower half of the spectral density. Then the upper part of the source spectrum was blocked in the reference arm, and it was verified that the lower ⅓ of the power spectrum of the interference between sample and reference arm light had the same magnitude as in the previous measurement (see FIG. 17). This figure demonstrates that the signal amplitude is equal for the N=1 and N=⅓ cases where they overlap. The result of equal amplitude signal for N=⅓ case and the 3-fold lower noise for the N=⅓ case (see FIG. 6) demonstrates that splitting into N wavelength bands increases the SNR by a factor of N.

This demonstrates that when the light in the detection arm is split in two spectral bands, the spectral density of the interference between sample and reference arm light within the spectral bandwidth of a single detector is unchanged. Combined with the measurement that showed a reduction in the shot noise power spectrum, the conclusion is that a reduction of shot noise can be realized by splitting the detection arm light in separate spectral bands.

Experimental verification of the noise reduction.

To demonstrate the noise reduction in Spectral Domain OCT, an OCT system was used, including a Rapid Scanning Optical Delay line (RSOD) was used in the reference arm, enabling portions of the spectrum to be blocked. Detector signals were digitized at 2.5 Msamples/sec, allowing digital processing of the fringe information. First, the thermal noise density of the detector was measured as a function of frequency by blocking all light onto the detector. Second, the shot noise density of the reference arm power was measured with only the reference arm power incident on the detector. Third, both the sample and reference arm light were incident on the detector. The sample was a single scattering surface mounted in a model eye and 512 depth profiles were acquired in 2 seconds. The power density $I(f)^2$ was measured, which is proportional to the spectral density squared (see Eq. (9)). Then we blocked half of the spectrum in the reference and measured again the shot noise density of the reference arm by blocking the sample arm, and the power density $I(f)^2$ when both sample and reference arm light were incident on the detector. Shot noise and power densities were corrected for thermal noise by subtraction. Thermal noise was at least a factor of 3 smaller than the lowest shot noise level.

FIG. 18 shows a graph of power density for the full spectrum, and with half of the spectrum blocked in the reference arm, as a function of frequency. The solid line shows the power density for the full spectrum. The shot noise level measured while the sample arm was blocked is also shown. The dashed line shows the power density with half the spectrum blocked in the sample arm. The shot noise level measured while the sample arm was blocked is also shown. FIG. 18 demonstrates that the shot noise level was reduced by a factor of 2 by blocking half the spectrum in the reference arm. At the same time, the signal at frequencies corresponding to wavelengths that were not blocked in the reference arm remained the same.

As is evident from FIG. 18, which summarizes the measured results, the shot noise density is reduced by approximately a factor of 2 by blocking half the spectrum in the reference arm. FIG. 19 shows that after subtraction of the shot noise levels from the corresponding signals, the power densities for those frequencies that corresponded to wavelengths that were not blocked in the reference arm remained the same. This demonstrates that the shot noise density is reduced by a factor of 2 when the total reference arm power is reduced by a factor of 2 by blocking half the spectrum, while the signal power density for wave lengths not blocked in the reference arm remains unchanged.

FIG. 19 shows a graph of the square root of the power densities for the full spectrum, and for half the spectrum blocked in the reference arm as a function of frequency. The solid line shows the spectrum after subtraction of the respective shot noise. The dashed line shows the half spectrum after subtraction of the respective shot noise. FIG. 13 demonstrates that after subtracting the respective shot noise contributions, the signal at frequencies corresponding to wave lengths that were not blocked in the reference arm remained the same.

The next experiment further demonstrated that by dispersing the spectrum in the detection arm over several detectors, and by selectively band pass filtering the signals of each detector, the SNR is increased. The detection arm light was dispersed over 4 detectors by a diffraction grating as shown in FIG. 13, and the detector signals were separately amplified by transimpedance amplifiers with a bandwidth of 600 kHz and simultaneously digitized.

FIG. 13 shows a schematic of an exemplary apparatus setup used to demonstrate SNR improvement by Spectral Domain OCT according to the present invention. Scanning of the reference arm 106 was performed with a Rapid Scanning Optical Delay line (RSOD) 120. Individual signals from the array detector 114 were amplified by transimpedence amplifiers, digitized by a 4-channel 2.5 MHz per channel A/D board and stored in computer memory (not shown).

First, the thermal noise density of all four detectors was measured. Second, the shot noise density of the reference arm light in each detector channel 116 was measured. Third, both the sample and reference arm light were incident on the detector 114. The sample 130 was a single scattering surface mounted in a model eye and 512 depth profiles were acquired in 2 seconds. The power density $I(f)^2$ in each detector channel 114 was measured. Then, the signals of the four detectors 114 were summed, and the combined power density $I(f)^2$ was determined. The results are shown in FIG. 20, which demonstrates that the shot noise is lower in each individual channel compared with the sum of all channels, but that the power densities $I(f)^2$ in the individual channels within their respective bandwidths are approximately equal to the power density $I(f)^2$ of the coherent sum of the four channels.

FIG. 20 shows a graph of the power densities for four separate detectors 116 of FIG. 13. The spectrum in the detection arm was dispersed over four separate detectors 116 by a diffraction grating 520. The shot noise levels for each individual detector 116 are significantly lower than for the coherent sum of the four detector channels. Bars at the top of the image indicate the signal pass band that was applied to the individual channels and the coherently summed channel to generate FIG. 21.

Figure 21:
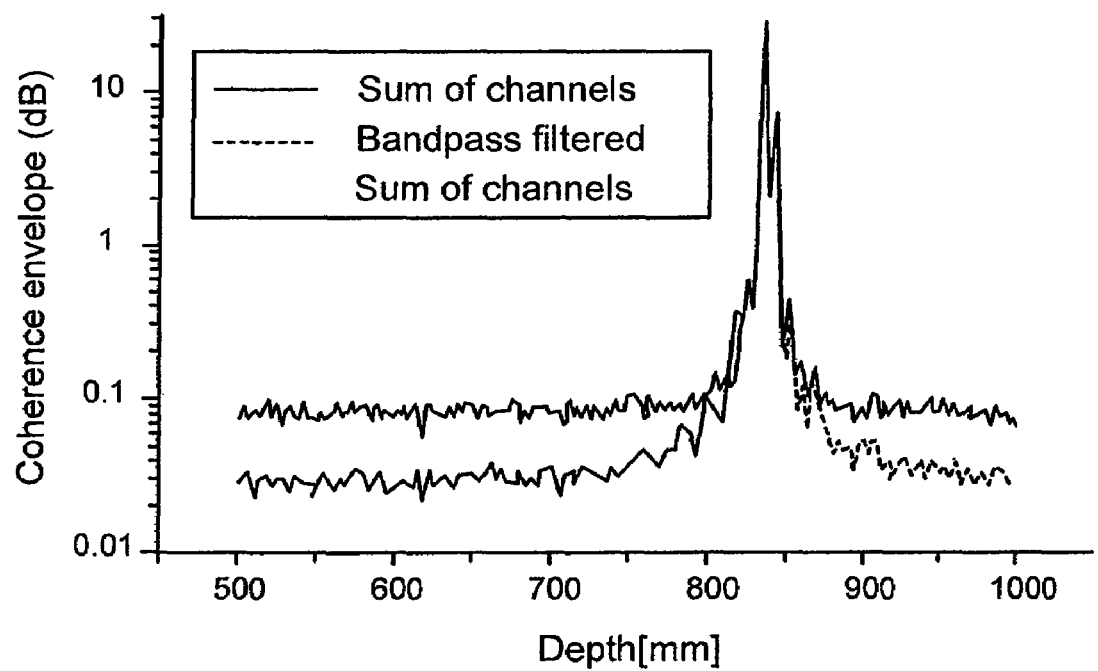
FIG. 21 is a graph of the coherence envelope for the coherently summed channels.

In FIG. 21, the square of the coherence envelope is shown for both the direct sum of all four detection channels and the coherent sum after digitally band pass filtering each detector channel with a bandwidth centered at the center frequency of the respective detector signal. FIG. 21 shows that the interference fringe signal I(t) of the direct sum and the band pass filtered coherent sum of the four detector signals results in virtually the same coherence envelope peak value, while the band pass filtered coherent sum of the four detector signals shows a significantly lower noise level than the direct coherent sum. Since the pass band of each individual channel was slightly larger than one third of the pass band of the full signal (pass bands are indicated in FIG. 20), an increase of SNR of a factor of 2.87 was expected. The noise level dropped by a factor of 2.8. However, band pass filtering also reduced the signals slightly, by a factor of 1.12, resulting in an effective increase in SNR of a factor of 2.5.

These experiments clearly demonstrate that spectrally dispersing the light in the detection arm can offer a significant SNR advantage.

FIG. 21 shows a plot of the coherence envelope for the coherently summed channels, and the coherently summed channels after band pass filtering each channel. The solid line is the sum of channels. The dashed line is the pass filtered sum 25 of channels. FIG. 21 clearly demonstrates the signal to noise gain that can be achieved by spectrally dispersing the signal in the detection arm over several individual detectors. In this example the noise level was reduced by a factor of approximately 2.8. Since the coherence peak was reduced by a factor of 1.12 due to some remaining signal fraction filtered out by the band pass filters, the actual SNR improvement was 2.5.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. It should further be noted that any patents, applications and publications referred to herein are incorporated by reference in their entirety.

What is claimed is:

1. An apparatus for optical imaging of at least one portion of a sample, comprising:
   a) an interferometer providing at least one signal;
   b) a spectral separating unit which splits the at least one signal received from the interferometer into a plurality of optical frequencies; and
   c) a plurality of detectors, each detector being configured to detect at least a portion of the optical frequencies received from the spectral separating unit, wherein the sample is scanned in a series of simultaneous illuminations of substantially all of areas of the sample to provide at least one radiation associated with the sample to be used by the interferometer to provide the at least one signal, wherein the interferometer receives at least one electro-magnetic radiation from a transmissive reference, and generates the at least one signal as a function of the at least one electro-magnetic radiation.

2. The apparatus according to claim 1, further comprising an arrangement which configured to at least one of:
   i. reconstruct the signal from the detectors by a mathematical manipulation of each plurality of signals obtained from the detectors, or
   ii. track a phase of the signal of the interferometer.

3. The apparatus according to claim 1, further comprising at least one arrangement which is configured to reconstruct the at least one signal from the detectors by a mathematical manipulation.

4. The apparatus according to claim 1, further comprising at least one arrangement which is configured to track the phase of the signal of the interferometer.

5. The apparatus according to claim 1, wherein the spectral separating unit comprises at least one of (i) an addressable mirror array or (ii) a waveguide filter.

6. The apparatus according to claim 1, wherein the spectral separating unit splits the signal into the bands.

7. The apparatus according to claim 1, wherein the detectors are provided in a form of a two-dimensional array.

8. The apparatus according to claim 1, wherein the spectral separating unit comprises a polarization separating unit.

9. The apparatus according to claim 1, wherein the spectral separating unit at least one of:
   i. comprises at least one of (i) an addressable mirror array or (ii) a waveguide filter, or
   ii. splits the signal into a plurality of bands, whereby at least one of the bands comprises spectra that has a comb-like structure.

10. The apparatus according to claim 1, wherein the interferometer comprises an arrangement generating a path length difference that is a fraction of a ranging depth of the interferometer.

11. An apparatus, comprising:
   a) a spectral separating arrangement configured to receive a plurality of electro-magnetic signals from an interferometer, and to separate the electromagnetic signals into a plurality of spectral bands, the electromagnetic signals being associated with characteristics of at least one of a plurality of portions of a sample, wherein at least two of the portions of the sample are irradiated simultaneously; and
   b) a detecting arrangement configured to detect at least one of the spectral bands received from the spectral separating arrangement, and configured to generate at least one resultant signal for use to image the at least one of the at least two of the portions of the sample, wherein the spectral separating arrangement receives at least one electro-magnetic radiation from a transmissive reference, and generates the spectral bands as a function of the at least one electromagnetic radiation.

12. A logic arrangement to provide data, which, when executed by a processing arrangement, configures the processing arrangement to execute the steps comprising of:
   a) receiving signals that correspond to spectral bands of more than one electro-magnetic signals from a detecting arrangement, the detecting arrangement detecting the spectral bands that are separated from the electromagnetic signals by a spectral separating arrangement, the spectral separating arrangement receiving the electromagnetic signals from an interferometer, the electromagnetic signals being associated with characteristics of at least one of a plurality of portions of a sample, wherein at least two of the portions of the sample are irradiated simultaneously, wherein the spectral bands are generated as a function of the at least one electromagnetic radiation associated with at least one electromagnetic radiation received from a transmissive reference; and
   b) generating the data based on information corresponding to the received signals.

13. A method for providing data, comprising the steps of:
   a) receiving signals that correspond to spectral bands of the at least one electro-magnetic signal from a detecting arrangement, the detecting arrangement detecting the spectral bands that are separated from the at least one electromagnetic signal by a spectral separating arrangement, the spectral separating arrangement receiving the electromagnetic signals from an interferometer, the electromagnetic signals being associated with characteristics of at least one of a plurality of portions of a sample, wherein at least two of the portions of the sample are irradiated simultaneously, wherein the spectral bands are generated as a function of the at least one electromagnetic radiation associated with at least one electromagnetic radiation received from a transmissive reference; and b) generating the data based on information corresponding to the received signals.

14. A storage medium including executable instructions thereon to provide data, wherein, when the executable instructions are executed by a processing system, the executable instructions configure the processing system to perform the steps comprising of:

a) receiving signals that correspond to spectral bands of a plurality of electro-magnetic signal from a detecting arrangement, the detecting arrangement detecting the spectral bands that are separated from the electromagnetic signals by a spectral separating arrangement, the spectral separating arrangement receiving the electromagnetic signals from an interferometer, the electromagnetic signals being associated with characteristics of at least one of a plurality of portions of a sample, wherein at least two of the portions of the sample are irradiated simultaneously, wherein the spectral bands are generated as a function of the at least one electromagnetic radiation associated with at least one electromagnetic radiation received from a transmissive reference; and b) generating the data based on information corresponding to the received signals.

15. An apparatus for optical imaging of at least one portion of a sample, comprising:

a) an interferometer providing at least one signal;

b) a spectral separating unit which splits the at least one signal received from the interferometer into a plurality of optical frequencies;

c) a plurality of detectors, each detector being configured to detect at least a portion of the optical frequencies received from the spectral separating unit, wherein the sample is scanned in a series of simultaneous illuminations of substantially all of areas of the sample to provide at least one radiation associated with the sample to be used by the interferometer to provide the at least one signal; and d) an arrangement configured to track the phase of the signal of the interferometer.

* * * * *